United States Patent
Huang et al.

(10) Patent No.: US 11,788,093 B2
(45) Date of Patent: Oct. 17, 2023

(54) CHIMERIC ANTIGEN RECEPTOR T-CELLS EXPRESSING INTERLEUKIN-8 RECEPTOR

(71) Applicant: University of Florida Research Foundation, Inc., Gainesville, FL (US)

(72) Inventors: Jianping Huang, Gainesville, FL (US); Linchun Jin, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 537 days.

(21) Appl. No.: 16/645,154

(22) PCT Filed: Sep. 6, 2018

(86) PCT No.: PCT/US2018/049694
§ 371 (c)(1),
(2) Date: Mar. 6, 2020

(87) PCT Pub. No.: WO2019/051047
PCT Pub. Date: Mar. 14, 2019

(65) Prior Publication Data
US 2021/0040487 A1    Feb. 11, 2021

Related U.S. Application Data

(60) Provisional application No. 62/570,317, filed on Oct. 10, 2017, provisional application No. 62/555,251, filed on Sep. 7, 2017.

(51) Int. Cl.
| | |
|---|---|
| *C12N 15/62* | (2006.01) |
| *A61K 9/00* | (2006.01) |
| *A61K 35/17* | (2015.01) |
| *C07K 14/725* | (2006.01) |
| *C07K 14/715* | (2006.01) |

(52) U.S. Cl.
CPC ............ *C12N 15/62* (2013.01); *A61K 9/0019* (2013.01); *A61K 35/17* (2013.01); *C07K 14/7051* (2013.01); *C07K 14/7155* (2013.01)

(58) Field of Classification Search
CPC ........ C12N 15/62; C12N 15/867; C12N 5/10; C07K 14/70596
See application file for complete search history.

(56) References Cited

U.S. PATENT DOCUMENTS

| | | |
|---|---|---|
| 7,872,106 B2 | 1/2011 | Paszty et al. |
| 2002/0197266 A1 | 12/2002 | Debinski |
| 2014/0010861 A1 | 1/2014 | Bancel et al. |
| 2014/0107189 A1 | 4/2014 | Bancel et al. |
| 2019/0336504 A1* | 11/2019 | Gill .................. A61P 35/00 |

FOREIGN PATENT DOCUMENTS

| | | | |
|---|---|---|---|
| WO | 2012/058460 A2 | 5/2012 | |
| WO | 2016/093878 A1 | 6/2016 | |
| WO | 2016/126608 A1 | 8/2016 | |
| WO | WO-2016126608 A1 * | 8/2016 | ............. A61K 35/17 |

OTHER PUBLICATIONS

Paul. Fundamental Immunology, 3rd Edition, Raven Press, New York, Chapters, pp. 292-295, 1993 (Year: 1993).*
MacCallum et al. Journal of Molecular Biology, 262:732-745, 1996 (Year: 1996).*
Vajdos et al. Journal of Molecular Biology, Jul. 5, 2002;320(2):415-28 (Year: 2002).*
Dotti et al. Immunology Reviews, 2014: 1-35, pp. 1-5 (Year: 2014).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Bork. Genome Research, 2000, 10:398-400 (Year: 2000).*
Wang et al. Clin Cancer Res; 23(9) May 1, 2017 (Year: 2017).*
Abolhassani et al., Combined immunodeficiency and Epstein-Barr virus-induced B cell malignancy in humans with inherited CD70 deficiency, J. Exp. Med., 214(1):91-106 (2017).
Adam et al., CD70 (TNFSF7) is expressed at high prevalence in renal cell carcinomas and is rapidly internalised on antibody binding, Br. J .Cancer., 95(3):298-306 (2006).
Ahmed et al., Her2-specific chimeric antigen receptor-modified virus-specific t cells for progressive glioblastoma: A phase 1 dose-escalation trial, JAMA Oncology, 3:1094-1101 (2017).
Ahmed et al., HER2-specific T cells target primary glioblastoma stem cells and induce regression of autologous experimental tumors, Clin. Cancer Res., 16(2):474-85 (2010).
Alfaro et al. Tumor-Produced intedeukin-8 attracts human myeloid-derived suppressor cells and elicits extrusion of neutrophil extracellular traps (NETs), Clin. Cancer Res., 22:3924-3936 (2016).
Au-Baker et al., Isolation and Flow Cytometric Analysis of Glioma-infiltrating Peripheral Blood Mononuclear Cells, J. Vis. Exp., e53676 (2015).
Bernhard et al., Adoptive transfer of autologous, HER2-specific, cytotoxic T lymphocytes for the treatment of HER2-overexpressing breast cancer, Cancer Immunology Immunotherapy, 57:271-280 (2008).
Bowman et al., The cloning of CD70 and its identification as the ligand for CD27, J. Immunol., 152(4):1756-1761 (1994).
Brat et al., Comprehensive, integrative genomic analysis of diffuse lower-grade gliomas, N. Engl. J. Med., 372(26):2481-2498 (2015).
Brown et al., Regression of Glioblastoma after Chimeric Antigen Receptor T-Cell Therapy, N. Engl. J. Med., 375(26):2561-2569 (2016).

(Continued)

*Primary Examiner* — Vanessa L. Ford
*Assistant Examiner* — Sandra Dillahunt
(74) *Attorney, Agent, or Firm* — MARSHALL, GERSTEIN & BORUN LLP

(57) ABSTRACT

An IL-8 receptor (e.g., CXCR1 or CXCR2) modified CAR T cell is provided, as well as a nucleic acid encoding the IL-8 modified CAR T cell and method of use.

12 Claims, 38 Drawing Sheets

Specification includes a Sequence Listing.

(56) References Cited

OTHER PUBLICATIONS

Chahlavi et al., Glioblastomas induce T-lymphocyte death by two distinct pathways involving gangliosides and CD70, Cancer Res., 65(12):5428-5438 (2005).
Chanmee et al., Tumor-associated macrophages as major players in the tumor microenvironment, Cancers (Basel), 6(3):1670-1690 (2014).
Che et al., Regulatory T cells resist virus infection-induced apoptosis, J. Virol., 89(4):2112-2120 (2015).
Chow et al., T cells redirected to EphA2 for the immunotherapy of glioblastoma, Mol. Ther., 21 (3):629-37 (2013).
Daniel et al., Dual-color bioluminescence imaging for simultaneous monitoring of the intestinal persistence of lactobacillus plantarum and lactococcus lactis in living mice, Applied and Environ. Microb., 81:5344-5349 (2015).
David et al., The IL-8/IL-8R axis: A double agent in tumor immune resistance, Vaccines, 4:22 (2016).
Diegmann et al., Immune escape for renal cell carcinoma: CD70 mediates apoptosis in lymphocytes, Neoplasia., 8(11):933-938 (2006).
Engelhardt, Molecular mechanisms involved in T cell migration across the blood-brain barrier, J. Neural. Transm. (Vienna), 113(4):477-485 (2006).
Eyquem et al., Targeting a CAR to the TRAC locus with CRISPR/Cas9 enhances tumour rejection, Nature, 543:113-117(2017).
Fernando et al., IL-8 signaling plays a critical role in the epithelial-mesenchymal transition of human carcinoma cells, Cancer Research, 71:5296-5306 (2011).
Ganss et al., Combination of T-cell therapy and trigger of inflammation induces remodeling of the vasculature and tumor eradication, Cancer Research, 62:1462-1470 (2002).
Ge et al., Tumor associated CD70 expression is involved in promoting tumor migration and macrophage infiltration in GBM, Int. J Cancer., 141(7):1434-1444 (2017).
Held-Feindt et al., CD70/CD27 ligand, a member of the TNF family, is expressed in human brain tumors, Int. J. Cancer., 98(3):352-356 (2002).
Hintzen et al., Characterization of the human CD27 ligand, a novel member of the TNF gene family, J. Immunol., 152(4):1762-1773 (1994).
Hintzen et al., Engagement of CD27 with its ligand CD70 provides a second signal for T cell activation, J. Immunol., 154(6):2612-2623 (1995).
Huang et al., Irradiation enhances human T-cell function by upregulating CD70 expression on antigen-presenting cells in vitro, J. Immunother., 34(4):327-335 (2011).
Huang et al., Modulation by IL-2 of CD70 and CD27 expression on CD8+ T cells: importance for the therapeutic effectiveness of cell transfer immunotherapy, J. Immunol., 176(12):7726-7735 (2006).
Huang et al., Soluble CD27-pool in humans may contribute to T cell activation and tumor immunity, J. Immunol., 190(12):6250-6258 (2013).
Huang et al., Survival, persistence, and progressive differentiation of adoptively transferred tumor-reactive T cells associated with tumor regression, J. Immunotherapy, 28:258-267 (2005).
International Application No. PCT/US2018/049694, International Preliminary Reporton Patentability, dated Mar. 19, 2020.
International Application No. PCT/US2018/049694, International Search Report and Written Opinion, dated Jan. 28, 2019.
Izawa et al., Inherited CD70 deficiency in humans reveals a critical role for the CD70-CD27 pathway in immunity to epstein-barr virus infection, J. Exp. Med., 214(1):73-89 (2017).
Jacobs et al., CD70: An emerging target in cancer immunotherapy, Pharmacol. Ther., 155:1-10 (2015).
Jin et al., CXCR1- or CXCR2-modified CAR T cells co-opt IL-8 for maximal antitumor efficacy in solid tumors, Nat. Commun., 10:4016 (2019).
Johnson et al., Rational development and characterization of humanized anti-EGFR variant III chimeric antigen receptor T cells for glioblastoma, Sci. Transl. Med., 7(275):275ra222 (2015).

Kalos et al., T cells with chimeric antigen receptors have potent antitumor effects and can establish memory in patients with advanced leukemia, Science Translational Medicine, 3:95ra73-95ra73 (2011).
Keller et al., Costimulatory ligand CD70 allows induction of CD8+ T-cell immunity by immature dendritic cells in a vaccination setting, Blood, 113(21):5167-5175 (2009).
Keu et al., Reporter gene imaging of targeted T cell immunotherapy in recurrent glioma, Sci. Trans. Med., 9:eaag2196(2017).
Koch et al., Interleukin-8 as a macrophage-derived mediator of angiogenesis, Science, 258:1798-1801 (1992).
Kochenderfer et al., Eradication of B-lineage cells and regression of lymphoma in a patient treated with autologous T cells genetically engineered to recognize CD19, Blood, 116:4099-4102 (2010).
Krenciute et al., Characterization and Functional Analysis of scFv-based Chimeric Antigen Receptors to Redirect T Cells to IL13Ra2-positive Glioma, Mol. Ther., 24(2):354-63 (2016).
Lee et al., T cells expressing CD19 chimeric antigen receptors for acute lymphoblastic leukaemia in children and young adults: a phase 1 dose-escalation trial, The Lancet, 385:517-528 (2015).
Li et al., IL-8 directly enhanced endothelial cell survival, proliferation, and matrix metalloproteinases production and regulated angiogenesis, J. Immun., 170:3369-3376 (2003).
Linchun et al., CD70, a novel target of CAR T-Cell therapy for gliomas, Neuro-Oncology, 20(1) 55-65 (2018).
Liu et al., The CXCL8-CXCR1/2 pathways in cancer, Cytokine Growth Factor Rev., 31:61-71 (2016).
Masopust et al., The integration of T cell migration, differentiation and function, Nat. Rev. Immun., 13:309-320 (2013).
Maude et al., Chimeric antigen receptor T cells for sustained remissions in leukemia, New Eng. J. Med., 371:1507-1517(2014).
Mellman et al., Cancer immunotherapy comes of age, Nature, 480(7378):480-489 (2011).
Meyers et al., Optimal alignments in linear space, Computer Appl. Biol. Sci., 4:11-17 (1988).
Miao et al., EGFRvIII-specific chimeric antigen receptor T cells migrate to and kill tumor deposits infiltrating the brain parenchyma in an invasive xenograft model of glioblastoma, PLoS One, 9(4):e94281 (2014).
Morgan et al., Recognition of glioma stem cells by genetically modified T cells targeting EGFRvIII and development of adoptive cell therapy for glioma, Hum Gene Ther., 23(10):1043-1053 (2012).
Ning et al., lnterleukin-8 is associated with proliferation, migration, angiogenesis and chemosensitivity in vitro and in vivo in colon cancer cell line models, Int. J Cancer, 128:2038-2049 (2011).
Nolte et al., Timing and tuning of CD27-CD70 interactions: The impact of signal strength in setting the balance between adaptive responses and immunopathology, Immunol. Rev., 229(1):216-231 (2009).
O'Rourke et al., A single dose of peripherally infused EGFRvIII-directed CAR T cells mediates antigen loss and induces adaptive resistance in patients with recurrent glioblastoma, Sci. Trans. Med., 9:eaaa0984 (2017).
Oelkrug et al., Enhancement of T cell recruitment and infiltration into tumours, Clin. Exp. Immunol., 178(1):1-8 (2014).
Pellegatta et al., Constitutive and TNF (Alpha)-inducible expression of chondroitin sulfate proteoglycan 4 in glioblastoma and neurospheres: Implications for CAR-T cell therapy, Sci. Trans. Med., 10:eaao2731 (2018).
Porter et al., Chimeric antigen receptor T cells persist and induce sustained remissions in relapsed refractory chronic lymphocytic leukemia, Sci. Trans. Med., 7:303ra139-303ra139 (2015).
Porter et al., Chimeric antigen receptor-modified T cells in chronic lymphoid leukemia, New Eng. J. Med., 365:725-733 (2011).
Robbins et al., Cutting edge: persistence of transferred lymphocyte clonotypes correlates with cancer regression in patients receiving cell transfer therapy, J. Immunology, 173:7125-7130 (2004).
Ronald et al., A PET imaging strategy to visualize activated T cells in acute graft-versus-host disease elicited by allogenic hematopoietic cell transplant, Cancer Research, 77:2893-2902 (2017).
Rosenberg et al., Adoptive cell transfer: A clinical path to effective cancer immunotherapy, Nat. Rev. Cancer, 8(4):299-308 (2008).
Rovai et al., The murine neutrophil-chemoattractant chemokines LIX, KC, and MIP-2 have distinct induction kinetics, tissue distri-

(56) References Cited

OTHER PUBLICATIONS butions, and tissue-specific sensitivities to glucocorticoid regulation in endotoxemia, J. Leukocyte Biol., 64:494-502 (1998).
Ruf et al., pVHL/HIF-regulated CD70 Expression is associated with infiltration of CD27+ lymphocytes and increased serum levels of soluble CD27 in clear cell renal cell carcinoma, Clin. Cancer Res., 21(4):889-898 (2015).
Ryan et al., Targeting Pancreatic and Ovarian Carcinomas Using the Auristatin-Based anti-CD70 Antibody-Drug Conjugate SGN-75, Br. J. Cancer., 103(5):676-684 (2010).
Sampson et al., EGFRvIII mCAR-modified T-cell therapy cures mice with established intracerebral glioma and generates host immunity against tumor-antigen loss, Clin. Cancer Res., 20:972-984 (2014).
Sengupta et al., Chimeric antigen receptors for treatment of glioblastoma: a practical review of challenges and ways to overcome them, Cancer Gene. Therapy, 24:121-129 (2016).
Shaffer et al., T cells redirected against CD70 for the immunotherapy of CD70-positive malignancies, Blood, 117(16):4304-4314 (2011).
Shcherbakova et al., Near-infrared fluorescent proteins for multicolor in vivo imaging, Nat. Methods, 10, 751-754 (2013).
Shiina et al., CAR T cells targeting podoplanin reduce orthotopic glioblastomas in mouse brains, Cancer Immunol. Res, 4(3):259-68 (2016).
Silence et al., ARGX-110, a highly potent antibody targeting CD70, eliminates tumors via both enhanced ADCC and immune checkpoint blockade, Mabs., 6(2):523-32 (2014).
Singh et al., Ultraviolet B irradiation promotes tumorigenic and metastatic properties in primary cutaneous melanoma via induction of interleukin 8, Cancer Research, 55:3669-3674 (1995).
Slaney et al., Trafficking of T cells into tumors, Cancer Research, 74:7168-7174 (2014).
Smith et al., In situ programming of leukaemia-specific T cells using synthetic DNA nanocarriers, Nat. Nanotech., 12:813-820 (2017).
Stupp et al., Effects of radiotherapy with concomitant and adjuvant temozolomide versus radiotherapy alone on survival in glioblastoma in a randomised phase III study: 5-year analysis of the EORTC-NCIC trial, Lancet. Oneal., 10(5):459-466 (2009).
Stupp et al., Radiotherapy plus concomitant and adjuvant temozolomide for glioblastoma, N. Engl. J. Med., 352(10):987-996 (2005).
Trebing et al., CD70-restricted specific activation of TRAILR1 or TRAILR2 using scFv-targeted TRAIL mutants, Cell Death Dis., 5(1):e1035 (2014).
Venner et al., Interleukin-8 and melanoma growth-stimulating activity (GRO) are induced by ultraviolet B radiation in human keratinocyte cell lines, Experimental Dermatology, 4:138-145 (1995).
Verhaak et al., Integrated genomic analysis identifies clinically relevant subtypes of glioblastoma characterized by abnormalities in PDGFRA, IDH1, EGFR, and NF1, Cancer Cell., 17(1):98-110 (2010).
Wang et al., Preclinical evaluation of chimeric antigen receptors targeting CD70-Expressing cancers, Clin. Cancer Res., 23(9):2267-2276 (2017).
Watanabe et al., Chemoattractants for neutrophils in lipopolysaccharide-induced inflammatory exudate from rats are not interleukin-8 counterparts butgro-gene-product/melanoma-growth-stimulating-activity-related factors, Eur. J. Biochem., 214:267-270 (1993).
Waugh et al., The interleukin-8 pathway in cancer, Clin. Cancer Res., 14:6735-6741 (2008).
Wischhusen et al., Identification of CD70-mediated apoptosis of immune effector cells as a novel immune escape pathway of human glioblastoma, Cancer Res., 62(9):2592-2599 (2002).
Woude et al., Migrating into the tumor: a roadmap for T cells, Trends in Cancer, 3:797-808 (2017).
Yang et al., Development of optimal bicistronic lentiviral vectors facilitates high-level TCR gene expression and robust tumor cell recognition, Gene Therapy, 15(21):1411-1423 (2008).
Zhou et al., Telomere length of transferred lymphocytes correlates with in vivo persistence and tumor regression in melanoma patients receiving cell transfer therapy, J. Immunol., 175(10):7046-7052 (2005).

\* cited by examiner

Table 1 Summary of CD70 expression from tissue microarray analysis of carcinomas using ICI [11]

| Tumor type | CD70+ of total | %CD70+ |
|---|---|---|
| Kidney[a] | 204 of 283 | 72 |
| Pancreas | 35 of 140 | 25 |
| Larynx or pharynx[b] | 18 of 82 | 22 |
| Melanoma | 15 of 96 | 16 |
| Ovary | 37 of 241 | 15 |
| Lung adenocarcinoma | 17 of 172 | 10 |
| Colon | 17 of 194 | 9 |
| Breast | 5 of 204 | 2 |
| Brain | 6 of 59 | 10 |

[a] 189 of 230 (82%) clear cell carcinoma and 4 of 8 (50%) papillary carcinoma.
[b] Include nasopharyngeal cancer.

*FIG. 2*

Table 2 Cell surface expression of CD27 and CD70 in cancer cell lines

| Cell line | Type | CD70 | CD27 |
|---|---|---|---|
| Raji | NHL | +++ | +++ |
| U266 | MM | +++ | - |
| Amo-1 | MM | +++ | - |
| RPMI | MM | ++ | -/+ |
| INA6 | MM | - | - |
| KMS-11 | MM | ++ | - |
| MM1.S | MM | ++ | - |
| KMS12.BM | MM | +++ | +++ |
| JNN3 | MM | +++ | - |
| Mino | MCL | +++ | - |
| Jeko-1 | MCL | +++ | - |
| Rec-1 | MCL | +++ | - |
| Granta-519 | MCL | +++ | + |
| MJ(G11) | CTCL | +++ | - |
| JVM3 | CLL | +++ | - |
| Ramos-Ra1 | Burkitt | ++ | +++ |
| BJAB | Burkitt | +++ | -/+ |
| Daudi | Burkitt | ++ | - |
| SuDHL6 | DLBCL | ++ | - |
| Panc-1 | Pancreatic cancer | +++ | + |
| Panc89 | Pancreatic cancer | ++ | + |
| PancTu1 | Pancreatic cancer | - | - |
| MiaPaca-2 | Pancreatic cancer | - | - |
| Colo357 | Pancreatic cancer | - | - |
| A498 | RCC | +++ | - |
| 786-O | RCC | +++ | + |
| FaDu | SCC | - | - |
| HLaC-78 | SCC | -/+ | - |
| WM-35 | Melanoma | -/+ | - |
| WM-3211 | Melanoma | - | - |
| WM-115 | Melanoma | +++ | - |

FIG. 3

| | | | |
|---|---|---|---|
| WM-1552C | Melanoma | +/++ | -- |
| WM793 | Melanoma | -/+ | - |
| WM-3248 | Melanoma | ++ | - |
| SK-mel-19 | Melanoma | - | - |
| MV3 | Melanoma | - | - |
| WM-852 | Melanoma | + | - |
| WM-451-LU | Melanoma | - | - |
| WM-1205Lu | Melanoma | +++ | - |
| BLM | Melanoma | - | - |
| OAW-42 | Ovarian cancer | -/+ | - |
| SKOV-3 | Ovarian cancer | + | - |
| OVCAR3 | Ovarian cancer | +/+ | - |
| GaMG | Glioblastoma | -/+ | - |
| U87 | Glioblastoma | + | - |
| U343 | Glioblastoma | + | - |
| Ln18 | Glioblastoma | - | - |

Abbreviations; CLL, chronic lymphocytic leukemia; CTCL, Cutaneous T-cell lymphoma; DLBCL diffuse large B-cell lymphoma; MCL, mantle cell lymphoma; MM, multiple myeloma; NHL, non-Hodgkin lymphoma ; RCC, renal cell carcinoma; SCC, squamous cell cancer. Cells were analyzed by using FACS. +++ indicates very high expression, for example, like Mino cells (Figure 5A), ++ indicates high expression, for example, like OVCAR3 cells (Figure5A),+indicates significant expression, - indicates lack of significant binding

FIG. 3Cont.

Table 3 Overview of CD70 expression by immunohistochemistry on hematological and solid malignancies

| Malignancy | Reference | IHC Method | CD70 antibody | CD70 expression CD70+/total | Percentage CD70+ | Threshold for CD70 positivity |
|---|---|---|---|---|---|---|
| Hematological malignancies Non-Hodgkin lymphoma | McEarchern et al., 2008 | IHC-FFPE | mAb SG-21.1 C1 | 71/119 | 60% | n.s. |
|  | Tannir et al., 2014 | IHC-FFPE000000 | n.s | 82/107 | 77% | n.s. |
| Diffuse large B cell lymphoma | Lens et al., 1999 | IHC-Fr | mAB 2F2 | 15/21 | 71% | 20% |
|  | Adam et al., 2006 | IHC-Fr | mAb HNE5.1 | 4/6 | 67% | n.s. |
| Follicular lymphoma | Lens et al., 1999 | IHC-Fr | mAB 2F2 | 6/18 | 33% | 20% |
|  | Adam et al., 2006 | IHC-Fr | mAb HNE5.1 | 0/8 | 0% | n.s. |
| Mantle Cell lymphoma | Lens et al., 1999 | IHC-Fr | mAB 2F2 | 1/4 | 25% | 20% |
| Burkitt lymphoma | Lens et al., 1999 | IHC-Fr | mAB 2F2 | 1/4 | 25% | 20% |
| CAEBV associated T cell lymphoma | Shaffer et al., 2012 | IHC-FFPE | n.s | 1/1 | 100% | n.s. |
| Hodgkin lymphoma | Gruss & Kadin, 1996 | IHC-? | n.s | n.s. | 96% | n.s. |
|  | McEarchern et al., 2008 | IHC-FFPE | mAb SG-21.1 C1 | 23/24 | 97% | n.s. |
| leukemia B-cell chronic lymphocytic leukemia | Lens et al., 1999 | IHC-Fr | mAB 2F2 | 3/6 | 50% | 20% |
|  | Adam et al., 2006 | IHC-Fr | mAb HNE5.1 | 0/2 | 0% | n.s. |
| Multiple myeloma | McEarchern et al., 2008 | IHC-FFPE | mAb SG-21.1 C1 | 9/22 | 41% | n.s. |
| Solid malignancies renal cell carcinoma | McEarchern et al., 2008 | IHC-FFPE | mAb SG-21.1 C1 | 14/20 | 70% | n.s. |
|  | Tannir et al., 2014 | IHC-FFPE | n.s | 111/127 | 87% | n.s. |
| Clear cell | Junker et al., 2005 | IHC-Fr | mAb HNE5.1 | 41/41 | 100% | n.s. |
|  | Diegmann et al., 2005 | IHC-Fr | mAb HNE5.1 | 10/10 | 100% | n.s. |
|  | Adam et al., 2006 | IHC-Fr | mAb HNE5.1 | 16/20 | 80% | n.s. |
|  | Law et al., 2006 | IHC-Fr | mAB 2F2 | 71/131 | 54% | 25% |
|  | Ryan et al., 2010 | IHC-FFPE | 1C1/5D12Ab | 189/230 | 81% | 1% |

FIG. 4

|  |  |  |  |  | |
|---|---|---|---|---|---|
|  | Jilaveanu et al., 2012 | IHC-ISH | n.s | 113/232 | 49% | v>20.1 |
| Papillary | Junker et al., 2005 | IHC-Fr | mAb HNE5.1 | 1/9 | 5% | 5% |
|  | Adam et al., 2006 | IHC-Fr | mAb HNE5.1 | 0/3 | 0% | n.s. |
|  | Law et al., 2006 | IHC-Fr | mAB 2F2 | 9/23 | 39% | 25% |
|  | Ryan et al., 2010 | IHC-FFPE | 1C1/5D12Ab | 4/8 | 50% | 1% |
|  | Jilaveanu et al., 2012 | IHC-ISH | n.s | 9/46 | 19% | v>20.1 |
| Chromophobe | Junker et al., 2005 | IHC-Fr | mAb HNE5.1 | 1/5 | 20% | n.s. |
|  | Law et al., 2006 | IHC-Fr | mAB 2F2 | 0/6 | 0% | 25% |
| Oncocytomas | Junker et al., 2005 | IHC-Fr | mAb HNE5.1 | 0/3 | 0% | n.s. |
|  | Adam et al., 2006 | IHC-Fr | mAb HNE5.1 | 0/1 | 0% | n.s. |
|  | Jilaveanu et al., 2012 | IHC-ISH | n.s | 1/20 | 5% | v>20.1 |
| Sarcomatoid | Adam et al., 2006 | IHC-Fr | mAb HNE5.1 | 0/1 | 0% | n.s. |
|  | Jilaveanu et al., 2012 | IHC-ISH | n.s | 6/11 | 10% | v>20.1 |
| Brain carcinoma | Adam et al., 2006 | IHC-Fr | mAb HNE5.1 | 0/1 | 0% | n.s. |
|  | Ryan et al., 2010 | IHC-FFPE | 1C1/5D12Ab | 6/59 | 10% | 1% |
| Glioblastoma | Wischhusen et al., 2002 | IHC-Fr | n.s | 5/12 | 42% | n.s. |
| Astrocytoma | Wischhusen et al., 2002 | IHC-Fr | n.s | 3/4 | 75% | n.s. |
| Nasopharyngeal carcinoma | Ryan et al., 2010 | IHC-FFPE | 1C1/5D12Ab | 18/82 | 22% | 1% |
| EBV-Associated NPC Mesothelioma | Agathanggelou et al., 1995 | IHC-Fr | Ki24 | 16/18 | 89% | n.s. |
| Hepatocellular carcinoma | Adam et al., 2006 | IHC-Fr | mAb HNE5.1 | 0/1 | 0% | n.s. |
| Esophagus carcinoma | Hishima et al., 2000 | IHC-Fr | mAb HNE5.1 | 0/5 | 0% | 1% |
| Pancreatic carcinoma | Ryan et al., 2010 | IHC-FFPE | 1C1/5D12Ab | 35/140 | 25% | 1% |

FIG. 4 Cont.

| | | | | | |
|---|---|---|---|---|---|
| Esophagus carcinoma | Adam et al., 2006 | IHC-Fr | mAb HNE5.1 | 0/2 | 0% | n.s. |
| Colon carcinoma | Ryan et al., 2010 | IHC-FFPE | 1C1/5D12Ab | 17/194 | 9% | 1% |
| Breast carcinoma | Adam et al., 2006 | IHC-Fr | mAb HNE5.1 | 0/11 | 0% | n.s. |
| | Ryan et al., 2010 | IHC-FFPE | 1C1/5D12Ab | 5/204 | 2% | 1% |
| Ovarian carcinoma | Aggarwal et al., 2009 | IHC-FFPE | LP-28809 | 10/10 | 100% | 0.1% |
| | Ryan et al., 2010 | IHC-FFPE | 1C1/5D12Ab | 37/241 | 15% | 1% |
| Thyroid carcinoma | Adam et al., 2006 | IHC-Fr | mAb HNE5.1 | 0/1 | 0% | n.s. |
| Lung carcinoma | Hishima et al., 2000 | IHC-Fr | mAb HNE5.1 | 0/17 | 0% | 1% |
| | Adam et al., 2006 | IHC-Fr | mAb HNE5.1 | 1/19 | 5% | n.s. |

| | | | | | |
|---|---|---|---|---|---|
| Adenocarcinoma | Jacobs et al., 2015 | IHC-FFPE | 4B12 | 3/32 | 9% | 10% |
| | Ryan et al., 2010 | IHC-FFPE | 1C1/5D12Ab | 17/172 | 10% | 1% |
| Squamous carcinoma | Jacobs et al., 2015 | IHC-FFPE | 4B12 | 4/15 | 27% | 10% |
| Neuro-Endocrine carcinoma | Jacobs et al., 2015 | IHC-FFPE | 4B12 | 1/1 | 100% | 10% |
| Thymic carcinoma | Hishima et al., 2000 | IHC-Fr | mAb HNE5.1 | 8/27 | 30% | 1% |
| Melanoma | Adam et al., 2006 | IHC-Fr | mAb HNE5.1 | 0/1 | 0% | n.s. |
| | Ryan et al., 2010 | IHC-FFPE | 1C1/5D12Ab | 15/96 | 16% | 1% |

Abbreviations: IHC, immunohistochemistry; FFPE, formalin-fixed paraffin embedded; Fr, frozen; ISH, in situ hybridization; mAB, monoclonal antibody; n.s., not specified; EBV, Epstein-Barr virus; CAEBV, chronic active EBV-infection; NPC, nasopharyngeal carcinoma; v, value.

FIG. 4 Cont.

Table 4 The role of CXCL8-CXCR1/2 pathway in common cancers[42]

The role of CXCL8-CXCR1/2 pathway in common cancers

| cancer Type | Function | Associated factors | Ref. |
|---|---|---|---|
| Breast cancer | Proliferation | Cyclin D1, p27$^{Kip21}$ | [137] |
| | Angiogenesis | MVD | [7,63,66] |
| | Metastasis | Integrin 3β | [137,138] |
| | Chemoresistance | MRP | [10] |
| | CSCs Activation | HER2 | [64,65] |
| Prostate cancer | Proliferation | Cyclin D1, AR, CXCR7, p53 | [23,79,139,140] |
| | Angiogenesis | VEGF | [8,9] |
| | Metastasis | MMP-2/9, E-cadherin | [9,141] |
| | Chemoresistance | src, NF-$_K$B, c-FLIP, Akt | [6,11,142] |
| Lung cancer | Proliferation | EGFR | [25] |
| | Angiogenesis | VEGF, MVD | [88,90,143,144] |
| | Metastasis | PLD,Akt,PKC,MMP-2/9 | [92,93,145,146] |
| Colorectal cancer | Proliferation | EGFR,MAPK | [107,147,148] |
| | Angiogenesis | CD31,MVD | [107,121] |
| | Metastasis | P13K,Akt,Erk, integrin αvβ6 | [108,149,150] |
| | Chemoresistance | NF-$_K$B, Bcl-2, survivin | [151,152] |
| Melanoma | Proliferation | Akt,Erk | [105] |
| | Angiogenesis | MMP-2/9, VEGF | [99,153,154] |
| | Metastasis | MMP-2 | [99] |

MRP,Multidrug resistance protein; AR, androgen receptor; Bcl-2, B-cell CLL/lymphoma 2.

FIG. 5

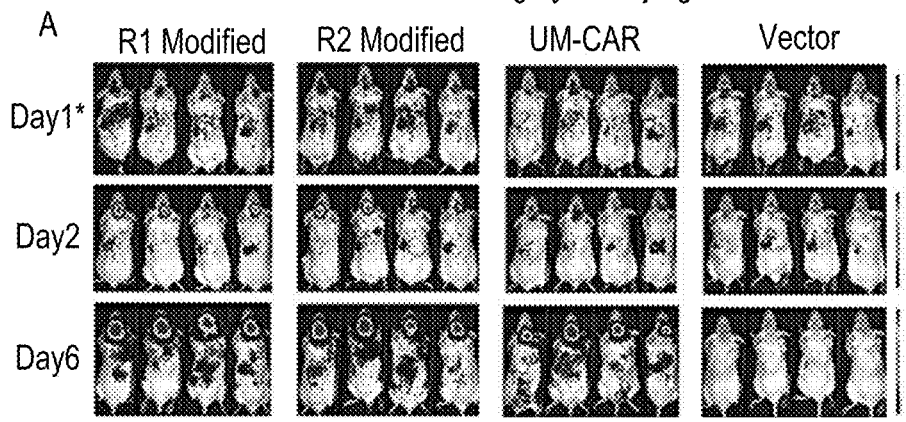
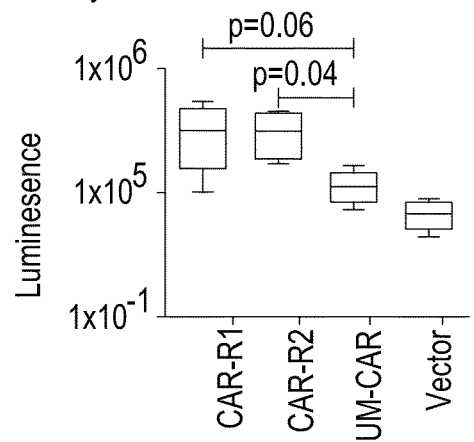
FIG. 13

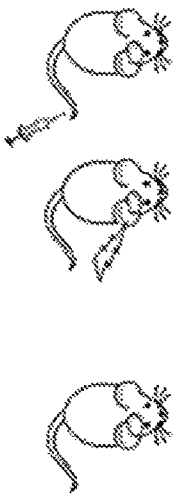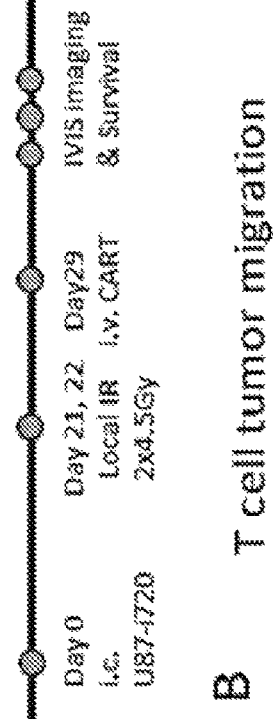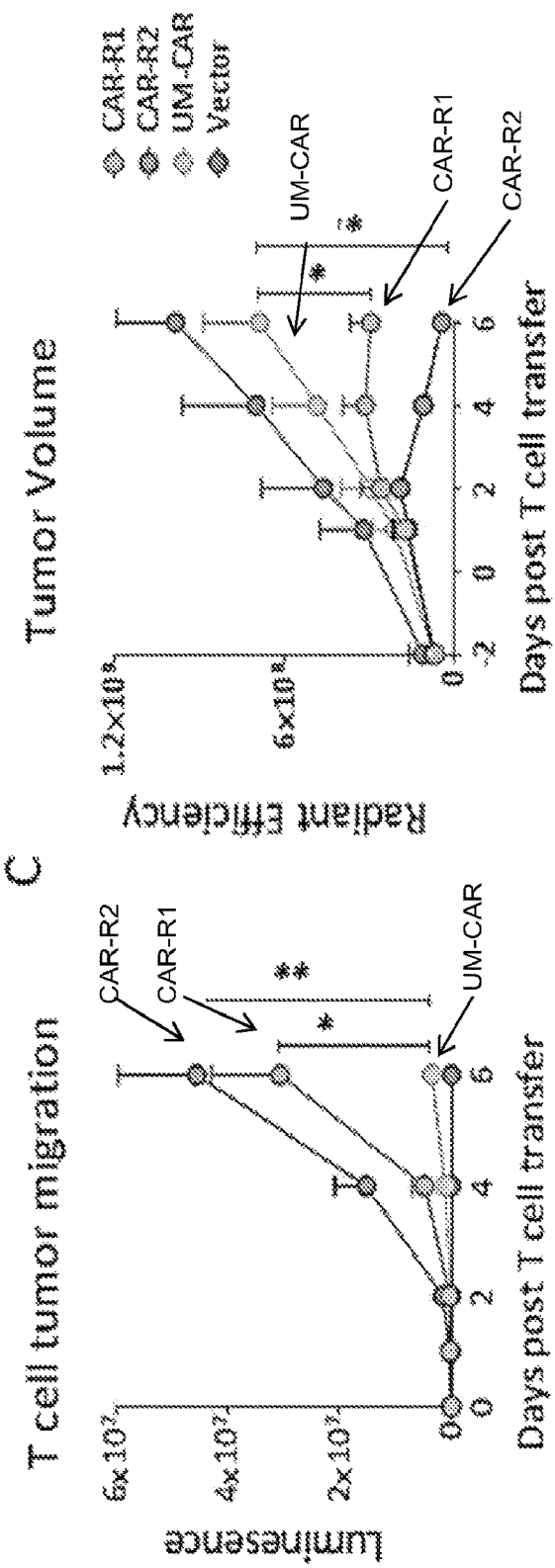
FIG. 17

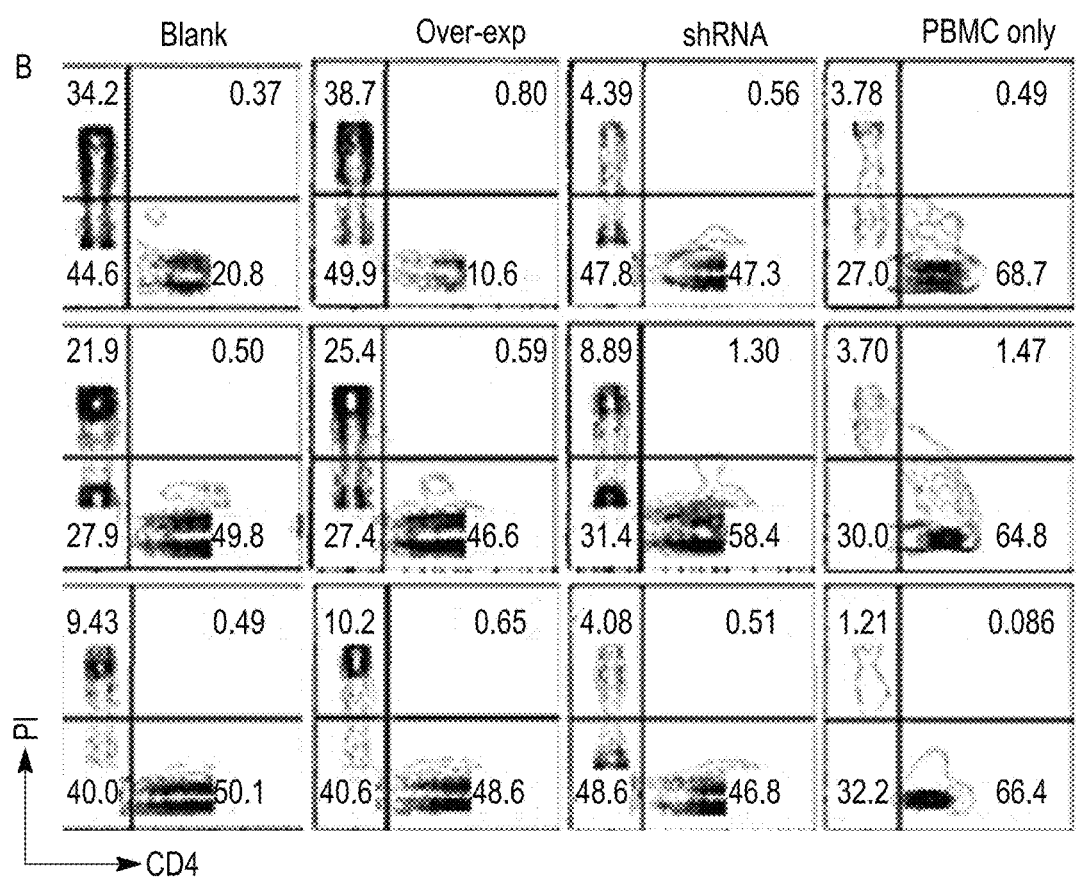
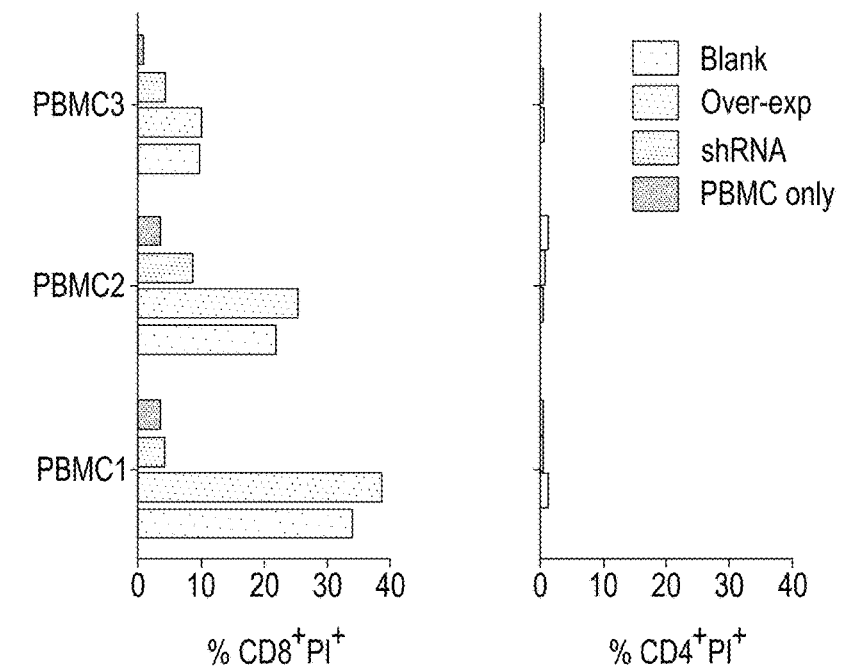
FIG. 21 Cont.

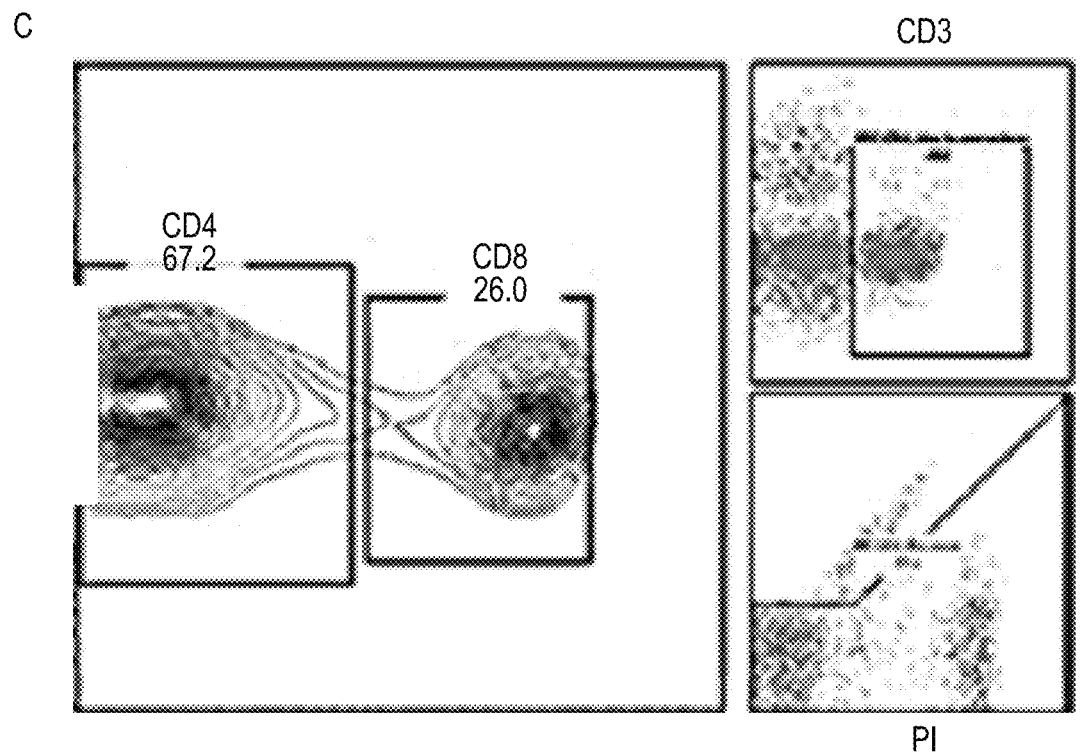
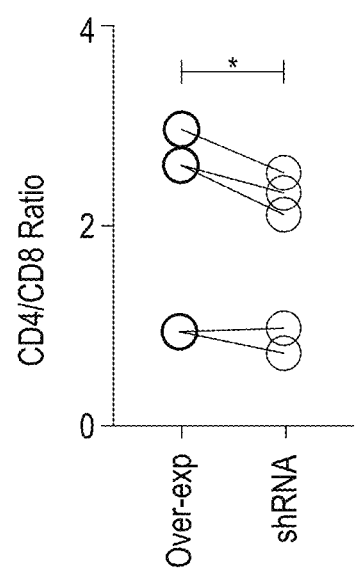
FIG. 21 Cont.

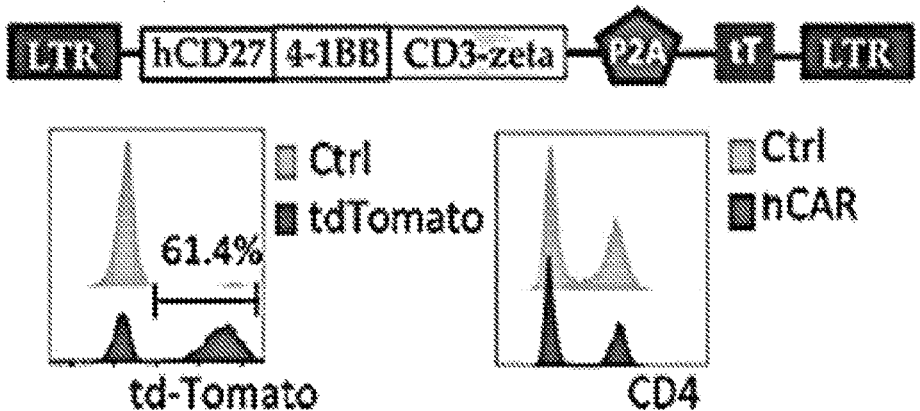
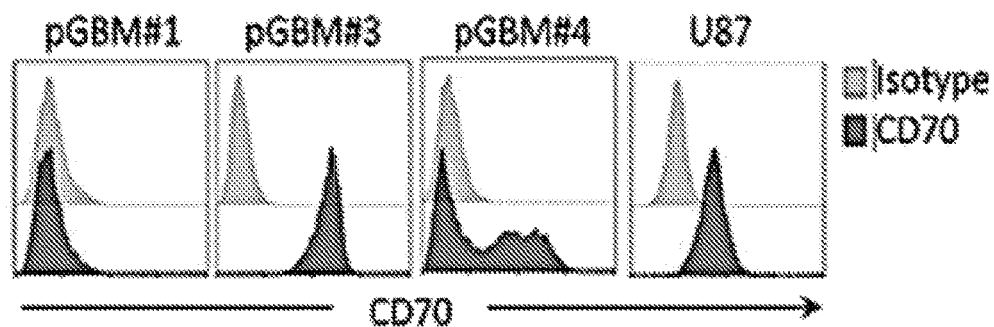
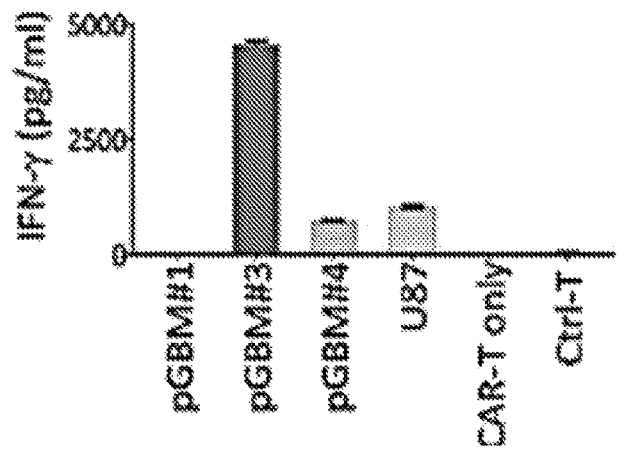
*FIG.22*

FIG. 28 Patients Demographic and Clinical Characteristics

| Characteristics | Primary LGG (n=41) | | Primary GBM (n=46) | | Primary-Recurrent GBM (n=7) | |
|---|---|---|---|---|---|---|
| | No | % | No | % | No | % |
| Age at the first surgery | | | | | | |
| Mean | 44.9 | | 45.6 | | 50.1 | |
| Standard deviation | 14.1 | | 14.4 | | 9.7 | |
| Range | 17-72 | | 19-80 | | 35-66 | |
| Gender | | | | | | |
| Male | 15 | 36.6 | 28 | 60.9 | 4 | 57.1 |
| Female | 26 | 63.4 | 18 | 39.1 | 3 | 42.9 |
| Race/ethnicity | | | | | | |
| Han | 39 | 95.1 | 44 | 95.7 | 7 | 100 |
| Others | 2 | 4.9 | 2 | 4.3 | 0 | 0 |
| Tumor type | | | | | | |
| Astrocytoma | 34 | 82.9 | 0 | 0 | 0 | 0 |
| Oligoastrocytomas | 7 | 17.1 | 0 | 0 | 0 | 0 |
| Glioblastoma | 0 | 0 | 46 | 100 | 7 | 100 |
| Tumor location | | | | | | |
| Frontal | 12 | 29.3 | 13 | 28.3 | 3 | 42.9 |
| Temporal | 16 | 39.0 | 12 | 26.1 | 2 | 28.6 |
| Parietal | 3 | 7.3 | 2 | 4.3 | 1 | 14.3 |
| Occipital | 2 | 4.9 | 1 | 2.2 | 0 | 0 |
| Mixed | 7 | 17.1 | 17 | 37.0 | 1 | 14.3 |
| Other | 1 | 2.4 | 1 | 2.2 | 0 | 0 |
| Tumor lateralization | | | | | | |
| Left | 18 | 43.9 | | 50 | 3 | 42.9 |
| Right | 22 | 53.7 | | 47.8 | 4 | 57.1 |
| Middle | 1 | 2.4 | | 2.2 | 0 | 0 |
| Main symptom of the first diagnosis | | | | | | |
| High cranial pressure | 16 | 39.0 | | 56.5 | 6 | 85.7 |
| Tumor bleeding | 2 | 4.9 | | 6.5 | 0 | 0 |
| Dysuria | 9 | 22.0 | | 19.6 | 0 | 0 |
| Epilepsy | 3 | 7.3 | | 10.9 | 0 | 0 |
| Others | 4 | 9.8 | | 4.3 | 0 | 0 |
| Asymptomatic | 7 | 17.1 | | 2.2 | 1 | 14.3 |
| Neurosurgical intervention | | | | | | |
| Resection | 37 | 90.2 | | 95.7 | 7 | 100 |
| Biopsy | 4 | 9.8 | | 4.3 | 0 | 0 |
| Lost to follow up | 12 | 29.3 | | 34.8 | 0 | 0 |

SEQUENCE LISTING

```
<160> NUMBER OF SEQ ID NOS: 8

<210> SEQ ID NO 1
<211> LENGTH: 2297
<212> TYPE: DNA
<213> ORGANISM: Homo sapiens
<220> FEATURE:
<221> NAME/KEY: misc_feature
<223> OTHER INFORMATION: Human CD70CAR-CXCR1
<220> FEATURE:
<221> NAME/KEY: misc_feature
<222> LOCATION: (3)..(1103)
<223> OTHER INFORMATION: Extracellular CD27+Intracellular 41bb+CD3zeta;
      codon optimized
<220> FEATURE:
<221> NAME/KEY: misc_feature
<222> LOCATION: (113)..(1232)
<223> OTHER INFORMATION: Furin, V5 peptide, P2A ribosomal skip peptide
<220> FEATURE:
<221> NAME/KEY: misc_feature
<222> LOCATION: (1239)..(2291)
<223> OTHER INFORMATION: Human CXCR1; codon optimized

<400> SEQUENCE: 1
ccatggcaag accccacccc tggtggctgt gtgtgctggg cacactggtc ggactgagcg      60 ccaccctgc ccctaagagc tgccccgaga gacactactg ggctcagggc aagctgtgct     120
gccagatgtg cgagcccggc accttcctgg tgaaagactg cgaccagcac cggaaggccg     180
cccagtgcga tccttgcatc cccggcgtgt ccttcagccc cgaccaccac accagacccc     240
actgcgagag ctgccggcat tgcaactctg gcctgctggt ccgcaactgc accatcaccg     300
ccaacgccga gtgcgcctgc agaaacggct ggcagtgccg ggacaaagaa tgcaccgagt     360
gcgaccctct gcccaacccc agcctgaccg ccagaagcag ccaggctctg agccctcacc     420
ctcagcccac ccatctgccc tacgtgtccg agatgctgga agcccggaca gccggccaca     480
tgcagaccct ggccgacttc agacagctgc ccgccagaac cctgagcacc cactggcctc     540
cccagcggag cctgtgcagc agcgacttca tccggatcct ggtgatcttc agcggcatgt     600
tcctggtgtt caccctggct ggcgccctgt tcctgcacaa gcggggcaga aagaagctgc     660
tgtacatctt caagcagccc ttcatgcggc ccgtgcagac cacccaggaa gaggacggct     720
gcagctgccg gttccccgag gaagaggaag gcggctgcga gctgagagtg aagttcagca     780
gaagcgccga cgcccctgcc taccagcagg gccagaacca gctgtacaac gagctgaacc     840
```

```
tgggcagacg ggaagagtac gacgtgctgg acaagcggag aggccgggac cctgagatgg    900
gcggcaagcc ccagaggcgg aagaaccctc aggaaggcct gtataacgaa ctgcagaaag    960
acaagatggc cgaggcctac agcgagatcg gcatgaaggg cgagcggcgg agaggcaagg   1020
gccacgatgg cctgtaccag ggcctgagca ccgccaccaa ggacacctac gacgccctgc   1080
acatgcaggc tctgcctcca agattaatta ccgtgccaa gcgaggtaag cctatcccta    1140
accctctcct cggtctcgat tctacgggat ccggagccac gaacttctct ctgttaaagc   1200
aagcaggaga cgtggaagaa accccggtc ctttcgaaat gagcaacatc acggacccgc    1260
agatgtggga cttcgacgac ctgaacttca ccggcatgcc tccagccgac gaggattaca   1320
gcccttgcat gctggaaacc gagacactga acaaatacgt ggtcatcatt gcctacgctc   1380
tggtgttcct gctgagcctg ctgggcaata gcctggtcat gctggtcatc ctgtacagca   1440
gagtgggcag atccgtgacc gacgtgtacc tgctgaatct ggccctggcc gatctgctgt   1500
ttgccctgac actgcctatt ggggccgcca gcaaagtgaa cggctggatc ttcggcacct   1560
tcctgtgcaa ggtggtgtct ctgctgaaag aagtgaactt ctacagcggc atcctgctgc   1620
tggcctgcat cagcgttgac agatacctgg ccatcgtgca cgccaccaga acactgaccc   1680
agaagagaca cctggtcaag ttcgtgtgcc tcggctgttg gggcctgagc atgaatctgt   1740
ctctgccatt cttcctgttc cggcaggcct accatcctaa caacagcagc cctgtgtgct   1800
acgaggtgct gggaaacgat acagccaagt ggcggatggt gctgcggatc ctgcctcaca   1860
ccttcggctt tatcgtgccc ctgttcgtga tgctgttctg ctacggcttc acctgcgga   1920
ccctgttcaa agcccacatg ggccagaaac accgggccat gagagtgatc tttgccgtgg   1980
tgctgatctt cctgctgtgc tggctgcct acaacctggt gctgcttgcc gacacactga   2040
tgcggaccca agtgatccaa gagagctgcg agcggcggaa caatatcggc agagccctgg   2100
atgctaccga gatcctgggc ttcctgcaca gctgtctgaa ccccatcatc tacgccttca   2160
tcggccagaa cttccggcac ggctttctga gattctggc catgcacggc ctggtgtcca   2220
aagagttcct ggccagacac agagtgacca gctacaccag cagctccgtg aacgtgtcca   2280
gcaacctctg agtcgac                                                 2297
```

<210> SEQ ID NO 2
<211> LENGTH: 2327
<212> TYPE: DNA
<213> ORGANISM: Homo sapiens
<220> FEATURE:
<221> NAME/KEY: misc_feature
<223> OTHER INFORMATION: CD70CAR-CXCR2
<220> FEATURE:
<221> NAME/KEY: misc_feature
<222> LOCATION: (3)..(1103)
<223> OTHER INFORMATION: Extracellular CD27+Intracellular 41bb+CD3zeta;
      codon optimized
<220> FEATURE:
<221> NAME/KEY: misc_feature
<222> LOCATION: (1113)..(1232)
<223> OTHER INFORMATION: Furin, V5 peptide, P2A ribosomal skip peptide
<220> FEATURE:
<221> NAME/KEY: misc_feature
<222> LOCATION: (1239)..(2321)
<223> OTHER INFORMATION: Human CXCR2; codon optimized

<400> SEQUENCE: 2

```
ccatggcaag accccacccc tggtggctgt gtgtgctggg cacactggtc ggactgagcg     60
ccaccccctgc ccctaagagc tgccccgaga cacactactg ggctcagggc aagctgtgct    120
```

-continued

| | |
|---|---|
| gccagatgtg cgagcccggc accttcctgg tgaaagactg cgaccagcac cggaaggccg | 180 |
| cccagtgcga tccttgcatc cccggcgtgt ccttcagccc cgaccaccac accagacccc | 240 |
| actgcgagag ctgccggcat tgcaactctg gcctgctggt ccgcaactgc accatcaccg | 300 |
| ccaacgccga gtgcgcctgc agaaacggct ggcagtgccg ggacaaagaa tgcaccgagt | 360 |
| gcgaccctct gcccaacccc agcctgaccg ccagaagcag ccaggctctg agccctcacc | 420 |
| ctcagcccac ccatctgccc tacgtgtccg agatgctgga agcccggaca gccgccaca | 480 |
| tgcagaccct ggccgacttc agacagctgc cgccagaac cctgagcacc cactggcctc | 540 |
| cccagcggag cctgtgcagc agcgacttca tccggatcct ggtgatcttc agcggcatgt | 600 |
| tcctggtgtt caccctggct ggcgccctgt tcctgcacaa gcggggcaga agaagctgc | 660 |
| tgtacatctt caagcagccc ttcatgcggc ccgtgcagac cacccaggaa gaggacggct | 720 |
| gcagctgccg gttccccgag aagaggaag gcggctgcga gctgagagtg aagttcagca | 780 |
| gaagcgccga cgcccctgcc taccagcagg gccagaacca gctgtacaac gagctgaacc | 840 |
| tgggcagacg ggaagagtac gacgtgctgg acaagcggag aggccgggac cctgagatgg | 900 |
| gcggcaagcc ccagaggcgg aagaaccctc aggaaggcct gtataacgaa ctgcagaaag | 960 |
| acaagatggc cgaggcctac agcgagatcg gcatgaaggg cgagcggcgg agaggcaagg | 1020 |
| gccacgatgg cctgtaccag ggcctgagca ccgccaccaa ggacacctac gacgccctgc | 1080 |
| acatgcaggc tctgcctcca agattaatta ccgtgccaa gcgaggtaag cctatcccta | 1140 |
| accctctcct cggtctcgat tctacgggat ccggagccac gaacttctct ctgttaaagc | 1200 |
| aagcaggaga cgtggaagaa aacccccggtc ctttcgaaat ggaagatttc aacatggaaa | 1260 |
| gcgacagctt cgaggacttc tggaaaggcg aggacctgag caactacagc tacagctcta | 1320 |
| ccctgcctcc tttcctgctg gatgccgctc cttgtgaacc cgagagcctg gaaatcaaca | 1380 |
| agtacttcgt ggtcattatc tacgccctgg tgttcctgct gagcctgctg gcaatagcc | 1440 |
| tggtcatgct ggtcatcctg tacagcagag tgggcagatc cgtgaccgac gtgtacctgc | 1500 |
| tgaatctggc cctggccgat ctgctgtttg ccctgacact gcctatttgg gccgccagca | 1560 |
| aagtgaacgg ctggatcttc ggcaccttcc tgtgcaaggt ggtgtctctg ctgaaagaag | 1620 |
| tgaacttcta ctccggcatc ctgctgctgg cctgcatcag cgttgacaga tacctggcca | 1680 |
| tcgtgcacgc caccagaaca ctgacccaga agcctacct ggtcaagttc atctgcctga | 1740 |
| gcatctgggg actgtccctg ctgcttgctc tgcctgtgct gctgtttcgg agaaccgtgt | 1800 |
| acagctccaa cgtgtcccct gcctgctacg aggacatggg caacaacacc gccaactggc | 1860 |
| ggatgctgct gagaatcctg cctcagagct tcggcttcat cgtgcccctg ctgatcatgc | 1920 |
| tgttctgcta cggcttcacc ctgcggaccc tgttcaaagc ccacatgggc cagaaacacc | 1980 |
| gggccatgag agtgatcttt gccgtggtgc tgatcttcct gctgtgctgg ctgccctaca | 2040 |
| acctggtgct tctggccgac acactgatgc ggacccaagt gatccaagag acatgcgagc | 2100 |
| ggcggaacca catcgacaga gccctggatg ccacagagat cctgggaatc ctgcacagct | 2160 |
| gcctgaatcc tctgatctac gccttcatcg acagaagtt ccggcacggc ctgctgaaga | 2220 |
| ttctggccat ccacgcctg atcagcaagg acagcctgcc taaggacagc agacctagct | 2280 |
| ttgtgggcag cagcagcggc cacacaagca ccacactttg agtcgac | 2327 |

<210> SEQ ID NO 3
<211> LENGTH: 1964
<212> TYPE: DNA
<213> ORGANISM: Homo sapiens

```
<220> FEATURE:
<221> NAME/KEY: misc_feature
<223> OTHER INFORMATION: Human CD70CAR-EGFP
<220> FEATURE:
<221> NAME/KEY: misc_feature
<222> LOCATION: (3)..(1103)
<223> OTHER INFORMATION: Extracellular CD27+Intracellular 41bb+CD3zeta;
      codon optimized
<220> FEATURE:
<221> NAME/KEY: misc_feature
<222> LOCATION: (1113)..(1232)
<223> OTHER INFORMATION: Furin, V5 peptide, P2A ribosomal skip peptide
<220> FEATURE:
<221> NAME/KEY: misc_feature
<222> LOCATION: (1239)..(1958)
<223> OTHER INFORMATION: EGFP; codon optimized

<400> SEQUENCE: 3
ccatggcaag accccacccc tggtggctgt gtgtgctggg cacactggtc ggactgagcg      60
ccaccctgc ccctaagagc tgccccgaga cactactg ggctcagggc aagctgtgct       120
gccagatgtg cgagcccggc accttcctgg tgaaagactg cgaccagcac cggaaggccg     180
cccagtgcga tccttgcatc cccggcgtgt ccttcagccc cgaccaccac accagacccc     240
actgcgagag ctgccggcat tgcaactctg gcctgctggt ccgcaactgc accatcaccg     300
ccaacgccga gtgcgcctgc agaaacggct ggcagtgccg ggacaaagaa tgcaccgagt     360
gcgaccctct gcccaacccc agcctgaccc cagaagcag ccaggctctg agccctcacc      420
ctcagcccac ccatctgccc tacgtgtccg agatgctgga agcccggaca gccggccaca     480
tgcagaccct ggccgacttc agacagctgc ccgccagaac cctgagcacc cactggcctc     540
cccagcggag cctgtgcagc agcgacttca tccggatcct ggtgatcttc agcggcatgt     600
tcctggtgtt caccctggct ggcgcccgtt cctgcacaa gcggggcaga aagaagctgc      660
tgtacatctt caagcagccc ttcatgcggc ccgtgcagac cacccaggaa gaggacggct     720
gcagctgccg gttccccgag gaaggagaag gcggctgcga gctgagagtg aagttcagca     780
gaagcgccga cgcccctgcc taccagcagg gccagaacca gctgtacaac gagctgaacc     840
tgggcagacg ggaagagtac gacgtgctgg acaagcggag aggccgggac cctgagatgg     900
gcggcaagcc ccagaggcgg aagaaccctc aggaaggcct gtataacgaa ctgcagaaag     960
acaagatggc cgaggcctac agcgagatcg gcatgaaggg cgagcggcgg agaggcaagg     1020
gccacgatgg cctgtaccag ggcctgagca ccgccaccaa ggacacctac gacgccctgc     1080
acatgcaggc tctgcctcca agattaatta accgtgccaa gcgaggtaag cctatcccta     1140
accctctcct cggtctcgat tctacgggat ccggagccac gaacttctct ctgttaaagc     1200
aagcaggaga cgtggaagaa aaccccggtc ctttcgaaat ggtgagcaag ggagaggagc     1260
tgttcaccgg ggtggtgccc atcctggtcg agctggacgg cgacgtaaac ggccacaagt     1320
tcagcgtgtc cggcgagggc gagggcgatg ccacctacgg caagctgacc ctgaagttca     1380
tctgcaccac cggcaagctg cccgtgccct ggcccaccct cgtgaccacc ctgacctacg     1440
gcgtgcagtg cttcagccgc taccccgacc acatgaagca gcacgacttc ttcaagtccg     1500
ccatgcccga aggctacgtc caggagcgca ccatcttctt caaggacgac ggcaactaca     1560
agacccgcgc cgaggtgaag ttcgagggcg acaccctggt gaaccgcatc gagctgaagg     1620
gcatcgactt caaggaggac ggcaacatcc tggggcacaa gctggagtac aactacaaca     1680
gccacaacgt ctatatcatg gccgacaagc agaagaacgg catcaaggtg aacttcaaga     1740
tccgccacaa catcgaggac ggcagcgtgc agctcgccga ccactaccag cagaacaccc     1800
```

| | |
|---|---|
| ccatcggcga cggccccgtg ctgctgcccg acaaccacta cctgagcacc cagtccgccc | 1860 |
| tgagcaaaga ccccaacgag aagcgcgatc acatggtcct gctggagttc gtgaccgccg | 1920 |
| ccgggatcac tctcggcatg gatgagctgt acaagtaggt cgac | 1964 |

<210> SEQ ID NO 4
<211> LENGTH: 953
<212> TYPE: DNA
<213> ORGANISM: Homo sapiens
<220> FEATURE:
<221> NAME/KEY: misc_feature
<223> OTHER INFORMATION: Human CXCR1

<400> SEQUENCE: 4

| | |
|---|---|
| ccgagacact gaacaaatac gtggtcatca ttgcctacgc tctggtgttc ctgctgagcc | 60 |
| tgctgggcaa tagcctggtc atgctggtca tcctgtacag cagagtgggc agatccgtga | 120 |
| ccgacgtgta cctgctgaat ctggccctgg ccgatctgct gtttgccctg acactgccta | 180 |
| tttgggccgc cagcaaagtg aacgctgga tcttcggcac cttcctgtgc aaggtggtgt | 240 |
| ctctgctgaa agaagtgaac ttctacagcg gcatcctgct gctggcctgc atcagcgttg | 300 |
| acagatacct ggccatcgtg cacgccacca gaacactgac ccagaagaga cacctggtca | 360 |
| agttcgtgtg cctcggctgt tggggcctga gcatgaatct gtctctgcca ttcttcctgt | 420 |
| tccggcaggc ctaccatcct aacaacagca gccctgtgtg ctacgaggtg ctgggaaacg | 480 |
| atacagccaa gtggcggatg gtgctgcgga tcctgcctca caccttcggc tttatcgtgc | 540 |
| ccctgttcgt gatgctgttc tgctacggct tcacccctgcg gaccctgttc aaagcccaca | 600 |
| tgggccagaa caccgggcc atgagagtga tctttgccgt ggtgctgatc ttcctgctgt | 660 |
| gctggctgcc ctacaacctg gtgctgcttg ccgacacact gatgcggacc caagtgatcc | 720 |
| aagagagctg cgagcggcgg aacaatatcg gcagagccct ggatgctacc gagatcctgg | 780 |
| gcttcctgca cagctgtctg aaccccatca tctacgcctt catcggccag aacttccggc | 840 |
| acggcttcct gaagattctg gccatgcacg gcctggtgtc caaagagttc ctggccagac | 900 |
| acagagtgac cagctacacc agcagctccg tgaacgtgtc cagcaacctc tga | 953 |

<210> SEQ ID NO 5
<211> LENGTH: 983
<212> TYPE: DNA
<213> ORGANISM: Homo sapiens
<220> FEATURE:
<221> NAME/KEY: misc_feature
<223> OTHER INFORMATION: Human CXCR2

<400> SEQUENCE: 5

| | |
|---|---|
| tggatgccgc tccttgtgaa cccgagagcc tggaaatcaa caagtacttc gtggtcatta | 60 |
| tctacgccct ggtgttcctg ctgagcctgc tgggcaatag cctggtcatg ctggtcatcc | 120 |
| tgtacagcag agtgggcaga tccgtgaccg acgtgtacct gctgaatctg ccctggccg | 180 |
| atctgctgtt tgccctgaca ctgcctattt gggccgccag caaagtgaac ggctggatct | 240 |
| tcggcacctt cctgtgcaag gtggtgtctc tgctgaaaga agtgaacttc tactccggca | 300 |
| tcctgctgct ggcctgcatc agcgttgaca gatacctggc catcgtgcac gccaccagaa | 360 |
| cactgaccca gaagcgctac ctggtcaagt tcatctgcct gagcatctgg ggactgtccc | 420 |
| tgctgcttgc tctgcctgtg ctgctgtttc ggagaaccgt gtacagctcc aacgtgtccc | 480 |
| ctgcctgcta cgaggacatg ggcaacaaca ccgccaactg gcggatgctg ctgagaatcc | 540 |
| tgcctcagag cttcggcttc atcgtgcccc tgctgatcat gctgttctgc tacggcttca | 600 |

```
cccctgcggac cctgttcaaa gcccacatgg gccagaaaca ccgggccatg agagtgatct    660
ttgccgtggt gctgatcttc ctgctgtgct ggctgcccta caacctggtg cttctggccg    720
acacactgat gcggacccaa gtgatccaag agacatgcga gcggcggaac cacatcgaca    780
gagccctgga tgccacagag atcctgggaa tcctgcacag ctgcctgaat cctctgatct    840
acgccttcat cggacagaag ttccggcacg gcctgctgaa gattctggcc atccacggcc    900
tgatcagcaa ggacagcctg cctaaggaca gcagacctag ctttgtgggc agcagcagcg    960
gccacacaag caccacactt tga                                            983

<210> SEQ ID NO 6
<211> LENGTH: 1100
<212> TYPE: DNA
<213> ORGANISM: Homo sapiens
<220> FEATURE:
<221> NAME/KEY: misc_feature
<223> OTHER INFORMATION: Human CD70 CAR

<400> SEQUENCE: 6
tggcaagacc ccacccctgg tggctgtgtg tgctgggcac actggtcgga ctgagcgcca     60
cccctgcccc taagagctgc cccgagagac actactgggc tcagggcaag ctgtgctgcc    120
agatgtgcga gcccggcacc ttcctggtga agactgcga ccagcaccgg aaggccgccc     180
agtgcgatcc ttgcatcccc ggcgtgtcct tcagccccga ccaccacacc agccccact     240 gcgagagctg ccggcattgc aactctggcc tgctggtccg caactgcacc atcaccgcca    300
acgccgagtc gcctgcaga aacggctggc agtgccggga caagaatgc accgagtgcg      360 accctctgcc caaccccagc ctgaccgcca gaagcagcca ggctctgagc cctcaccctc    420
agcccaccca tctgccctac gtgtccgaga tgctggaagc ccggacagcc ggccacatgc    480
agaccctggc cgacttcaga cagctgcccg ccagaaccct gagcacccac tggcctcccc    540
agcggagcct gtgcagcagc gacttcatcc ggatcctggt gatcttcagc ggcatgttcc    600
tggtgttcac cctggctggc gccctgttcc tgcacaagcg gggcagaaag aagctgctgt    660
acatcttcaa gcagcccttc atgcggcccg tgcagaccac ccaggaagag acggctgca    720 gctgccggtt ccccgaggaa gaggaaggcg gctgcgagct gagagtgaag ttcagcagaa    780
gcgccgacgc ccctgcctac cagcagggcc agaaccagct gtacaacgag ctgaacctgg    840
gcagacggga agagtacgac gtgctggaca agcggagagg ccgggaccct gagatgggcg    900
gcaagcccca gaggcggaag aaccctcagg aaggcctgta taacgaactg cagaaagaca    960
agatggccga ggcctacagc gagatcggca tgaagggcga gcggcggaga ggcaagggcc   1020
acgatggcct gtaccagggc ctgagcaccg ccaccaagga cacctacgac gccctgcaca   1080
tgcaggctct gcctccaaga                                               1100

<210> SEQ ID NO 7
<211> LENGTH: 120
<212> TYPE: DNA
<213> ORGANISM: Homo sapiens
<220> FEATURE:
<221> NAME/KEY: misc_feature
<223> OTHER INFORMATION: fuV5P2A

<400> SEQUENCE: 7
cgtgccaagc gaggtaagcc tatccctaac cctctcctcg gtctcgattc tacgggatcc     60
ggagccacga acttctctct gttaaagcaa gcaggagacg tggaagaaaa ccccggtcct    120
```

```
<210> SEQ ID NO 8
<211> LENGTH: 620
<212> TYPE: DNA
<213> ORGANISM: Homo sapiens
<220> FEATURE:
<221> NAME/KEY: misc_feature
<223> OTHER INFORMATION: EGFP

<400> SEQUENCE: 8
gcgagggcga tgccacctac ggcaagctga ccctgaagtt catctgcacc accggcaagc      60
tgcccgtgcc ctggcccacc ctcgtgacca ccctgaccta cggcgtgcag tgcttcagcc     120
gctaccccga ccacatgaag cagcacgact tcttcaagtc cgccatgccc gaaggctacg     180
tccaggagcg caccatcttc ttcaaggacg acggcaacta caagacccgc gccgaggtga     240
agttcgaggg cgacaccctg gtgaaccgca tcgagctgaa gggcatcgac ttcaaggagg     300
acggcaacat cctggggcac aagctggagt acaactacaa cagccacaac gtctatatca     360
tggccgacaa gcagaagaac ggcatcaagg tgaacttcaa gatccgccac aacatcgagg     420
acggcagcgt gcagctcgcc gaccactacc agcagaacac ccccatcggc gacggccccg     480
tgctgctgcc cgacaaccac tacctgagca cccagtccgc cctgagcaaa gaccccaacg     540
agaagcgcga tcacatggtc ctgctggagt tcgtgaccgc cgccgggatc actctcggca     600
tggatgagct gtacaagtag                                                 620
```

CHIMERIC ANTIGEN RECEPTOR T-CELLS EXPRESSING INTERLEUKIN-8 RECEPTOR

CROSS-REFERENCE TO RELATED APPLICATIONS

This application claims benefit of priority of U.S. Provisional Patent Application No. 62/555,251 entitled, "IL-8 RECEPTOR MODIFIED CAR AGAINST CD 70 POSITIVE TUMORS," filed Sep. 7, 2017, and U.S. Provisional Patent Application No. 62/570,317 entitled, "AN INTERLEUKIN (IL-8) RECEPTOR COEXPRESSED WITH A CHIMERIC ANTIGEN RECEPTOR (CAR) FOR TREATMENT OF TUMORS," filed Oct. 10, 2017. The entire contents and disclosures of these patent applications are incorporated herein by reference in their entirety.

INCORPORATION BY REFERENCE

This application contains, as a separate part of the disclosure, a sequence listing in computer readable form (Filename: 53374_seqlisting.txt; Size: 16,005 bytes; Created: Sep. 4, 2018), which is incorporated by reference in its entirety.

FIELD OF THE INVENTION

The invention relates to generally to cancer immunotherapy.

BACKGROUND

Glioblastoma, also known as glioblastoma multiforme (GBM), is an aggressive, stubborn brain tumor with low odds of survival for patients. The most common length of survival following diagnosis is 12 to 15 months, with fewer than 3% to 5% of people surviving longer than five years. Typically, treatment involves surgery, after which chemotherapy and radiation therapy are used. Despite maximum treatment, the cancer usually recurs. Cancer immunotherapy represents a promising treatment approach for malignant gliomas but is currently hampered by the limited number of ubiquitously expressed tumor antigens and the profoundly immunosuppressive tumor microenvironment.

SUMMARY

The disclosure provides a nucleic acid comprising a nucleic acid sequence encoding a recombinant protein comprising an interleukin 8 (IL-8) receptor attached to a chimeric antigen receptor (CAR) via a hinge domain, wherein the CAR comprises an antigen binding domain, a transmembrane domain, and a CD3 zeta signaling domain. The nucleic acid sequence of claim 1, wherein the IL-8 receptor is CXCR1 or CXCR2. In various aspects, the hinge domain comprises fuV5P2A and/or the antigen binding domain is an extracellular part of CD27. In various aspects, the nucleic acid comprises a nucleic acid sequence at least 90% identical (e.g., 100 identical) to the sequence of SEQ ID NO: 1 or SEQ ID NO: 2.

The present disclosure further provides a modified T cell comprising a nucleic acid sequence that encodes a recombinant protein comprising an interleukin 8 (IL-8) receptor attached to a chimeric antigen receptor (CAR) via a hinge domain, wherein the CAR comprises an antigen binding domain, a transmembrane domain, and a CD3 zeta signaling domain. In various aspects, modified T cell co-expresses an IL-8 receptor and a CD70 CAR on the cell surface. In various aspects, the IL-8 receptor is CXCR1 or CXCR2 and/or the hinge domain comprises fuV5P2A. In various aspects, the nucleic acid sequence comprises the sequence of SEQ ID NO: 4 or SEQ ID NO: 5 and/or SEQ ID NO: 6. In various aspects, the nucleic acid sequence comprises a nucleic acid sequence at least 90% identical (e.g., 100 identical) to the sequence set forth in SEQ ID NO: 1 or SEQ ID NO: 2.

The present disclosure also provides a method of treating a tumor comprising: administering a modified T cell to a subject in need thereof, wherein the modified T cell comprises a nucleic acid sequence encoding a recombinant protein comprising an interleukin 8 (IL-8) receptor attached to a chimeric antigen receptor (CAR) via a hinge domain, wherein the CAR comprises an antigen binding domain, a transmembrane domain, and a CD3 zeta signaling domain. In various aspects, the modified T cell expresses an IL-8 receptor and a CD70 CAR, wherein the hinge domain comprises a furin cleavage site followed by a V5 peptide tag and has an amino acid sequence set forth in SEQ ID NO: 7. In various aspects, the IL-8 receptor is CXCR1 or CXCR2; optionally, the nucleic acid sequence comprises the sequence of SEQ ID NO: 4 or SEQ ID NO: 5. In various aspects, the nucleic acid sequence comprises the sequence of SEQ ID NO: 6. In various aspects, the modified T cell is administered to the subject in need thereof by intravenous injection or infusion and/or the subject in need thereof has glioma. Use of the modified T cell in the treatment of a tumor, as well as use of the modified T cell in the preparation of a medicament for treating a tumor, as is provided.

BRIEF DESCRIPTION OF THE DRAWINGS

The accompanying drawings, which are incorporated herein and constitute part of this specification, illustrate exemplary embodiments of the disclosure, and, together with the general description given above and the detailed description given below, serve to explain the features of the disclosure.

FIG. 2 is a table (Table 1) showing a summary of CD70 expression from tissue microarray analysis of carcinomas using ICI.[11]

FIG. 3 is a table (Table 2) illustrating cell surface expression of CD27 and CD70 in cancer cell lines according to one embodiment of the present disclosure.[43]

FIG. 4 is a table (Table 3) of an overview of CD70 expression by immunohistochemistry on hematological and solid malignancies.[44]

FIG. 5 is a table (Table 4) showing the role of CXCL8-CXCR1/2 pathway in common cancers.[42]

FIGS. 13(A) and 13(B) illustrate CXCR1 and CXCR2 modified CD70 CAR-T traffic to tumor site earlier than unmodified CD70 CART according to one embodiment of the present disclosure.

FIGS. 17(A)-17(C) illustrate late stage treatment of tumor-bearing mice with IL-8R modified CD70 CAR-T according to one embodiment of the present disclosure.

In FIG. 22(D), the top line corresponds to hCAR-T, and the bottom line corresponds to Ctrl-T.

FIG. 28 is a table summarizing tumor samples and clinicopathological details of the patients described in the Examples.

DETAILED DESCRIPTION

Definitions

Figure 1:
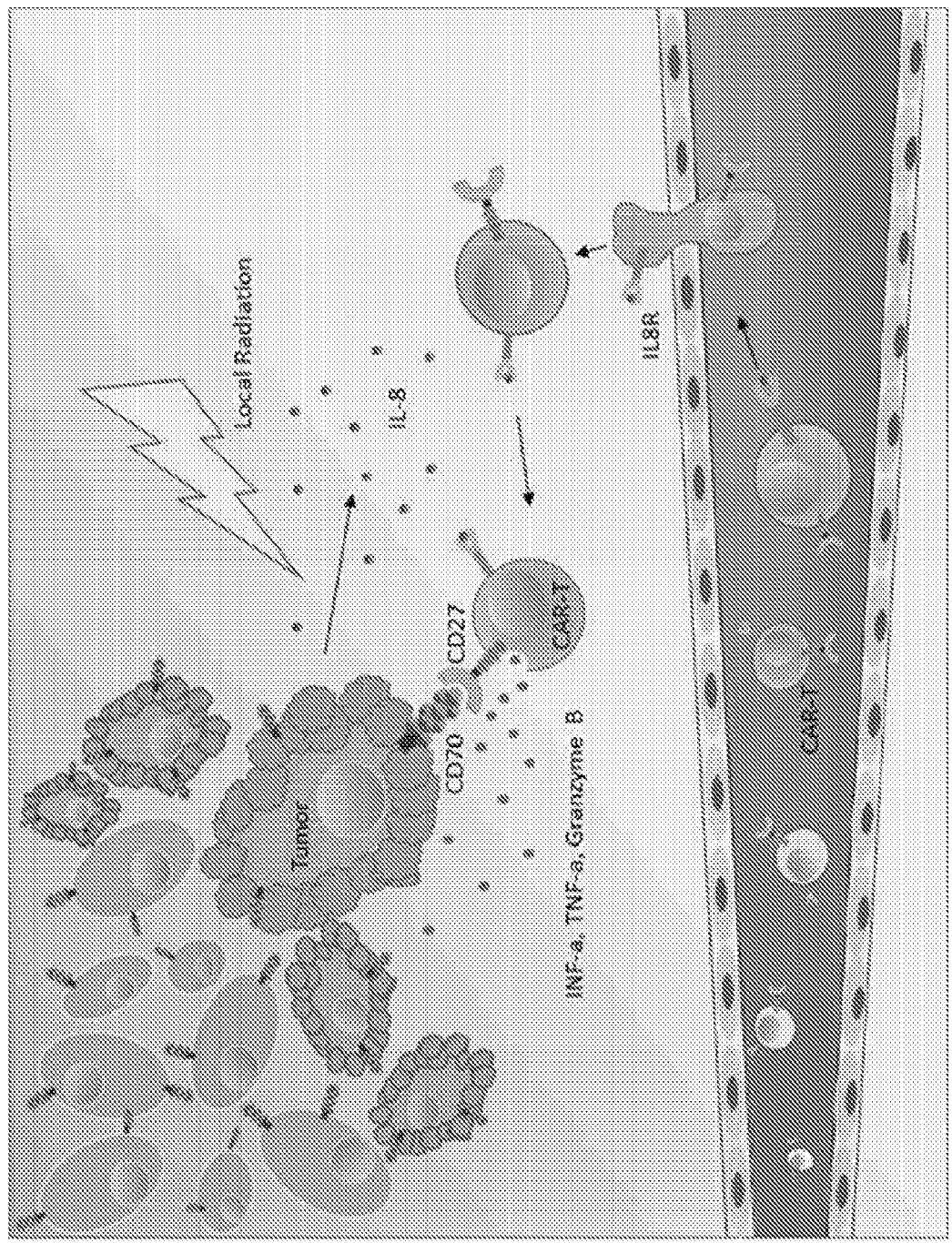
FIG. 1 is a schematic illustration showing a modified CAR T cell that co-expresses interleukin 8 receptor (IL-8R) and a CD70 CAR being used to treat a tumor expressing CD70 according to one embodiment of the present disclosure.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in Gen Bank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an," and "the" include plural referents unless the context clearly dictates otherwise.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, the term "comprising," the term "having," the term "including," and variations of these words are intended to be open-ended and mean that there may be additional elements other than the listed elements.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present disclosure, the term "adjacent" refers to "next to" or "adjoining something else."

For purpose of the present disclosure, the term "adjuvant" or the term "immuno-adjuvant" refers to substances that enhance the production of antibodies without acting as antigens themselves. Adjuvants may be compounds added in a vaccine or therapeutic composition that increase the specific immune response to an antigen. Adjuvants may be added to vaccine to modify the immune response by boosting it such as to give a higher amount of antibodies and a longer lasting protection, thus minimizing the amount of injected foreign material. Adjuvants may also be used to enhance the efficacy of vaccine by helping to subvert the immune response to particular cells type of immune system, for example by activating the T cells instead of antibody-secreting B cells depending on the type of the vaccine.

For purpose of the present disclosure, the term "adoptive cell transfer" refers to the transfer of cells, most commonly immune-derived cells, back into the same patient or into a new recipient host with the goal of transferring the immunologic functionality and characteristics into the new host. For isolation of immune cells for adoptive transfer, blood is drawn into tubes containing anticoagulant and the PBM (buffy coat) cells are isolated, typically by density barrier centrifugation. In T cell-based therapies, adoptive cells are expanded in vitro using cell culture methods relying heavily on the immunomodulatory action of interleukin-2 and returned to the patient in large numbers intravenously in an activated state. The adoptive transfer of autologous immune-promoting or tolerogenic cells (often lymphocytes) to patients is an approach to promote or induce tolerance in autoimmune disease.

For purpose of the present disclosure, the term "adoptive cellular therapy (ACT)" or the term "cellular adoptive immunotherapy" or the term "adoptive immunotherapy" refer to a cell-based therapy with various lymphocytes and antigen-presenting cells. For example, in some situations, the therapy involves collecting T cells from a patient and growing the collected T cells in the laboratory to increase the number of T cells. These T cells are then given back to the same patient or another to help the immune system fight disease.

For purposes of the present disclosure, the term "autologous cells" refers to cells derived from the same individual, involving one individual as both donor and recipient. For example, lymphocytes from are the same person.

For purposes of the present disclosure, the term "ameliorate" and the term "amelioration" to any lessening of severity, delay in onset, slowing of progression, or shortening of duration, whether permanent or temporary, lasting or transient, of the symptoms of a particular disease, disorder or condition by administration of a drug or pharmaceutical composition.

For purposes of the present disclosure, the term "amino acid" refers to the molecules composed of terminal amine and carboxylic acid functional groups with a carbon atom between the terminal amine and carboxylic acid functional groups sometimes containing a side chain functional group attached to the carbon atom (e.g., a methoxy functional group, which forms the amino acid serine). Typically, amino acids are classified as natural and non-natural. Examples of natural amino acids include glycine, alanine, valine, leucine, isoleucine, proline, phenylananine, tyrosine, tryptophan, serine, threonine, cysteine, methionine, asparagine, glutamine, lysine, arginine, histidine, aspartate, and glutamate, among others. Examples of non-natural amino acids include L-3, 4-dihydroxyphenylalanine, 2-aminobutyric acid, dehydralanine, g-carboxyglutamic acid, carnitine, gamma-aminobutyric acid, hydroxyproline, and selenomethionine, among others. In the context of this specification it should be appreciated that the amino acids may be the L-optical isomer or the D-optical isomer.

For purposes of the present disclosure, the term "animal" refers to humans as well as non-human animals. Preferably, the non-human animal is a mammal (e.g., a rodent, a mouse, a rat, a rabbit, a monkey, a dog, a cat, a primate, or a pig). It is also contemplated that the term animal encompasses insects and fish. An animal may be a domesticated animal. An animal may be a transgenic animal. In addition, the term "subject" or "patient" is an "animal" that is treated as discussed below.

For purposes of the present disclosure, the term "antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

For purposes of the present disclosure, the term "bind," the term "binding," or the term "bound" refers to any type of chemical or physical binding, which includes but is not limited to covalent binding, hydrogen binding, electrostatic binding, biological tethers, transmembrane attachment, cell surface attachment, and expression.

For purposes of the present disclosure, the term "biomolecule" refers to the conventional meaning of the term biomolecule, i.e., a molecule produced by or found in living cells, e.g., a protein, a carbohydrate, a lipid, a phospholipid, a nucleic acid, etc.

For purposes of the present disclosure, the term "CAR-T" or the term "CAR T cell" refers to a genetically engineered T cell that produces a chimeric antigen receptor (CAR) on the surface of the cell. The backbone of a CAR-T or CAR T cell is a T cell, which is often collected and separated from a subject, such as a patient, who is going to receive the CAR-T or CAR T cell. A CAR T cell is usually an engineered patient's immune cell used to treat the patient's cancer.

For purposes of the present disclosure, the term "CAR T therapy" refers to treating a disease using CAR T cells. For example, a CAR T therapy may be an immunotherapy utilizing a subject or a patient's own immune cells that are engineered to be able to produce a particular chimeric antigen receptor(s) on their surface. In some situations, T cells are collected from the body of a subject or a patient via apheresis, a process that withdraws blood from the body and removes one or more blood components (such as plasma, platelets or white blood cells). The T cells collected from the body are then genetically engineered to produce a particular chimeric antigen receptor on their surface. After the engineering, the T cells are known as chimeric antigen receptor (CAR) T cells. The CAR T cells are expanded by growing in a laboratory and then administered to the subject or patient, or another subject or patient. The CAR T cells will recognize and kill cancer cells that express a targeted antigen on their surface.

For purposes of the present disclosure, the term "chimeric antigen receptor" and the term "CAR" refers to an engineered receptor that recognize a targeted antigen expressed on the surface of a target cell, such as an antigen expressed on a cancer cell.

For purposes of the present disclosure, the term "co-administration" refers to administration of two or more compositions or compounds to a single subject. Each of the two or more compositions may be administered by the same or different route of administration, at the same time or different time. Co-administration of first therapeutically effective agent and a second therapeutically effective agent, which for example, may be dissolved or intermixed in the same pharmaceutically acceptable carrier, is contemplated.

For purposes of the present disclosure, the term "cognate antigen" refers to an antigen used to immunize an animal and induce it to produce an antiserum.

For purposes of the present disclosure, the term "cognate immune system" refers to a specific and adaptive immune system.

For purposes of the present disclosure, the term "complementary" and the term "complementarity" refer to polynucleotides (e.g., a sequence of nucleotides) related by the base-pairing rules. For example, a DNA sequence 5'-A-G-T-3' is complementary to a DNA sequence 3'-T-C-A-5' or a RNA sequence 3'-U-C-A-5'.

For purposes of the present disclosure, the term "control amount" of a marker refers to any amount or a range of amounts which is to be compared against a test amount of a marker. For example, a control amount of a marker can be the amount of a marker in a person without cancer or neural injury and/or neuronal disorder. A control amount can be either in absolute amount (e.g., μg/ml) or a relative amount (e.g., relative intensity of signals).

For purposes of the present disclosure, the term "correspond" and the term "corresponding" used in the context of a protein sequence refers to an amino acid position(s) of a protein. An amino acid at a position of a protein may be found to be equivalent or corresponding to an amino acid at a position of one or more other protein(s) based on any relevant evidence, such as the primary sequence context of the each amino acid, its position in relation to the N-terminal and C-terminal ends of its respective protein, the structural and functional roles of each amino acid in its respective protein, etc.

For purposes of the present disclosure, the term "diagnosing" refers to identification of the nature of a disease, illness, condition or other problem by examination of the symptoms in an individual.

For purposes of the present disclosure, the term "domain" with respect to a protein refers to a distinct functional or structural unit in the protein. Usually, a protein domain is responsible for a particular function or interaction, contributing to the overall role of a protein. Domains may exist in a variety of biological contexts, where similar domains may be found in proteins with different functions.

For purposes of the present disclosure, the term "dosage" refers to the administering of a specific amount, number, and frequency of doses over a specified period of time. Dosage implies duration. A "dosage regimen" is a treatment plan for administering a drug over a period of time.

For purposes of the present disclosure, the term "dosage form" and the term "unit dose" refer to an individual dose of a pharmaceutical product. Dosage forms may comprise a mixture of active drug components and nondrug components (excipients), along with other non-reusable material that may not be considered either ingredient or packaging.

For purposes of the present disclosure, the term "dose" refers to a specified amount of medication taken at one time.

For purposes of the present disclosure, the term "drug" refers to a material that may have a biological effect on a cell, including but not limited to small organic molecules, inorganic compounds, polymers such as nucleic acids, peptides, saccharides, or other biologic materials, nanoparticles, etc.

For purposes of the present disclosure, the term "effective amount" or "effective dose" or grammatical variations thereof refers to an amount of an agent sufficient to produce one or more desired effects. The effective amount may be determined by a person skilled in the art using the guidance provided herein.

For purposes of the present disclosure, the term "encoding" and the term "encoded," when used in relation to a specified nucleic acid, means, e.g., comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons.

For purposes of the present disclosure, the term "enhance" and the term "enhancing" refer to increasing or prolonging, either in potency or duration, of a desired effect. By way of example, "enhancing" the effect of therapeutic agents singly or in combination refers to the ability to increase or prolong, either in potency, duration and/or magnitude, the effect of the agents on the treatment of a disease, disorder, or condition. When used in a patient, amounts effective for this use will depend on the severity and course of the disease, disorder or condition; previous therapy; the patient's health status and response to therapy; and the judgment of the treating physician.

For purposes of the present disclosure, the term "expression cassette" refers to a part of a vector DNA used for cloning and transformation. In each successful transformation, the expression cassette directs the cell's machinery to make RNA and protein. Some expression cassettes are designed for modular cloning of protein-encoding sequences so that the same cassette may easily be altered to make different proteins. Expression cassettes may also refer to a recombinantly produced nucleic acid molecule that is capable of expressing a genetic sequence in a cell. An expression cassette typically includes a regulatory region such as a promoter (allowing transcription initiation) and a sequence encoding one or more proteins or RNAs. Optionally, the expression cassette may include transcriptional enhancers, non-coding sequences, splicing signals, transcription termination signals, and polyadenylation signals. The sequences controlling the expression of the gene, i.e., its transcription and the translation of the transcription product, are commonly referred to as regulatory unit. Most parts of the regulatory unit are located upstream of coding sequence of the heterologous gene and are operably linked thereto. The expression cassette may also contain a downstream 3' untranslated region comprising a polyadenylation site. The regulatory unit of the disclosure is either directly linked to the gene to be expressed, i.e., transcription unit, or is separated therefrom by intervening DNA such as for example by the 5'-untranslated region of the heterologous gene. Preferably the expression cassette is flanked by one or more suitable restriction sites in order to enable the insertion of the expression cassette into a vector and/or its excision from a vector. Thus, the expression cassette according to the present disclosure may be used for the construction of an expression vector, in particular a mammalian expression vector.

For purposes of the present disclosure, the term "expression vector," otherwise known as an expression construct, refers to a plasmid or virus designed for protein expression in cells. The vector is used to introduce a specific gene into a target cell, and may commandeer the cell's mechanism for protein synthesis to produce the protein encoded by the gene. The plasmid is engineered to contain regulatory sequences that act as enhancer and promoter regions and lead to efficient transcription of the gene carried on the expression vector. The goal of a well-designed expression vector is the production of significant amount of stable messenger RNA, and therefore proteins.

For purposes of the present disclosure, the term "fragment" of a molecule such as a protein or nucleic acid refers to a portion of the amino acid or nucleotide sequence.

For purposes of the present disclosure, the term "gene" refers to a nucleic acid (e.g., DNA or RNA) sequence that comprises coding sequences necessary for the production of an RNA or a polypeptide or its precursor. The term "portion," when used in reference to a gene, refers to fragments of that gene. The fragments may range in size from a few nucleotides to the entire gene sequence minus one nucleotide. Thus, "a nucleotide comprising at least a portion of a gene" may comprise fragments of the gene or the entire gene.

For purposes of the present disclosure, the term "heterologous," when used in relation to a nucleic acid, includes reference to a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

For purposes of the present disclosure, the term "hinge domain" or the term "hinge region" refers to a domain, a region, or a peptide fragment located between other two peptides or proteins in a recombinant protein or fusion protein. For example, in a recombinant protein comprising an IL-8 receptor connected to a CAR, a hinge domain is a peptide fragment located between the IL-8 receptor and the CAR. The hinge domain may comprise a self-cleavage site, such as found in the self-cleaving P2A peptide, which is an example of an hinge domain. Therefore, when a recombinant protein comprising an IL-8 receptor and a CAR is expressed in a cell, the recombinant protein can be cleaved at the site of the hinge domain. As a consequence, the IL-8 receptor and the CAR may be separately expressed on the surface of the cell. In one embodiment, the hinge domain is fuV5P2A, in which a furin cleavage site is followed by a V5 peptide tag introduced upstream of P2A peptide to yield optimal gene expression.[45] Another example of a hinge region is an internal ribosome entry site (IRES).

For purposes of the present disclosure, the term "immunogen" refer to a substance or material (including antigens) that is able to induce an immune response alone or in conjunction with an adjuvant. Both natural and synthetic substances may be immunogens. An immunogen is generally a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozoal fractions.

For purposes of the present disclosure, the term "immunogenicity" refers to the ability to induce humoral and/or cell-mediated immune responses.

For purposes of the present disclosure, the term "immunomodulation" or the term "immuno-regulation" refers to an effect on immune responsiveness. Immunomodulation may be adjustment of the immune response to a desired level, as in immunosuppression or induction of immunologic tolerance.

For purposes of the present disclosure, the term "immunomodulator" refers to an active agent of immunotherapy. Immunomodulators are a diverse array of recombinant, synthetic and natural preparations, such as various cytokines, cellular membrane fractions, etc.

For purposes of the present disclosure, the term "immunogenic" refers to the ability of a substance (antigen) to induce an immune response.

For purposes of the present disclosure, the term "immunotherapy" refers to the treatment of a disease by inducing, enhancing, or suppressing an immune response. Immunotherapies designed to elicit or amplify an immune response are classified as activation immunotherapies, while immunotherapies that reduce or suppress are classified as suppression immunotherapies. The active agents of immunotherapy are collectively called immunomodulators.

For purposes of the present disclosure, the term "individual" refers to an individual mammal, such as a human being.

For purposes of the present disclosure, the term "inhibiting," when used in the context a disorder, means either lessening the likelihood of the disorder's onset, preventing the onset of the disorder entirely, or in some cases, reducing the severity of the disease or disorder after onset. In one embodiment, inhibiting the onset of a disorder means preventing its onset entirely.

For purposes of the present disclosure, the term "introduce," when used in relation to a nucleic acid, refers to inserting a nucleic acid into a cell. Introducing a nucleic acid into a cell may be done by "transfection," "transformation," or "transduction." In some situations, introducing a nucleic acid into a cell may include the incorporation of a nucleic acid into a eukaryotic or prokaryotic cell, where the nucleic acid may be incorporated into the genome of the cell (e.g., chromosome, plasmid, plastid or mitochondrial DNA), converted into an autonomous replicon, or transiently expressed (e.g., transfected mRNA).

For purposes of the present disclosure, the term "isolated," "isolated nucleic acid," or "isolated protein" includes reference to a material, such as a nucleic acid or a protein, which is substantially or essentially free from components which normally accompany or interact with it as found in its naturally occurring environment. The isolated material optionally comprises material not found with the material in its natural environment.

For purposes of the present disclosure, the term "ligand" refers to a substance, such as a small molecule, that forms a complex with a biomolecule to serve a biological purpose. In protein-ligand binding, the ligand is usually a signal-triggering molecule, binding to a site on a target protein. Ligand binding to a receptor protein (receptor) alters the receptor's chemical conformation (three-dimensional shape). The conformational state of a receptor determines its functional state. Ligands include substrates, inhibitors, activators, and neurotransmitters.

For purposes of the present disclosure, the term "linked" refers to a covalent linkage between two polypeptides in a fusion protein. The polypeptides are typically joined via a peptide bond, either directly to each other or via one or more additional amino acids.

For purposes of the present disclosure, the term "linker" refers to short peptide sequences that occur between functional protein domains and link the functional domains together. Linkers designed by researchers are generally classified into three categories according to their structures: flexible linkers, rigid linkers, and in vivo cleavable linkers. A flexible linker is often composed of flexible residues like glycine and serine so that the adjacent protein domains are free to move relative to one another. A linker also may play a role in releasing the free functional domain in vivo (as in in vivo cleavable linkers). Linkers may offer many other advantages for the production of fusion proteins, such as improving biological activity, increasing expression yield, and achieving desirable pharmacokinetic profiles. The composition and length of a linker may be determined in accordance with methods well known in the art and may be tested for efficacy.

For purposes of the present disclosure, the term "nucleic acid" and the term "polynucleotide," as used interchangeably herein, include reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

For purposes of the present disclosure, the term "oligonucleotide," the term "polynucleotide," the term "nucleotide," and the term "nucleic acid" refer to a molecule comprised of two or more deoxyribonucleotides or ribonucleotides, and usually more than ten. The exact size of an oligonucleotide will depend on many factors, which in turn depends on the ultimate function or use of the oligonucleotide. The oligonucleotide may be generated in any manner, including chemical synthesis, DNA replication, reverse transcription, or a combination thereof. When present in a DNA form, the oligonucleotide may be single-stranded (i.e., the sense strand) or double-stranded.

For purposes of the present disclosure, the term "operably linked," the term "operably associated," and the term "functionally linked" are used interchangeably and include reference to a functional relationship between two or more DNA segments. Particularly, "operably linked" refers to a functional linkage between a first nucleic acid sequence, such as a promoter, in a functional relationship with a second nucleic acid sequence, wherein the promoter sequence initiates and mediates transcription of the DNA corresponding to the second sequence. A promoter/enhancer sequence, including any combination of cis-acting transcriptional control elements is operably associated to a coding sequence if the promoter/enhancer sequence affects the transcription or expression of the coding sequence in an appropriate host cell or other expression system. Promoter regulatory sequences that are operably linked to the transcribed gene sequence are physically contiguous to the transcribed sequence. Generally, operably linked means that the nucleic acid sequences being linked are contiguous and, where necessary to join two protein coding regions, contiguous and in the same reading frame.

For purposes of the present disclosure, the term "parenteral route" refers to the administration of a composition, such as a drug in a manner other than through the digestive tract. Parenteral routes include, but are not limited to, routes such as intravenous, intra-arterial, transdermal, intranasal, sub-lingual and intraosseous, etc. For example, intravenous is also known as I.V., which is giving directly into a vein with injection. As the drug directly goes into the systemic circulation, it reaches the site of action resulting in the onset the action.

For purposes of the present disclosure, the term "patient" and the term "subject" refer to an animal, which is the object of treatment, observation or experiment. By way of example only, a subject may be, but is not limited to, a mammal including, but not limited to, a human.

For purposes of the present disclosure, the term "peptide linker" and the term "linker" are interchangeable and refer to short peptide sequences that occur between functional protein domains and link the functional domains together.

For purposes of the present disclosure, the term "percentage of sequence identity" refers to the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For purposes of the present disclosure, the term "pharmaceutically acceptable" refers to a compound or drug approved or approvable by a regulatory agency of a federal or a state government, listed or listable in the U.S. Pharmacopeia or in other generally recognized pharmacopeia for use in mammals, including humans. For example, a "pharmaceutically acceptable diluent, excipient, carrier, or adjuvant" is a diluent, excipient, carrier, or adjuvant which is physiologically acceptable to the subject while retaining the therapeutic properties of the pharmaceutical composition with which it is administered. One exemplary pharmaceutically acceptable carrier is physiological saline. Pharmaceutically acceptable carriers include, but are not limited to saline solutions and buffered solutions. Pharmaceutically acceptable carriers are described for example in Gennaro, Alfonso, Ed., Remington's Pharmaceutical Sciences, 18th Edition 1990. Mack Publishing Co., Easton, Pa., a standard reference text in this field. Pharmaceutical carriers may be selected in accordance with the intended route of administration and the standard pharmaceutical practice.

For purposes of the present disclosure, the term "pharmaceutical composition" refers to a product comprising one or more active ingredients, and one or more other components such as carriers, stabilizers, diluents, dispersing agents, suspending agents, thickening agents, and/or excipients, etc. A pharmaceutical composition includes enough of the active object compound to produce the desired effect upon the progress or condition of diseases and facilitates the administration of the active ingredients to an organism. Multiple techniques of administering the active ingredients exist in the art including, but not limited to: topical, ophthalmic, intraocular, periocular, intravenous, oral, aerosol, parenteral, and administration. By "pharmaceutically acceptable," it is meant the carrier, diluent or excipient must be compatible with the other ingredients of the formulation and not deleterious to the recipient thereof, i.e., the subject.

For purposes of the present disclosure, the term "pharmaceutical formulation" and the term "drug formulation" refer to a mixtures or a structure in which different chemical substances, including the active drug, are combined to form a final medicinal product, such as a solution, an emulsion, a non-conventional product such as semi-solid, liquid, etc. Pharmaceutical formulation is prepared according to a specific procedure, a "formula." The drug formed varies by the route of administration. For example, oral drugs are normally taken as tablet or capsules.

For purposes of the present disclosure, the term "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

For purposes of the present disclosure, the term "polypeptide" and the term "protein" are used interchangeably herein to refer to a polymer of amino acid residues. The terms encompass amino acid polymers in which one or more amino acid residues are artificial chemical mimetic of a corresponding naturally occurring amino acids, as well as to naturally occurring amino acid polymers and non-naturally occurring amino acid polymer. Polypeptides may be modified, e.g., by the addition of carbohydrate residues to form glycoproteins. The terms "polypeptide," "peptide," and "protein" include glycoproteins, as well as non-glycoproteins.

For purposes of the present disclosure, the term "prevent" refers to stop from happening or to make something not happen.

For purposes of the present disclosure, the term "purified" refers to the component in a relatively pure state.

For purposes of the present disclosure, the term "recombinant" refers to a genetic material formed by a genetic recombination process. A "recombinant protein" is made through genetic engineering. A recombinant protein is coded by a DNA sequence created artificially. A recombinant protein is a protein that is coded by a recombinant nucleic acid sequence. A recombinant nucleic acid sequence has a sequence from two or more sources incorporated into a single molecule.

For purposes of the present disclosure, the term "residue," the term "amino acid residue," or the term "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that may function in a similar manner as naturally occurring amino acids.

For purposes of the present disclosure, the term "room temperature" refers to a temperature of from about 20° C. to about 25° C.

For purposes of the present disclosure, the term "sample" is used herein in its broadest sense. A sample comprising polynucleotides, polypeptides, peptides, antibodies, and the like and may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

For purposes of the present disclosure, the term "sequence identity" or the term "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

For purposes of the present disclosure, the term "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein and do not substantially bind in a significant amount to other proteins present in the sample.

Typically, an antigen-binding domain that specifically binds an antigen will have a Kd that is 20-, 50-, 100-, 500-, 1000-, 5,000-, 10,000- or more times greater for a control molecule relative to the target antigen or epitope. Also, specific binding for a particular antigen can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Methods of testing antigen-binding domains for the ability to bind to a target antigen are known in the art and include, e.g., radioimmunoassay (RIA), ELISA, Western blot, immunoprecipitation, surface plasmon resonance (e.g., BIAcore®), and competitive inhibition assays (see, e.g., Janeway et al. (eds.), Immunobiology, 5th Ed., Garland Publishing, New York, N.Y. (2001); U.S. Patent Publication No. 2002/0197266; and U.S. Pat. No. 7,872,106, all of which are hereby incorporated by reference in their entirety and particularly with respect to disclosure of competition assays).

For purposes of the present disclosure, the term "stimulate" and the term "immuno-stimulate" refer to inducing the activation or increasing the activity of any components in an immune system. For example, T cell activation requires at least two signals to become fully activated. The first occurs after engagement of the T cell antigen-specific receptor (TCR) by the antigen-major histocompatibility complex (MHC), and the second by subsequent engagement of co-stimulatory molecules. Once stimulated, the T cells will recognize the antigen or vaccine used during stimulation or activation of the T cells.

For purposes of the present disclosure, the term "subject" refers to an animal, for example, a mammal, such as a mouse, a rat, a human, etc., who is the object of treatment, observation, or experiment. A "donor subject" in the present disclosure refers to a mammal, such as a person, who donates antibodies, cells, or organs. A "recipient subject" in the present disclosure refers to a mammal, such as a person, who receives antibodies, cells, or organs donated by a donor subject or developed in vitro.

For purposes of the present disclosure, the term "target" refers to a living organism or a biological molecule to which some other entity, like a ligand or a drug, is directed and/or binds. For example, "target protein" may a biological molecule, such as a protein or protein complex, a receptor, or a portion of a biological molecule, etc., capable of being bound and regulated by a biologically active composition such as a pharmacologically active drug compound.

For purposes of the present disclosure, the term "therapeutically effective amount" and the term "treatment-effective amount" refers to the amount of a drug, compound or composition that, when administered to a subject for treating a disease or disorder, or at least one of the clinical symptoms of a disease or disorder, is sufficient to affect such treatment of the disease, disorder, or symptom. A "therapeutically effective amount" may vary depending, for example, on the compound, the disease, disorder, and/or symptoms of the disease or disorder, severity of the disease, disorder, and/or symptoms of the disease or disorder, the age, weight, and/or health of the subject to be treated, and the judgment of the prescribing physician. An appropriate amount in any given instance may be readily ascertained by those skilled in the art or capable of determination by routine experimentation.

For purposes of the present disclosure, the term "treating" and the term "treatment," when being used in relating to a disease, disorder, or condition, refers to an approach for obtaining beneficial or desired results, such as clinical results. Beneficial or desired results may include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Treating" or "treatment" also refers to slowing the progression of a condition, inhibiting the disease or disorder, either physically, (e.g., stabilization of a discernible symptom), physiologically, (e.g., stabilization of a physical parameter), or both, and to inhibiting or slowing the progression of at least one physical parameter which may or may not be discernible to the subject. The term "treatment" as used herein also refers to any treatment of a subject, such as a human condition or disease, and includes: (1) inhibiting the disease or condition, i.e., arresting the development or progression of the disease or condition, (2) relieving the disease or condition, i.e., causing the condition to regress, (3) stopping the symptoms of the disease, and/or (4) enhancing the conditions desired.

"Treating" cancer or a tumor does not require a 100% abolition of cancer in the subject. Any decrease in tumor load, tumor burden, or tumor volume; inhibition of tumor cell proliferation; eradication of tumor cells; reverse of immunosuppression in the tumor microenvironment, and the like constitutes a beneficial biological effect in a subject. The progress of the method in treating a tumor (e.g., reducing tumor size or eradicating cancerous cells) can be ascertained using any suitable method, such as those methods currently used in the clinic to track tumor size and cancer progress. Tumor size can be figured using any suitable technique, such as measurement of dimensions or estimation of tumor volume. Tumor size can be determined by tumor visualization using, for example, CT, ultrasound, SPECT, spiral CT, MRI, photographs, and the like. Measurement of tumor size, detection of new tumors, biopsy, surgical downstaging, PET scans, and the like can point to the overall progression (or regression) of cancer in a human. In various aspects, the materials and methods of the disclosure inhibits metastasis; any degree of preventing, suppressing, delaying the onset, or slowing metastasis in the subject is contemplated.

Description

While the present disclosure is susceptible to various modifications and alternative forms, specific embodiment thereof has been shown by way of example in the drawings and will be described in detail below. It should be understood, however that it is not intended to limit the present disclosure to the particular forms disclosed, but on the contrary, the present disclosure is to cover all modifications, equivalents, and alternatives falling within the spirit and the scope of the disclosure.

Despite highly toxic multimodal treatments, the 5-year survival rate is less than 10% for patients with primary glioblastomas (GBMs), necessitating development of new agents that promote survival without illicit effects.[1,2] Cancer immunotherapy represents a promising new treatment paradigm, and patients with malignant gliomas develop immunotherapeutic response against autologous specimens.[3-5] Modification of patient derived T cells with chimeric antigen receptors (CARs) is a uniquely specific and promising approach for ex vivo activation of tumor-specific T cells, but remains limited by the lack of ideal or appropriate targets in solid tumors. Current Chimeric Antigen Receptor (CAR) engineered T cells face challenges when directed towards solid tumors, as localization of T cells to the tumor microenvironment is one of barriers. To date, EGFRvIII,[20] IL13Ra2,[38] HER2,[39] EphA2,[40] and Podoplanin(PDPN)[41] CAR T cells have demonstrated encouraging results in preclinical studies and in several clinical trials for gliomas. However, antigen escape and safety issues have been indicated.

Important features of an ideal tumor immunotherapeutic target include (i) distinct expression patterns over normal cells to avoid off-target effects, (ii) involvement in malignant propagation, and (iii) ubiquitous expression within tumor cells to limit immune escape.

The present disclosure identifies an ideal tumor immunotherapeutic target and provides a novel approach for targeting immunotherapy of cancers and tumors. The disclosure provides a modified T cell comprising a nucleic acid sequence encoding a recombinant protein comprising an interleukin 8 (IL-8) receptor attached to a chimeric antigen receptor (CAR) via a hinge domain. The CAR comprises, e.g., an antigen binding domain, a transmembrane domain, and a CD3 zeta signaling domain. The disclosure further provides a method of treating a tumor, such as a glioma (e.g., any stage of glioma, including glioblastoma), comprising administering to a patient in need thereof the modified CAR T cell in an amount effective to treat the tumor.

Interleukin 8 ((IL8) or chemokine (C-X-C motif) ligand 8, CXCL8)) is a chemokine that binds to its cognate receptors, C-X-C chemokine receptor 1 (CXCR1) and C-X-C chemokine receptor 2 (CXCR2), and is mainly expressed on neutrophils. Studies have suggested that CXCL8 and its cognate receptors, CXCR1 and CXCR2, mediate the initiation and development of various cancers including breast cancer, prostate cancer, lung cancer, colorectal carcinoma and melanoma.[42]

The present disclosure confirms that IL-8 is expressed by glioma. It is believed that IL-8 expressed in glioma induces tumorigenesis and angiogenesis to protect the glioma itself. The highly expressed IL-8 may be utilized to guide IL-8 receptor (CXCR1 and/or CXCR2) modified CAR-T migration to tumor site and eventually enhance anti-tumor efficacy. Further, radiation is a standard care of many cancer types, including glioma. Irradiation (IR) may impact antitumor efficacy of immunotherapy; for example, tumor chemokine secretion may be enhanced by IR. According to the present disclosure, radiation (IR) upregulates the expression and secretion of IL-8 by glioma. The disclosure provides CAR T cells that are manipulated to co-express an IL-8 receptor, e.g., CXCR1 or CXCR2, whose natural expression on T cells are extremely low. Accordingly, the disclosure provides a new approach for effectively recruiting CAR engineered T cells to tumors.

An RNAseq data analysis, involving more than 100 patient samples culled from TOGA, determined that IL-8 is found to be positively correlated with CD70 gene expression upon glioblastoma's molecular subtypes. This result indicates that IL-8 receptor modification is suitable for CD70 CART therapy.

In various aspects, the CAR of the modified T cell comprises an antigen binding domain that binds Cluster of Differentiation 70 (CD70). CD70 is a type II transmembrane protein that represents the only ligand for CD27. CD70 is a glycosylated transmembrane protein of the tumor necrosis factor receptor family.[6,7] CD70-CD27 interactions play an important role in providing co-stimulation during the development of functional lymphocytes; strict control of CD70 expression is required for optimal signaling for immune cell activation.[8,9] While CD70 expression is restricted to highly activated T/B lymphocytes and a small subset of mature dendritic cells; distinct hematologic and solid tumor malignancies, including gliomas, may constitutively overexpress CD70.[9-13] CD70 is not only highly expressed by primary tumors, but also in recurrent tumors, which presents a consistent therapeutic target for primary and recurrent gliomas.

Although CD70 has been demonstrated to play an important role in dendritic cell-induced enhanced T-cell antitumor immunity,[14,15] without adequate T-cell receptor signals provided by tumor cells, the CD27-CD70 interaction may not induce a strong immunological response, and inversely, promote apoptosis[16-18] and dysregulate T cells' function.

CD70 is not detected in peripheral and brain normal tissues but is constitutively overexpressed by isocitrate dehydrogenase (IDH) wild-type primary LGGs and GBMs in the mesenchymal subgroup and recurrent tumors. CD70 expression in malignant gliomas correlates with poor patient survival in these subgroups. CD70 expression in malignant gliomas may link to its direct involvement in glioma chemokine productions and directly facilitate immune suppression by selectively inducing CD8+ T-cell death. CD70 is not only highly expressed by primary tumors, but also in recurrent tumors, which presents a consistent therapeutic target for primary and recurrent gliomas.[37]

Both human and mouse CD70-specific CAR T cells are demonstrated to recognize primary CD70+ GBM tumors in vitro and mediate the regression of established GBM in xenograft and syngeneic models without illicit effect. These results identify a previously uncharacterized and ubiquitously expressed immunosuppressive ligand CD70 in GBMs that also holds potential for serving as a novel CAR target for cancer immunotherapy in gliomas. An RNAseq data analysis, involving more than 100 patient samples culled from TCGA, determined that IL-8 is found to be positively correlated with CD70 gene expression upon glioblastoma's molecular subtypes. This result indicates that IL-8 receptor modification is suitable for CD70 CART therapy.

FIG. 1 illustrates an exemplary approach for targeting immunotherapy of tumors. As shown in FIG. 1, a modified CAR T cell that co-expresses an IL-8R, e.g., CXCR1 or CXCR2, and a CD70 CAR is used to treat a tumor expressing CD70. The IL-8R may be CXCR1 or CXCR2, which will enhance the migration of the modified CAR T towards a tumor cell expressing CD70. A local radiation increases the expression of IL-8 by the irradiated tumor cell. Therefore, treatment with the IL-8R modified CAR T cells may benefit from a prior radiotherapy. An IL-8 receptor modified CAR may be used to facilitate selective targeting of cancer cells by CAR T cells while avoiding off-target effects. While FIG. 1 illustrates various embodiments of the disclosure with respect to CD70-targetted CAR T cells, the disclosure is not so limited; the disclosure contemplates use of alternative antigen binding domains that specifically bind other cancer or tumor antigens. For example, CAR T cells targeting IL-13Ra2, Her2, EGFR (EGFRvIII), EphA2, PDPN, or MUC1 also are suitable for use in the context of the disclosure.

The in vitro chemotaxis studies described herein demonstrate that both CXCR1- and CXCR2-manipulated CAR T cells (e.g., CD70 CAR T cells) show enhanced migration towards the conditioned media collected from irradiated glioma cell culture. For example, CXCR1 modified CD70 CAR-T shows better tumor recognition than non-modified CD70 CAR-T in an IL-8 dependent manner. To evaluate the trafficking capability of IL-8 receptor modified T cell in vivo, Click-Beetle Luciferase was used to detect T cells and label glioma cells with Near-infrared fluorescent protein-iRFP720 to track tumor growth in vivo. IL-8 receptor modified CD70 CAR T cells eliminate glioma in vivo within 6 days. In contrast, CD70 CAR-T without IL-8 receptor modification did not show this potent anti-glioma efficacy. Overall, the IL-8 receptor modified CAR-T shows enhanced trafficking to tumor site in vivo, which lead to an improvement of anti-tumor efficacy.

Briefly speaking, radiation is a standard care for a variety of cancers and tumor types, including glioma. The IL-8 receptor modified CAR T cells of the disclosure elicit an additional benefit of radiation therapy. For example, in various aspects, the subject to be administered the IL-8R-modified CAR T cell is previously treated with radiation. While not wishing to be bound to a particular theory, radiation triggers IL-8 production, which improves the homing and anti-tumor activity of CAR T cells to the target. As such, the disclosure expands radiotherapy's benefit immunotherapy.

The materials and methods of the disclosure may be used to treat any type of cancer or tumor that is responsive to the CAR T cell. In various aspects, the CAR binds CD70. An embodiment exemplified herein comprises an IL-8R-modified CD70 CAR-T used to treat glioma, but it will be appreciated that the construct also may be used to treat other tumors or cancers that express CD70 and IL-8, including leukemia or other blood cancers, and other tumors including kidney, pancreas, larynx or pharynx, melanoma, ovary, lung adenocarcinoma, colon, breast, and other brain tumors, etc. Table 1 in FIG. 2 shows a summary of CD70 expression from tissue microarray analysis of carcinomas using ICI.[11] As shown in FIG. 2 Table 1, CD70 is found in tumors in kidney, pancreas, larynx or pharynx, melanoma, ovary, lung adenocarcinoma, colon, breast, and brain.[11] FIG. 3 is a table (Table 2) illustrating cell surface expression of CD27 and CD70 in cancer cell lines.[43] FIG. 4 is a table (Table 3) of an overview of CD70 expression by immunohistochemistry on hematological and solid malignancies.[44] The disclosure contemplates use of the modified CAR T cell described herein to treat any of the cancers described herein.

For simplicity of illustration, FIG. 1 shows IL-8 receptor modified CAR-T being used to target a tumor expressing CD70. As noted above, the disclosure is not limited to CD70 CAR. According to the present disclosure, an IL-8 receptor may be used to modify any CAR for targeting tumor or cancer cells that express IL-8. FIG. 5 is a table (Table 4) showing the role of CXCL8-CXCR1/2 pathway in common cancers and the factors associated with the CXCL8-CXCR1/2 pathway.[42] The disclosed IL-8 receptor modified CAR T may be used to treat any cancer or tumor that express IL-8, such as those set forth in FIG. 5. For such purpose, any CAR that recognizes a cancer cell expressing IL-8 may be modified with an IL-8 receptor such as CXCR1 or CXCR2.

Since a disclosed IL-8 receptor modified CAR-T may recognize and track a cancer cell expressing IL-8, the IL-8 receptor modified CAR-T may be administered systematically to a subject or patient in need thereof and migrate to a target tumor or a cancer cell that expresses IL-8. A tumor usually has a wall built by cancer cells around the mass of the tumor, which keeps invaders out of the growing mass. The IL-8 receptor modified CAR-T is able to penetrate into the center of a target tumor, such as the center of a glioma, and kill the cancer cells. For example, the IL-8 receptor modified CD70 CAR-T is able to penetrate into the center of a tumor expressing CD70, such the center of a glioma, and kill the cancer cells. Therefore, the IL-8 receptor modified CAR-T may be administered to a patient to treat an inoperative tumor. For example, the IL-8R modified T cell may be administered to a patient suffering from a late stage of cancer who cannot receive a surgery for resection of the tumor. The IL-8 receptor modified CAR-T also may be administered to a patient or a subject who cannot receive a surgery because a tumor is located in a life threatening location, or because the patient or the subject has multiple lesions, or because other reasons that an operation is not an option to the patient or the subject.

Figure 6:
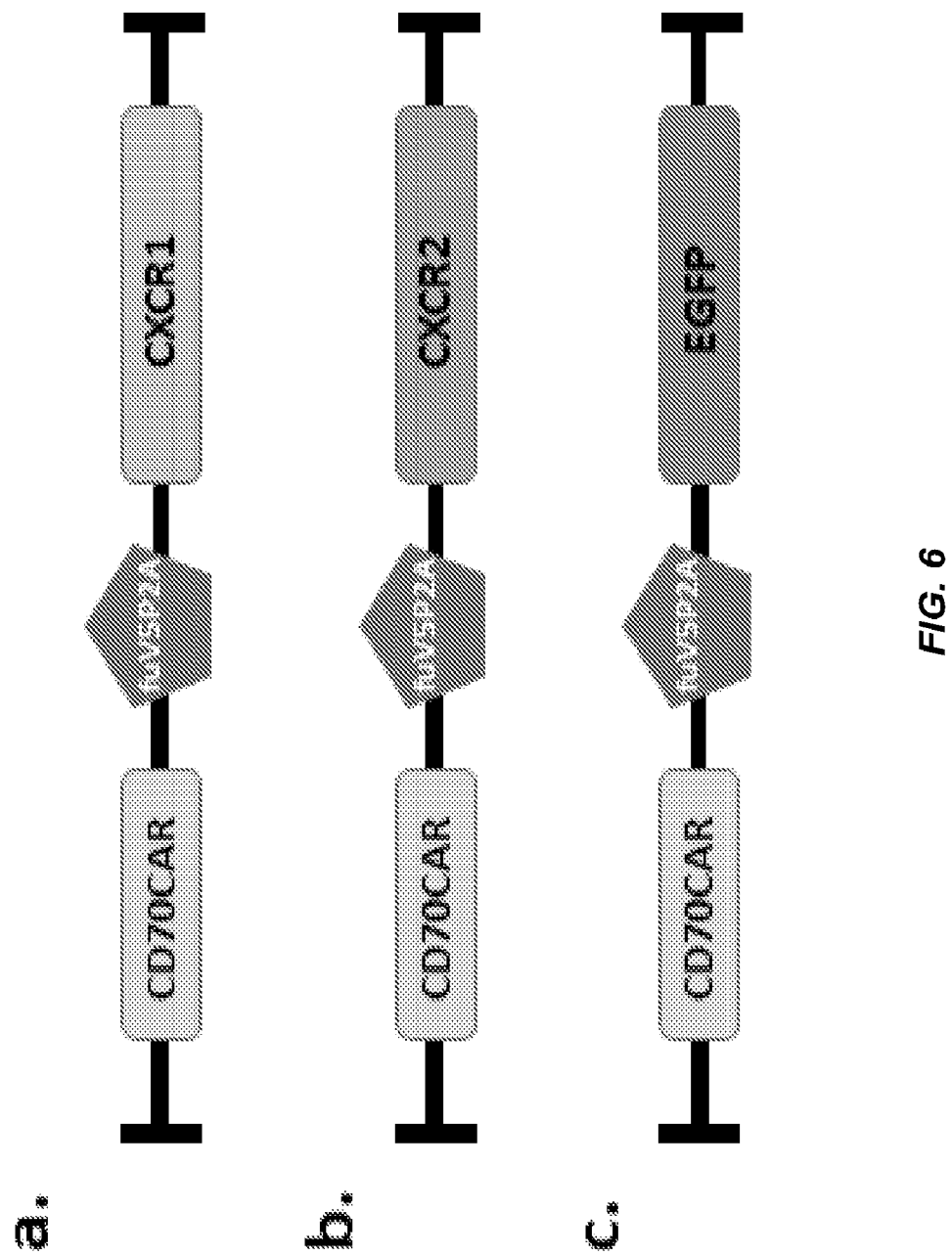
FIG. 6(A)-6(C) is a set of schematics of viral vectors showing the construction of a modified CAR according to one embodiment of the present disclosure.

In one embodiment, a recombinant protein which is a modified CAR is provided. In various aspects, the modified CAR comprises an IL-8R (or fragment thereof that retains IL-8 binding) linked to a CAR, which in turn comprises an antigen-binding domain, a transmembrane domain (optionally separated by a spacer), and a signaling domain (e.g., CD3 zeta domain). In various aspects, the CAR comprises a costimulatory signal domain (e.g., CD28 or 41BB). The CAR and the IL-8R sequences are joined by a hinge domain. FIG. 6 is a set of schematic structure of viral vectors showing the construction of a modified CAR according to one embodiment of the present disclosure. Panel (a) of FIG. 6 illustrates a recombinant protein CD70CAR-fuV5P2A-CXCR1 (SEQ ID NO: 1), which comprises a CD70 CAR fused to an IL-8 receptor CXCR1 via a hinge domain fuV5P2A (SEQ ID NO: 7). Panel (b) of FIG. 6 illustrates a recombinant protein CD70CAR-fuV5P2A-CXCR2 (SEQ ID NO: 2), comprising a CD70 CAR fused to an IL-8 receptor CXCR2 via a hinge domain fuV5P2A. Panel (c) of FIG. 6 illustrates a recombinant protein CD70CAR-fuV5P2A-EGFP (SEQ ID NO: 3), comprising a CD70 CAR fused to an enhanced green fluorescent protein (EGFP) via a hinge domain fuV5P2A. In the fusion proteins shown in FIG. 6, CD70 CAR comprises an extracellular part of CD27 as an antigen-binding region, an intracellular part of 41BB, and CD3 zeta as signaling domains. The intermediate fragment fuV5P2A comprises a furin cleavage site followed by a V5 peptide tag that is introduced upstream of P2A peptide to yield optimal gene expression.[45] IL-8 receptors (CXCR1 or CXCR2) or EGFP is added downstream of CD70 CAR. EGFP is added to the same location that CXCR1 or CXCR2 is added as a non-modified control.

The nucleic acid sequence encoding a recombinant protein comprising an interleukin 8 (IL-8) receptor attached to a chimeric antigen receptor (CAR) via a hinge domain, wherein the CAR comprises an antigen binding domain, a transmembrane domain, and a CD3 zeta signaling domain, optionally comprises any one or more of the nucleic acid sequences set forth herein, or a nucleic acid sequence comprising at least 80% identity (e.g., at least 85% identity or at least 90% identity or at least 95% identity or 100% identity) to one or more of the sequences set forth herein. In various aspects, the nucleic acid sequence comprises at least 90% identity (e.g., at least 95% or 100% identity) to one or more of the sequences set forth herein. As used herein, "at least 90% identity" and similar terms encompass any integer from, e.g., 90% to 100%, such as 90%, 91%, 92%, 93%, 94%, 95%, 96%, 97%, 98% or 99% and the like.

For simplicity, FIG. 6 illustrates CXCR1- or CXCR2-modified CD70 CAR. In alternative embodiments, a recombinant protein may comprise other CAR fused with CXCR1 or CXCR2 via a hinge domain such as (but not limited to) fuV5P2A. The other CAR may be CD19 CAR, or a CAR against an antigen expressed by a breast cancer cell, a prostate cancer cell, a lung cancer cell, a colorectal cancer cell, a melanoma cancer cell, etc.[42]

The disclosure further provides a nucleic acid encoding an IL-8 receptor-modified CAR. In one embodiment, provided is a nucleic acid comprising a nucleic acid sequence encoding a recombinant protein comprising an IL-8 receptor (CXCR1 or CXCR2) and a CAR. The IL-8 receptor and the CAR are linked via a hinge domain. The CAR comprises an antigen binding region or domain, a transmembrane domain, and a signaling domain, such as a CD3 zeta signaling domain. In one embodiment, the antigen binding region is an extracellular part of CD27. In one embodiment, the transmembrane domain is an intracellular part of 41BB. In one embodiment, the hinge domain is fuV5P2A (SEQ ID NO: 7), which comprises a furin cleavage site followed by a V5 peptide tag. It is introduced to the upstream of P2A peptide to yield optimal gene expression.[45] In one embodiment, the IL-8 receptor is CXCR1 or CXCR2. In one embodiment, a nucleic acid encoding a recombinant protein CD70CAR-fuV5P2A-CXCR1 (SEQ ID NO: 1) is provided. In another alternative embodiment, a nucleic acid encoding the recombinant protein CD70CAR-fuV5P2A-CXCR2 (SEQ ID NO: 2) is provided. In another alternative embodiment, a nucleic acid encoding recombinant proteinCD70CAR-fuV5P2A-EGFP (SEQ ID NO: 3) is provided.

The disclosure further provides vectors that comprise expression cassettes to express the IL-8 receptor modified CAR, as well as vectors that comprise expression cassettes encoding EGFP modified CAR, that may be used as a control. In one embodiment, the vector comprises an expression cassette for expressing CXCR1 modified CD70 CAR. In one embodiment, the expression cassette comprises a nucleic acid sequence encoding the recombinant protein CD70CAR-fuV5P2A-CXCR1 (SEQ ID NO: 1), wherein the nucleic acid sequence is operably linked to a promoter for expression. In an alternative embodiment, the vector comprises an expression cassette for expressing CXCR2 modified CD70 CAR. The expression cassette comprises a nucleic acid sequence encoding the recombinant protein CD70CAR-fuV5P2A-CXCR2 (SEQ ID NO: 2), wherein the nucleic acid sequence is operably linked to a promoter for expression. In an alternative embodiment, the vector comprises an expression cassette for expressing EGFP modified CD70 CAR, such as recombinant protein CD70CAR-fuV5P2A-EGFP (SEQ ID NO: 3), wherein a nucleic acid sequence encoding CD70CAR-fuV5P2A-EGFP is operably linked to a promoter for expression. In some embodiments, the vector is a retroviral vector, although alternative expression vectors may be used in the context of the disclosure Exemplary viral vectors include, but are not limited to, retroviral vectors, including lentivirus vectors; parvoviral vectors, such as adeno-associated viral (AAV) vectors; adenoviral vectors; adenoviral adeno-associated chimeric vectors; vaccinia viral vectors; and herpesviral vectors. Any of these expression vectors can be prepared using standard recombinant DNA techniques described in, e.g., Sambrook et al., Molecular Cloning, a Laboratory Manual, 2d edition, Cold Spring Harbor Press, Cold Spring Harbor, N.Y. (1989), and Ausubel et al., Current Protocols in Molecular Biology, Greene Publishing Associates and John Wiley & Sons, New York, N.Y. (1994). The nucleic acid sequences in a vector may be codon optimized. In some embodiment, the vector is pMSGV8MCS2-CD70CAR.CXCR1, which is a retroviral vector comprising a nucleic acid sequence encoding CD70CAR-fuV5P2A-CXCR1.

The disclosure also provides a genetically engineered cell carrying a vector for expressing a recombinant protein comprising an IL-8 receptor modified CAR. In one embodiment, the recombinant protein is CD70CAR-fuV5P2A-CXCR1 (encoded by SEQ ID NO: 1) or CD70CAR-fuV5P2A-CXCR2 (encoded by SEQ ID NO: 2). In one embodiment, the genetically engineered cell is a engineered T cell comprising a nucleic acid encoding a recombinant protein. The engineered T cell produces or coexpresses the IL-8 receptor and CAR on their surface. In one embodiment, the genetically engineered cell coexpresses CXCR1 (encoded by SEQ ID NO: 4) and CD70 CAR (encoded by SEQ ID NO: 6) on the cell surface. In an alternative embodiment, the genetically engineered cell coexpresses CXCR2 (encoded by SEQ ID NO: 5) and CD70 CAR (encoded by SEQ ID NO: 6) on the cell surface. In an alternative embodiment, a genetically engineered cell produces EGFP modified CD70 CAR, e.g., recombinant protein CD70CAR-fuV5P2A-EGFP (encoded by SEQ ID NO: 3).

In various aspects, the T cells are autologous with respect to the intended recipient. In this regard, in one embodiment, the genetically engineered cell is engineered based on a T cell separated or collected from a subject or patient who is going to receive the genetically engineered cell. In an embodiment, the genetically engineered cell is engineered based on a T cell separated or collected from a subject or patient who is a donor and will not receive the genetically engineered cell. Alternatively, the genetically engineered cell is engineered based on a stem cell. As used herein, "genetically engineered cell" or "modified T cell" is not limited to cells which have been directly modified; the term also encompasses progeny of cells that were modified to comprise the disclosed nucleic acid, which progeny express the IL-8R-modified CAR.

Also provided is a pharmaceutical composition comprising a genetically engineered T cell as described herein. The pharmaceutical composition further may comprise an adjuvant and/or a pharmaceutically acceptable diluent or excipient. In one embodiment, the pharmaceutical composition is formulated in liquid for injection or infusion. In one embodiment, the pharmaceutical composition comprises a genetically engineered T cell expressing an IL-8 receptor (CXCR1 or CXCR2) and a CAR (e.g., CD70 CAR), wherein the genetically engineered T cell is suspended in phosphate-buffered saline (PBS). In one embodiment, the pharmaceutical composition is formulated in powder that may be prepared into liquid before use.

The disclosure further provides a method of preparing a modified T cell for immunotherapy. The method comprises genetically modifying a T cell by introducing into the cell a vector comprising an expression cassette comprising a nucleic acid encoding the IL8 receptor-modified CAR, and expanding the T cell (i.e., allowing the T cell to replicate).

Also provided is a method of treating a tumor or cancer. The method comprises administering to a subject in need thereof a modified T cell, wherein the modified T cell comprises a nucleic acid sequence encoding a recombinant protein comprising an interleukin 8 (IL-8) receptor attached to a chimeric antigen receptor (CAR) via a hinge domain. The CAR comprises an antigen binding domain, a transmembrane domain, and a CD3 zeta signaling domain. In various aspects, the CAR includes a costimulatory domain. In various aspects, the IL-8R is CXCR1 and the CAR is a CD70 CAR. Alternatively, the IL-8R is CXCR2 and the CAR is a CD70 CAR. Alternatively, the modified T cell co-expresses EGFP and a CD70 CAR, which may be used as a control.

The subject may be a live animal, such as a human. In one embodiment, the subject is a patent having a tumor. In one embodiment, the patent has glioma. A pharmaceutical composition comprising the modified T cell may be administered systemically or regionally into the subject or the patient. In one embodiment, a pharmaceutical composition comprising the modified T cell described herein is administered to a subject by injection or infusion. In one embodiment, a pharmaceutical composition comprising the modified T cell described herein is administered to the subject by intravenous (IV) injection or infusion. In one embodiment, a pharmaceutical composition comprising the modified T cell described herein is regionally injected or infused into the brain region or ventricle of the brain. Optionally, the modified T cell is administered intrathecally. In one embodiment, the IL-8 receptor modified CAR T cell is administered to a subject after the subject has received radiotherapy.

Figure 7:
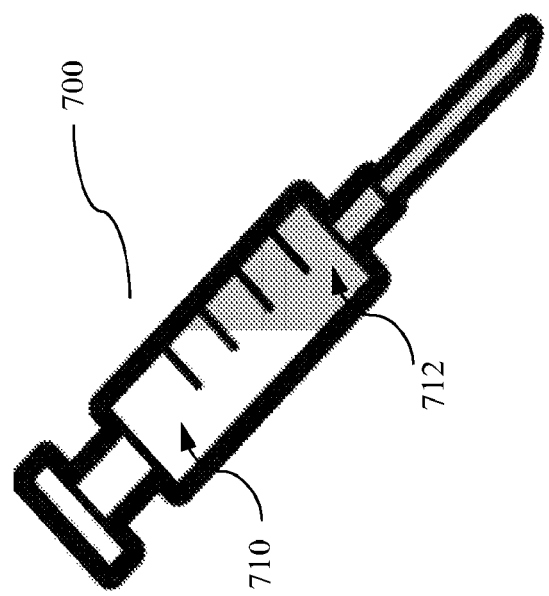
FIG. 7 illustrates a delivery apparatus for delivering a pharmaceutical composition disclosed herein according to one embodiment of the present disclosure.

A delivery apparatus for injecting or infusing a pharmaceutical composition comprising the modified T cell described herein to a subject is further provided. The delivery apparatus contains the pharmaceutical composition disclosed herein. This delivery apparatus may be an injectable drug delivery device containing an injectable liquid solution or suspension contained in the injectable drug delivery device, wherein the injectable liquid solution or suspension comprises at least one IL-8 receptor modified CAR T cell and (i) an adjuvant and/or (ii) a pharmaceutically acceptable diluent or excipient. FIG. 7 illustrates a delivery apparatus 700 for delivering a pharmaceutical composition disclosed herein. The delivery apparatus comprises an injectable drug delivery device 710 and a liquid solution or suspension 712 comprising the pharmaceutical composition disclosed herein.

Having described the many embodiments of the present disclosure in detail, it will be apparent that modifications and variations are possible without departing from the scope of the disclosure defined in the appended claims. Furthermore, it should be appreciated that all examples in the present disclosure, while illustrating many embodiments of the disclosure, are provided as non-limiting examples and are, therefore, not to be taken as limiting the various aspects so illustrated.

All documents, patents, journal articles and other materials cited in the present application are incorporated herein by reference.

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

The present disclosure is further defined in the following Examples. It should be understood that these Examples are given by way of illustration only. From the above discussion and these Examples, one skilled in the art may ascertain the essential characteristics of embodiments of the present invention. Without departing from the spirit and scope thereof, one skilled in the art may make various changes and modifications of the invention to adapt it to various usages and conditions. All publications, including patents and non-patent literature, referred to in this specification are expressly incorporated by reference herein.

EXAMPLES

Example 1

This example shows that IL-8 receptor modified CARs show antitumor response.

Materials and Methods

Cell Culture, In Vitro Irradiation and Human PBMC

The human U87 glioma cell line was purchased from ATCC (Manassas, USA), and Near-infrared protein iRFP720 was introduced to U87 to generate U87-i720 by retro-viral transduction. Cells were cultured in DMEM (Thermo Fisher Scientific, USA) supplemented with 10% fetal bovine serum (VWR, USA) and penicillin-streptomycin (Thermo Fisher Scientific, USA). Cells were irradiated using X-ray with X-RAD 320 system (Precision X-ray, USA) at the dose of 6 Gy. Healthy donors' and cancer patients' peripheral blood mononuclear cells (PBMC) samples were from Life South (Gainesville, USA). Institutional Review Board (IRB) and IACUC rules were followed.

Generation of Retro-Viral Vectors

New multiple clone site DNA fragment containing two clone sites was synthesized by IDT (Coralville, USA), abbreviated as MCS2, which consists of Ncol, PacI, BstBI, SalI enzyme sites. Two clone sites were linked by a linker, which is a fuV5P2A—an optimized 2A self-cleaving peptide. MCS2 was introduced into pMSGV8 retroviral backbone using Ncol and SalI digestion. CD70 CAR was generated as described (Wang, Q J et al, Clin Cancer Res, 2017) and cloned into the upstream site. Human CXCR1 or CXCR2 or EGFP was cloned into downstream site to generate pMSGV8MCS2-CD70CAR.CXCR1 or pMSGV8MCS2-CD70CAR.CXCR2 or pMSGV8MCS2-CD70CAR.EGFP. Click Beetle Red luciferase (CBRLuc) gene was cloned into pMSGV8 to generate pMSGV8-CBRluc. All gene fragments were codon optimized and synthesized by IDT (Coralville, USA).

CAR-T Transduction

Retroviral particles were generated by transiently transfecting GP2-293T cells (Takara Bio, USA) with transfer plasmid or vector control plasmid along with pMD2.G plasmid expressing appropriate envelopes. Lipofectemine 2000 (Thermo Fisher Scientific, USA) was used as transfection agent. The viral supernatants were collected 48 hours post transfection. PBMCs from healthy donors ($1 \times 10^6$ cells/ml) were stimulated with Dynabeads® Human T-Activator CD3/CD28 (Thermo Fisher Scientific, USA) (cells to beads ratio 1:3) for 3 days. On day 3, T cells ($5 \times 10^5$ cells/well) were transduced 2 ml of the viral sup containing half CAR and half CBRluc on RetroNectin (Clontech Laboratories, USA) coated plate in the presence of 100 IU/ml rhIL-2 (R&D Systems, USA). Transduction efficiency was determined via analysis of CXCR1 or CXCR2 or EGFP by FACS.

FACS Analysis

Anti-human CD3, CXCR1, CXCR2 (BD Biosciences, San Jose, Calif.) were used to define the transduction efficiency of IL8R modified CD70 CAR-T.

Transwell Migration Assay

Transwell inserts (Pore size 5.0 um, Corning, USA) were placed onto the 24 well-plate. 500 ul of recombinant human IL-8 (Sigma-Aldrich, USA) or conditioned media from radiated U87 cell culture was applied into the bottom of the well as attractant for T cells. $2 \times 10^5$ T cells in 200 ul media was added to the upper chamber. In some experiments, anti-IL8 blocking antibody (BD Biosciences, San Jose, Calif.) was added to the bottom media as a control. After 1 hour incubation, cells in the bottom well were collected and counted by CountBright™ Absolute Counting Beads (Thermo Fisher Scientific, USA) with flow cytometer. Chemotaxis index (CI) indicates the ratio of cells migrated to the chemokine or conditioned media versus medium only. Absolute number of migrated cells were also used to evaluate chemotaxis.

Orthotopic Glioblastoma Mouse Model and In Vivo Imaging

All animal experiments followed a protocol approved by University of Florida Institutional Animal Care and Use Committee. U87-i720 was harvested and cell pellets were resuspended in PBS at the appropriate concentration of viable cells as determined by trypan blue dye exclusion, mixed with equal volume of 10% methylcellulose in Zinc Option Modified Eagle's medium(MEM) and loaded into a 250 μl syringe (Hamilton, Reno, Nev.) with an attached 25-gauge needle. In NRG mice, the tip of the needle was positioned at bregma and 2 mm to the right of the cranial midline suture and 4 mm below the surface of cranium using stereotactic frame. All mice received $5 \times 10^4$ tumor cells in a volume of 2.5 μl. Local radiation and CAR-T treatment were performed as time line show. CAR-T or vector control T cells were delivered by i.v. injection with $2 \times 10^6$ in 100 μl PBS. They were regularly examined for any neurologic deficits, weight loss, or signs of stress and euthanized according to preset criteria in accordance with the University of Florida for Comparative Medicine guidelines.

Tumor growth and T cell trafficking were monitored using the IVIS system (IVIS, Xenogen, Alameda, Calif.). Mice were anesthetized with isofluorane and fluorescent signal of tumor was imaged first. Then mice were received 150 mg/kg D-luciferin (PerkinElmer) intraperitoneally for T cell bioluminescence imaging. The image was analyzed using Living Image software (Caliper Life Sciences, Hopkinton, Mass.).

Local Radiation In Vivo

Animals were anesthetized with a dose of ketamine at 100 mg/kg and 10 mg/kg xylazine. Then 4 animals were placed at 100 cm from the radiation source on the standard treatment with the radiation beam being sharply collimated to only expose the skulls to the radiation beam, and only right side of head was radiated, where tumors were inoculated. A bolus (blanket of 1 cm thickness tissue equivalent material) was placed over the mice so that it is in contact with the head. The bolus is needed to allow the radiation to build to the proper dose below the surface of the skull, i.e., within the intracranial tumor. With the bolus, the radiation dose will be uniform to within 5% of the mean head dose. A dose of 4.5 Gy to head was delivered, which takes 2-3 minutes. After radiation, mice were placed on warm heating pad to recover sufficient consciousness. Two fractionated radiations were performed as timeline show.

Statistical Analysis

Unpaired t test were used to compare the difference between each treatment groups, and log-rank test was used to analyze survival. * $p<0.05$,  $p<0.01$, * $p<0.001$.

Results

Figure 24:
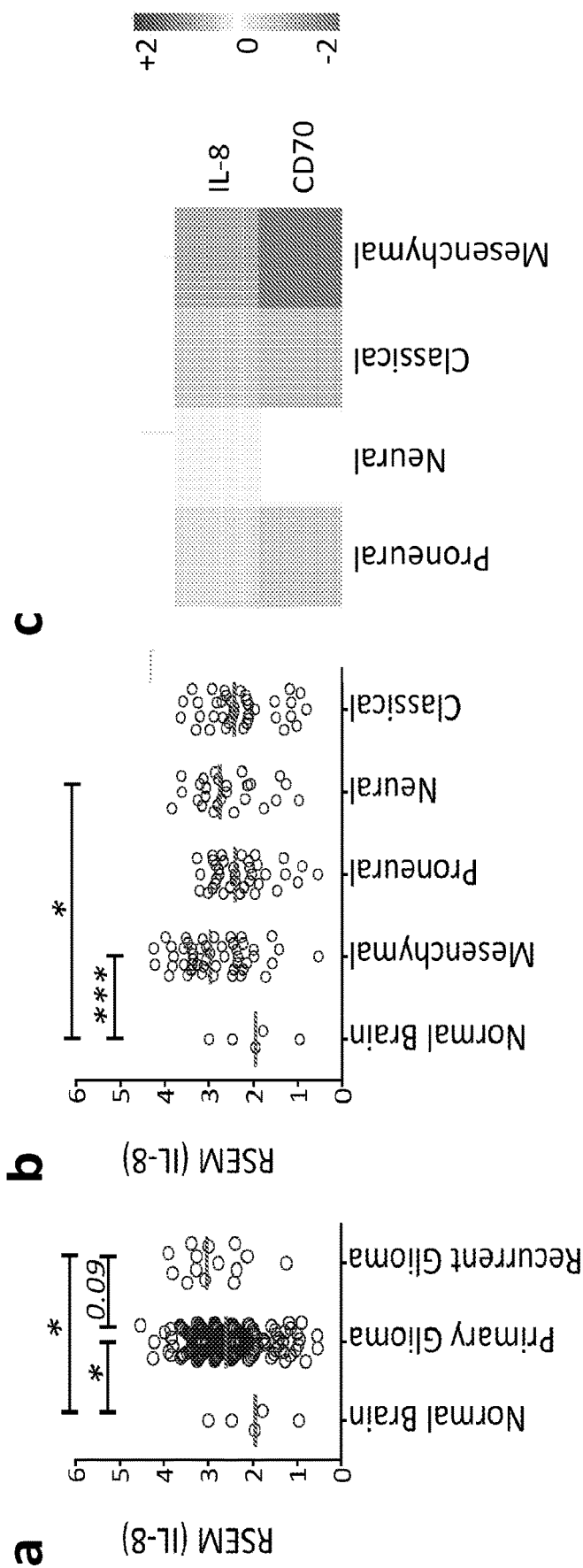
FIGS. 24(A)-24(C) illustrate IL-8 expression in human GBM subgroups. (A) IL-8 gene expression in a normal brain (n=5), primary GBM (n=153), and recurrent GBM (n=14) was analyzed using RNA-seq data from TCGA. (B) IL-8 gene expression across molecular subtypes of GBM (Mesenchymal, n=49; Proneural, n=38; Neural, n=26; Classical, n=38). (C) Heatmap of IL-8 and CD70 gene expressions in GBM subtypes. All gene-level analyses were performed using RNA-seq datasets culled from TCGA. The Mann-Whitney U test was used for the difference between 2 groups.
Figure 25:
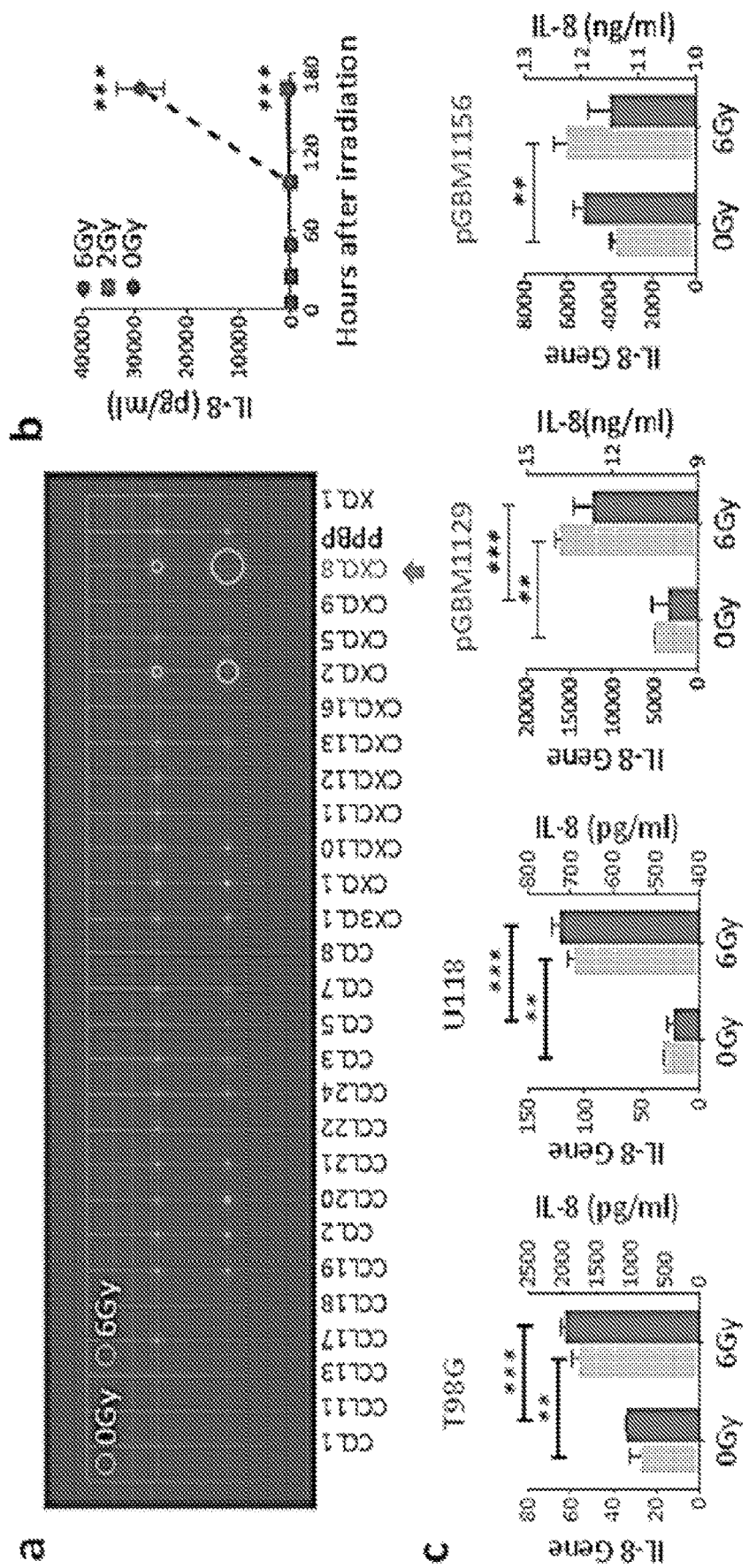
FIGS. 25(A)-25(G) demonstrate that IL-8 secretion by human gliomas is enhanced by ionizing radiation. (A) Tumor chemokine expression changes after radiation. U87 cells were radiated at 0 Gy or 6 Gy and then seeded in a 6-well plate at $1 \times 10^6$/well. Cells were harvested for RNA extraction 24 hours later, followed by cDNA synthesis and qPCR for the human chemokine profile. The circle size corresponds to the relative gene expression level. (B) Kinetics of IL-8 secretion by tumor cells. U87 cells were treated with different doses of radiation and seeded at $1 \times 10^4$/ml. Supernatants were harvested at 4, 24, 48, 96, and 168 hours, respectively, from the cell culture, and the IL-8 secretion was measured by ELISA (The data represent mean±SD; n=3; and the significance was determined by two-way ANOVA). (C) IL-8 productions from multiple GBM lines. IL-8 gene and protein expression/secretion were quantified by qPCR and ELISA, respectively, using 2 established glioma cell lines (T98G and U118) and 2 primary glioma cell lines (pGBM-1129 and pGBM-1156) 7 days after irradiation. Tumor cells were radiated at 0 Gy or 6 Gy and placed at $1 \times 10^4$/ml in a flask, and cells and cell supernatants were harvested 7 days later for IL-8 gene and protein quantitation by qPCR and ELISA. The data represent means±SEM; n=3; the statistical significance was determined using the Mann-Whitney U test. (D) Normal human astrocytes (NHAs) did not secrete IL-8 after irradiation. NHA and U87 cells were irradiated at the indicated dose, and ELISA was carried out for IL-8 production 7 days after irradiation. The data represent means±SEM; n=3; and the Mann-Whitney U test was performed. (E) A dose-dependent enhancement of IL-8 expression at the gene level. Experimental design of the xenograft mouse model with local radiation (left). Mice were injected intracranially with $5 \times 10^4$/mice of U87 cells. Eight days later, mice were locally irradiated with 0~3 fractionated doses daily at 3 Gy/day. Tumor samples were collected when mice were reaching the endpoint. IL-8 gene expression (means±SEM; n=5; by the Mann-Whitney U test) was measured by qPCR from excised tumors (right). (F) Radiation elevates IL-8 expression at the protein level. The mice were implanted intracranially with $5 \times 10^4$/mouse of U87 cells, and 7 days later, fractionated local radiation (4.5 Gy per dose) was carried out. Ten days after the radiation, the tumor was resected from the animals and tested for IL-8 tumor expression using IHC, representative images are shown. All the experiments were repeated at least 3 times. (G) Graphical summary: Ionizing radiation enhances expression of IL-8 by glioma that can be co-opted by IL-8 receptor-expressing CAR T (CD70 CAR in this study) cells to increase trafficking of adoptively transferred CAR T cells to irradiated tumors (GBM in this study).
Figure 25:
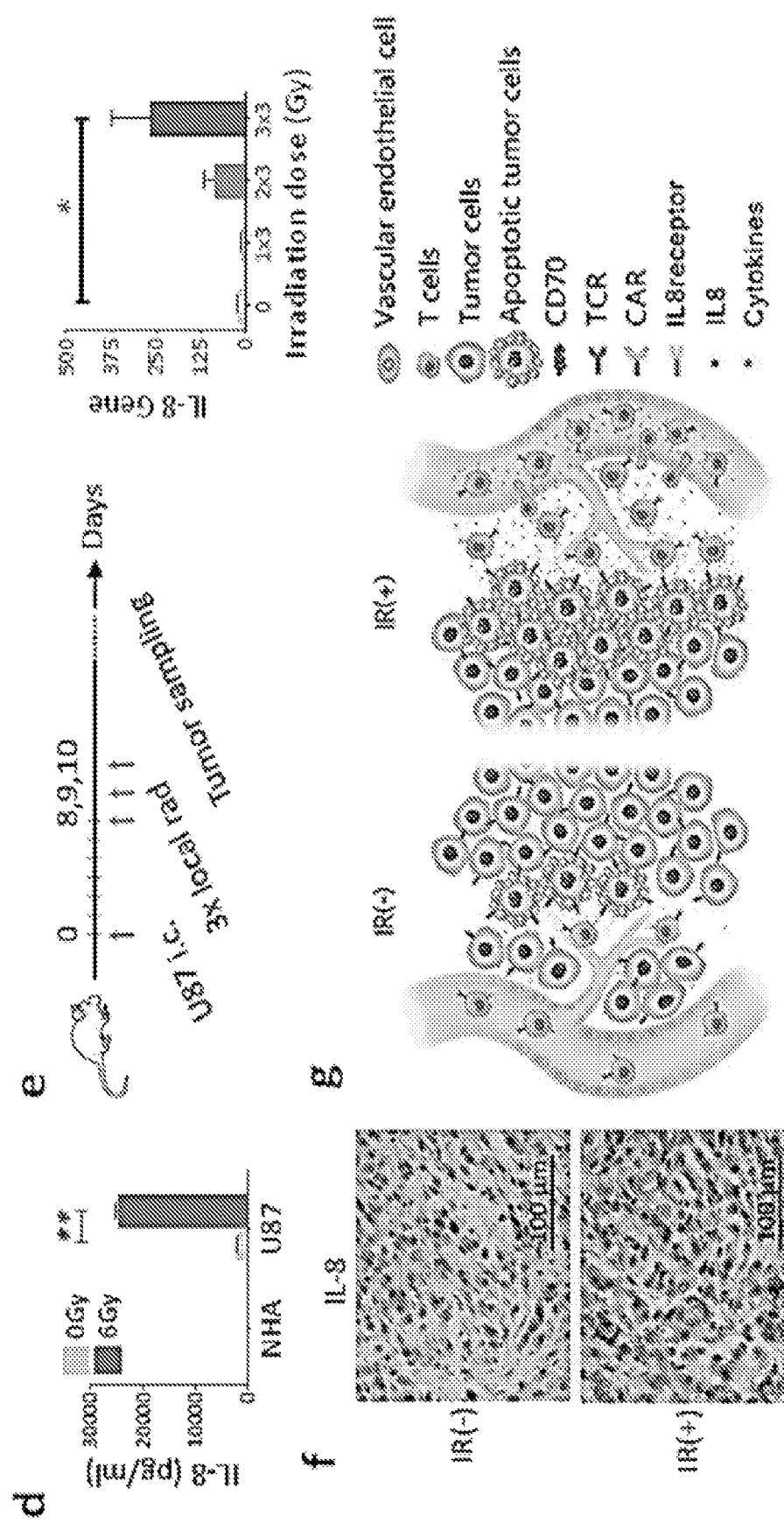
Figure 26:
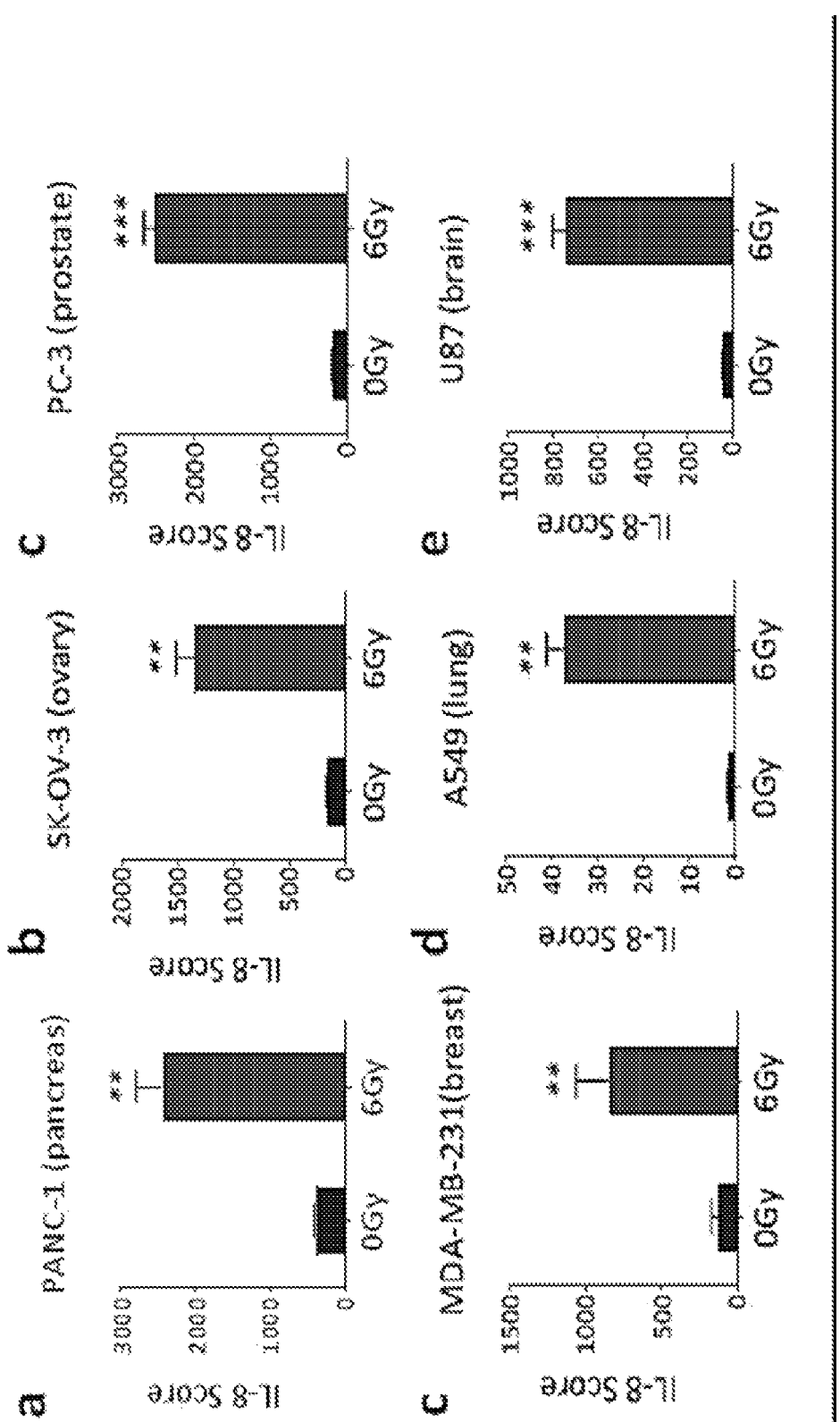
FIGS. 26(A)-26(E) demonstrate enhanced expression of IL-8 after exposure to ionizing radiation across multiple human cancer types. Tumor cells were radiated with 6 Gy irradiation and seeded at $1 \times 10^4$/ml. The supernatant was harvested 7 days after radiation, and the IL-8 secretions (means+SD; n=3) were measured by ELISA. The number of cells was determined using counting beads, and propidium iodide was used to gate viable cells. The IL-8 score represents a normalization of concentration to viable cells. The Mann-Whitney U test was used for the difference between two groups.

FIG. 25(A)-25(G) illustrate the increase in IL-8 secretion of cancer cells in response to ionizing radiation. To determine the effect of ionizing radiation on a glioma chemokine expression profile, U87 glioma cells were treated with 6 Gy radiation, followed by gene expression detection by a qPCR chemokine array (24 hours later). U87 glioma cells express several chemokines (CCL2, CCL20, CXCL1, CXCL2, CXCL8, etc.), among which IL-8 is the most abundant after radiation (FIG. 25A). To further identify the pattern of IL-8 expression by radiated gliomas, U87 cells were radiated at different doses of 0 Gy, 2 G, and 6 Gy before IL-8 enzyme-linked immunosorbent assay (ELISA) was performed at different times after radiation. Compared with lower Gy doses, the highest dose, 6 Gy, induced the most IL-8 secretion (FIG. 25B). These results were also reproduced in other glioma cell lines, including primary GBM lines (FIG. 25C), except pGBM 1156, the lower production of IL-8 protein was due to the cell death after radiation (data not shown). Normal human astrocyte (NHA) did not elicit similar increases in IL-8 production after radiation (FIG. 25D). To determine the impact of radiation on IL-8 gene expression in tumor cells in vivo, an orthotopic murine xenograft model was established by implanting U87 cells into NSG-B2m mice, followed by fractionated local radiation. Enhancement of IL-8 gene expression was observed with increasing doses of radiation (FIG. 25E). Since NRG mice are more tolerant to radiation than NSG-B2m mice, NRG mice were used for subsequent animal studies; thus, the radiation dose was changed to 2×4.5 Gy. Immunohistochemistry (IHC) staining was used to confirm the enhancement of IL-8 protein expression in the tumor samples of irradiated mice (FIG. 25F). The IL-8 gene expression profile using large cohorts of primary and recurrent glioma datasets culled from The Cancer Genome Atlas (TCGA) was examined. The primary gliomas expressed elevated levels of IL-8 and sustained their expression in the recurrent tumors (FIG. 24A). Among the four molecular subtypes of GBM, the mesenchymal subset was mostly enriched for IL-8 expression (FIG. 24B). CD70, a previously identified glioma CAR T target, was also enriched in this subset (FIG. 24C). This radiation-induced IL-8 secretion is not a unique characteristic for gliomas. Multiple tumor types exhibit a similar trend (FIG. 26A-E). Therefore, IL-8 production/secretion induced by radiation can be used as a "CAR T-cell attractor," guiding any IL-8R-modified CAR T cells to enhance T-cell tumor migration. In this study, CD70 CAR was used to test the improvement of the antitumor efficacy of the IL-8R-modified CAR T cells; it is expected that similar effects would be observed for other CAR (i.e., CAR T cells targeted to other cancer antigens).

Figure 8:
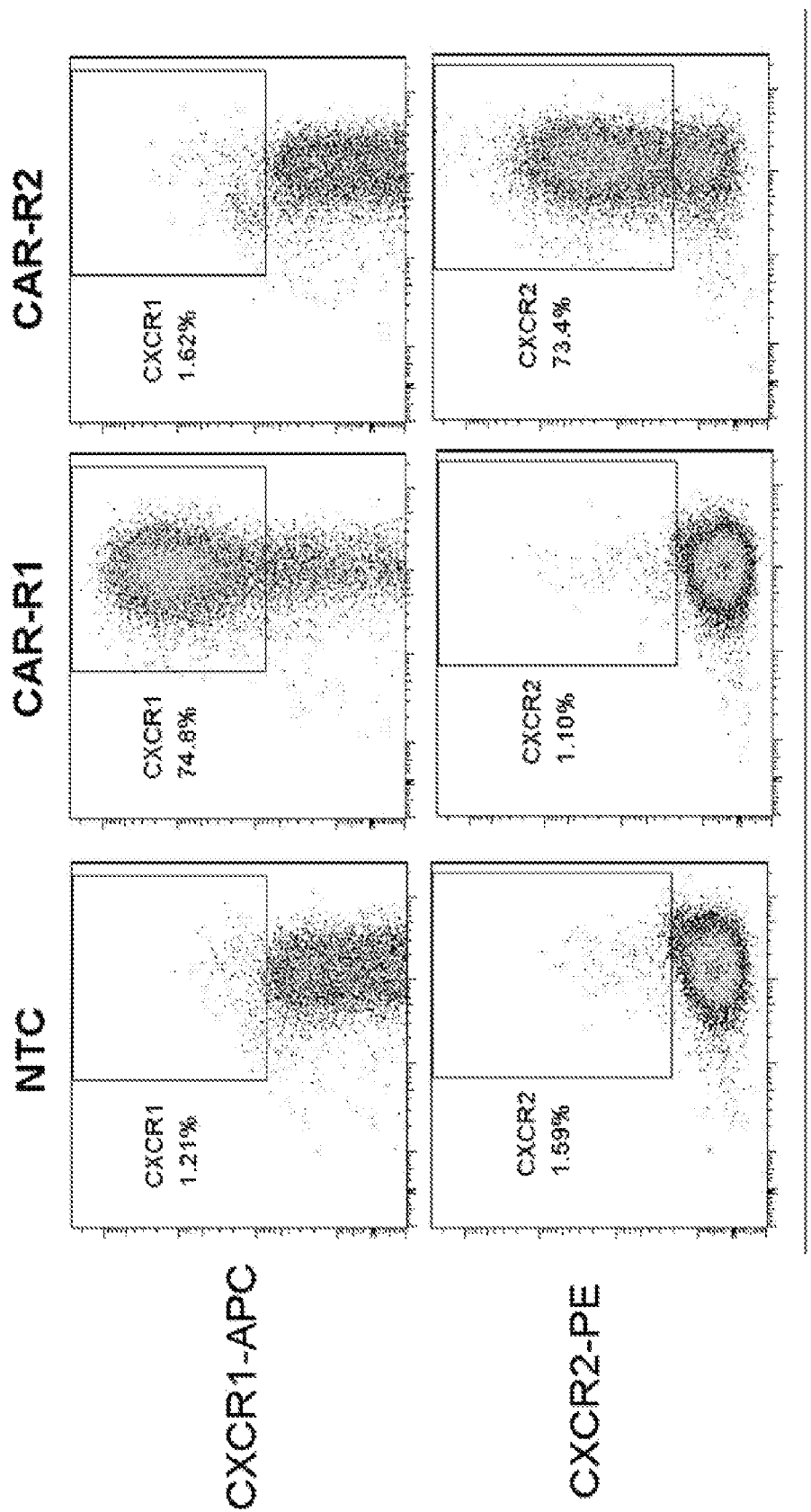
FIG. 8 illustrates identification of CXCR1 and CXCR2 after viral transduction of T cells according to one embodiment of the present disclosure.
Figure 9:
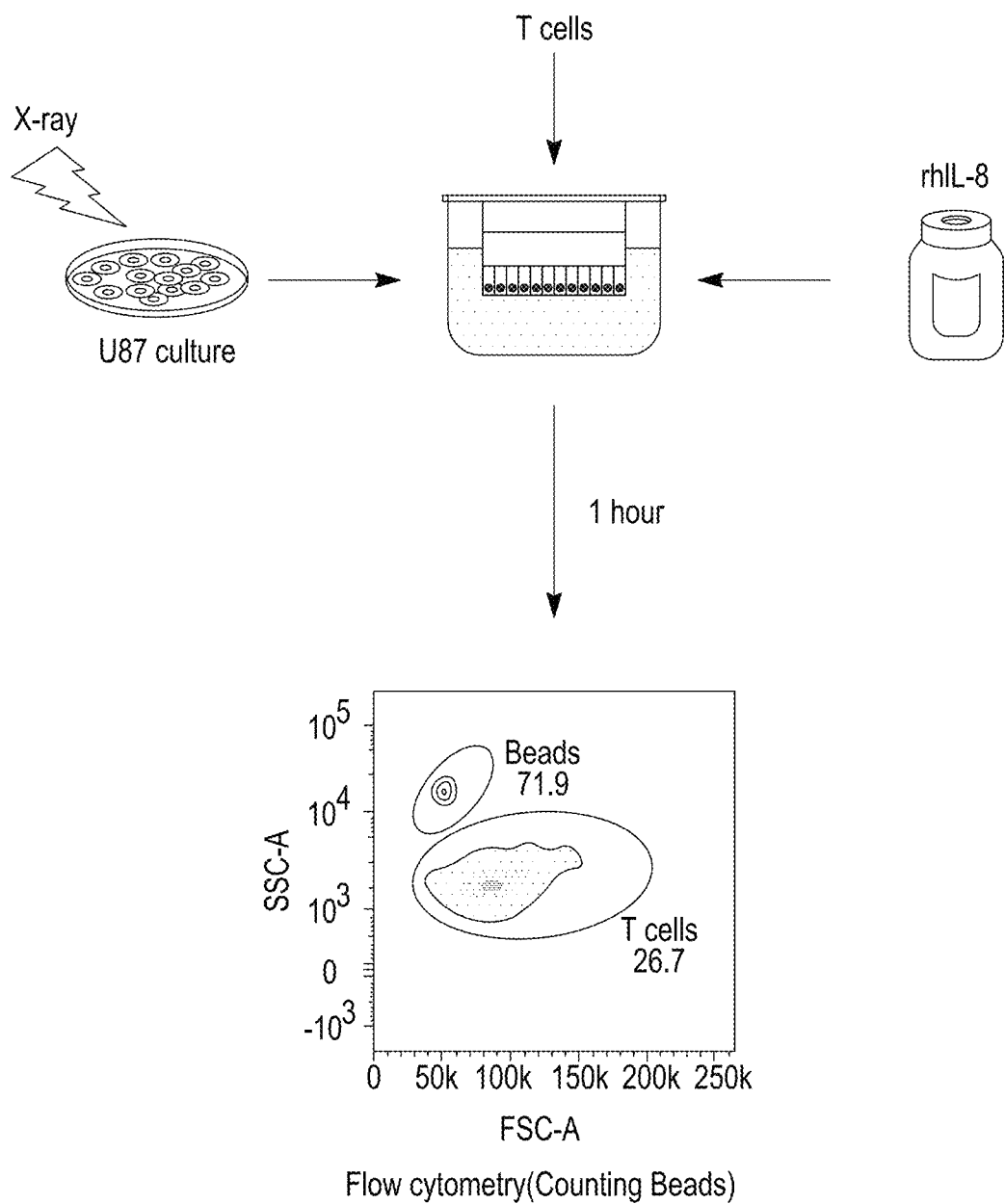
FIGS. 9-11 illustrate enhanced trafficking of IL-8 receptor expressing CD70 CART in vitro according to one embodiment of the present disclosure.
Figure 10:
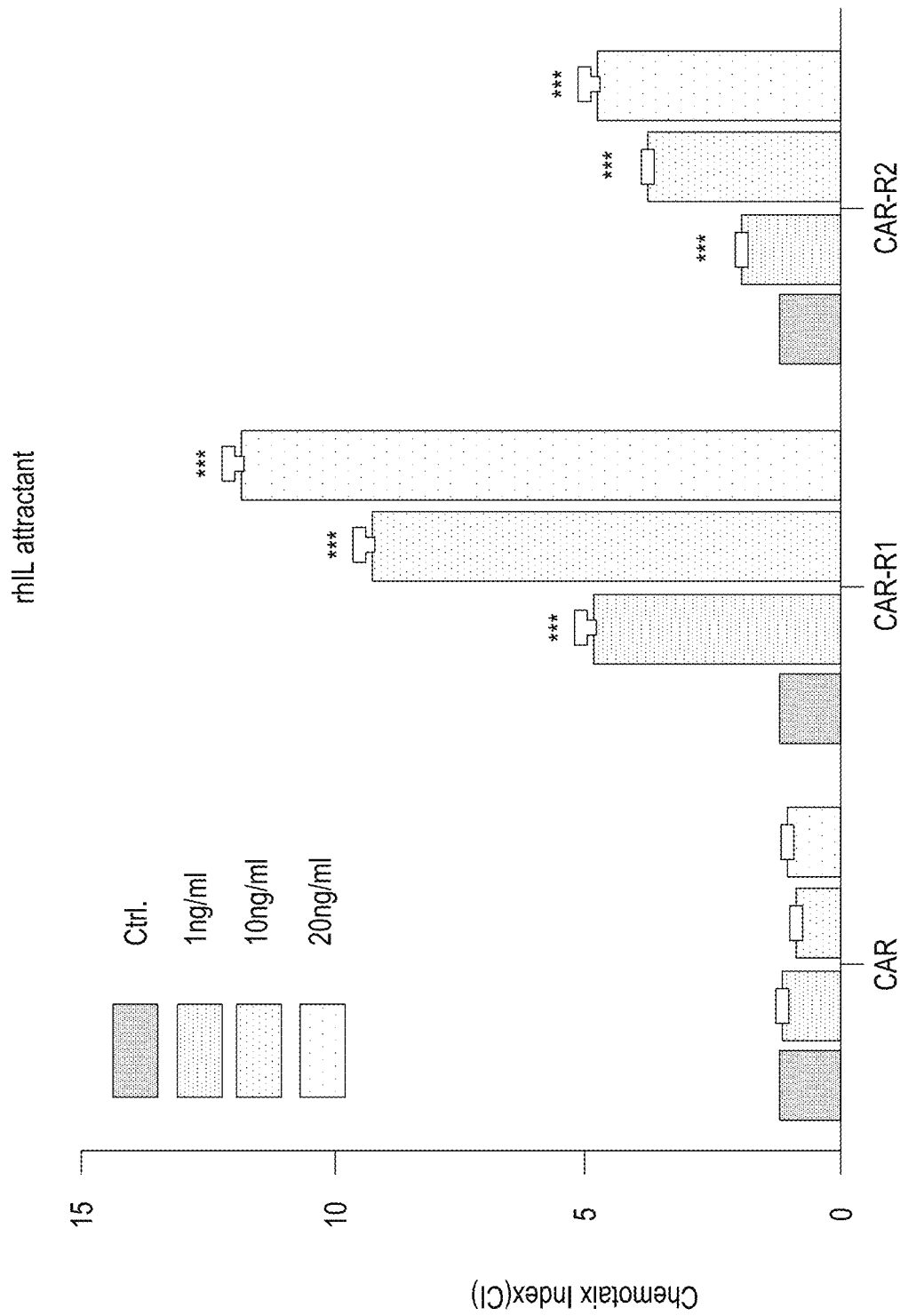
Figure 11:
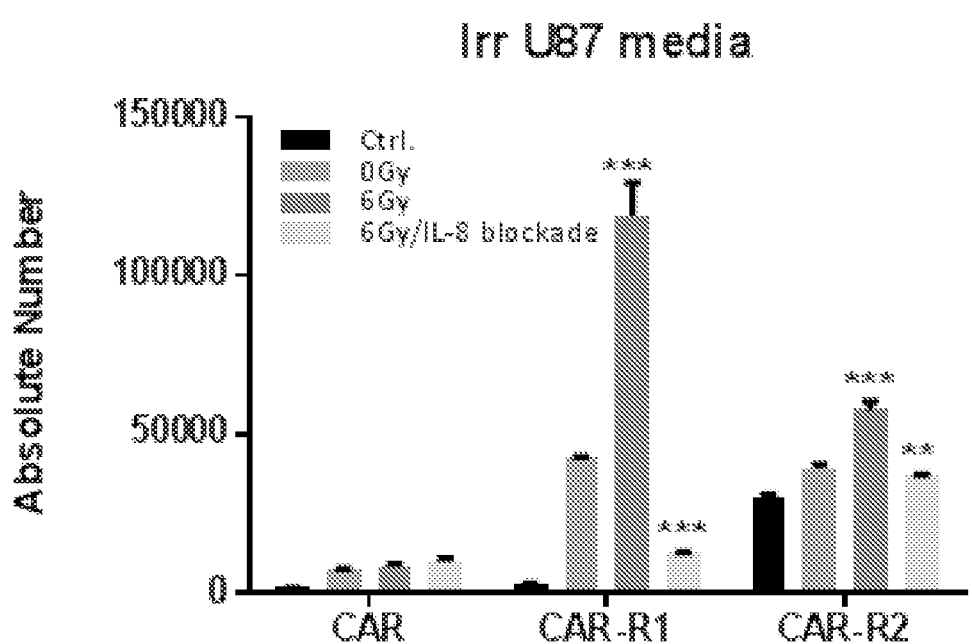

FIGS. 8-11 illustrate generation of IL-8 receptor expressing CD70 CAR-T cells and a migration assay according to one embodiment of the present disclosure. FIG. 8 illustrates identification of CXCR1 and CXCR2 after viral transduction of T cells. FIGS. 9-11 illustrate enhanced trafficking of IL-8 receptor-expressing CD70 CAR-T in vitro. Recombinant human IL-8 gradients or conditioned media from radiated glioma culture were used as attractant for CXCR1 or CXCR2 modified CD70 CAR-T. Chemotaxis index (CI) indicates the ratio of cells migrated to the chemokine or conditioned media versus medium only. Absolute number of migrated cells were also used to evaluate chemotaxis.

We also evaluated the IL-8 gene expression profile using large cohorts of primary and recurrent glioma datasets culled from The Cancer Genome Atlas (TCGA). We found that the primary gliomas expressed elevated levels of IL-8 and sustained their expression in the recurrent tumors (FIG. 24A). Among the 4 molecular subtypes of GBM, the mesenchymal subset was mostly enriched for IL-8 expression (FIG. 24B). CD70, a previously identified glioma CAR T target, was also enriched in this subset (FIG. 24C). This radiation-induced IL-8 secretion is not a unique characteristic for gliomas. Multiple tumor types exhibit a similar trend. Therefore, IL-8 production/secretion induced by radiation can be used as a "CAR T-cell attractor," guiding any IL-8R-modified CAR T cells to enhance T-cell tumor migration.

Figure 12:
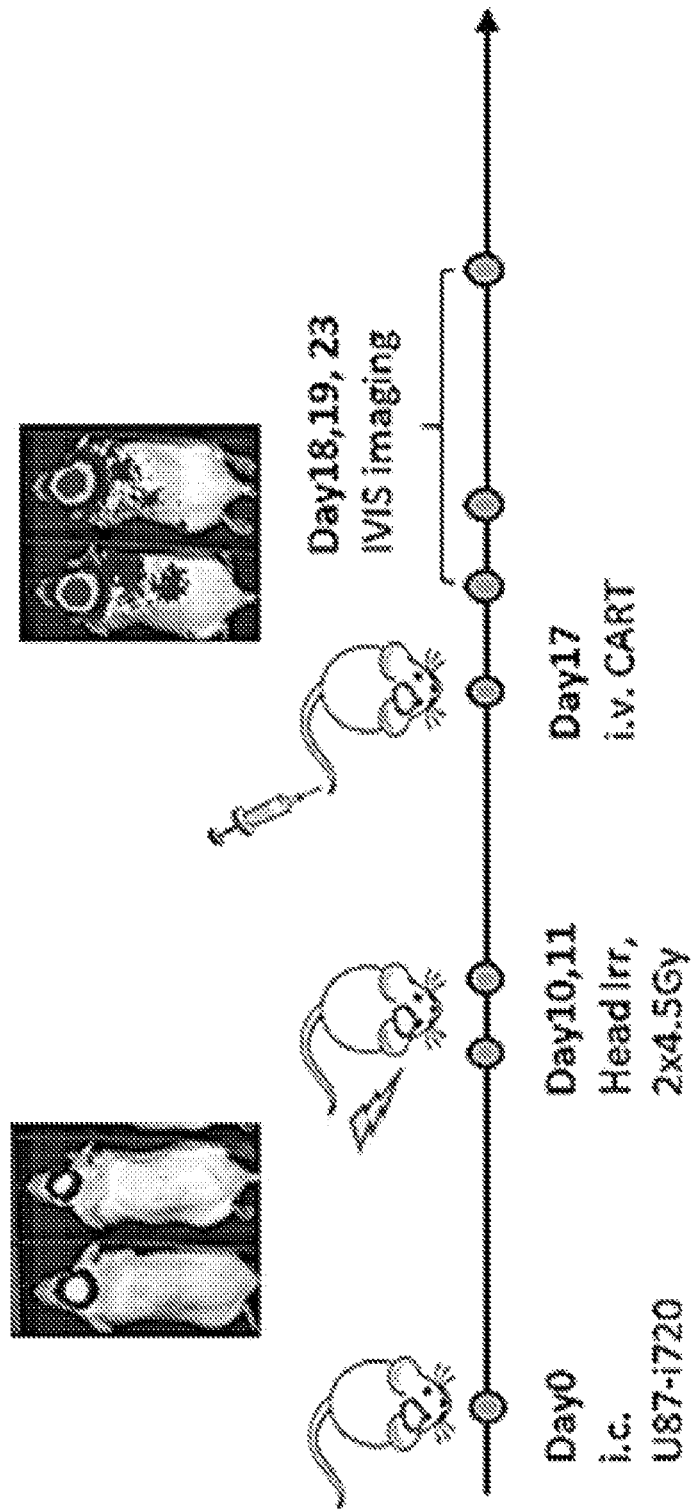
FIG. 12 illustrates a timeline of treatment of tumor-bearing mice with IL-8R modified CD70 CAR-T according to one embodiment of the present disclosure.

FIG. 12 illustrates a timeline of treatment of tumor-bearing mice with IL-8R modified CD70 CAR-T according to one embodiment of the present disclosure. $5 \times 10^4$ U87-i720 were inoculated into the brain on day 0, and the tumor establishment was identified on day 7 by iRFP-720 signals. Local radiation was delivered in two fractions on day 10 and day 11 for total 9 Gy. On day 17, $2 \times 10^6$ CAR-T or control-T cells were infused systemically. T cell trafficking and tumor growth were monitored using IVIS system.

FIG. 13 illustrates CXCR1- and CXCR2-modified CD70 CAR-T traffic to tumor site earlier than unmodified CD70 CART according to one embodiment of the present disclosure. (A) All T cells were co-transduced with retroviral vector of Click Beatle Luciferase gene to monitor T cell trafficking using IVIS imaging system. Imaging of day 1, 2, 6 post-infusion of T cell were shown. (B) Statistical analysis for brain luminescence of day 2 after CART transfer. The group of CXCR1 and CXCR2 modified CD70 CART shows higher signal than non-modified CART. In addition, the luminescence signal of vector-T cells dropped dramatically after T cell transfer. Unpaired t test was used.

Figure 14:
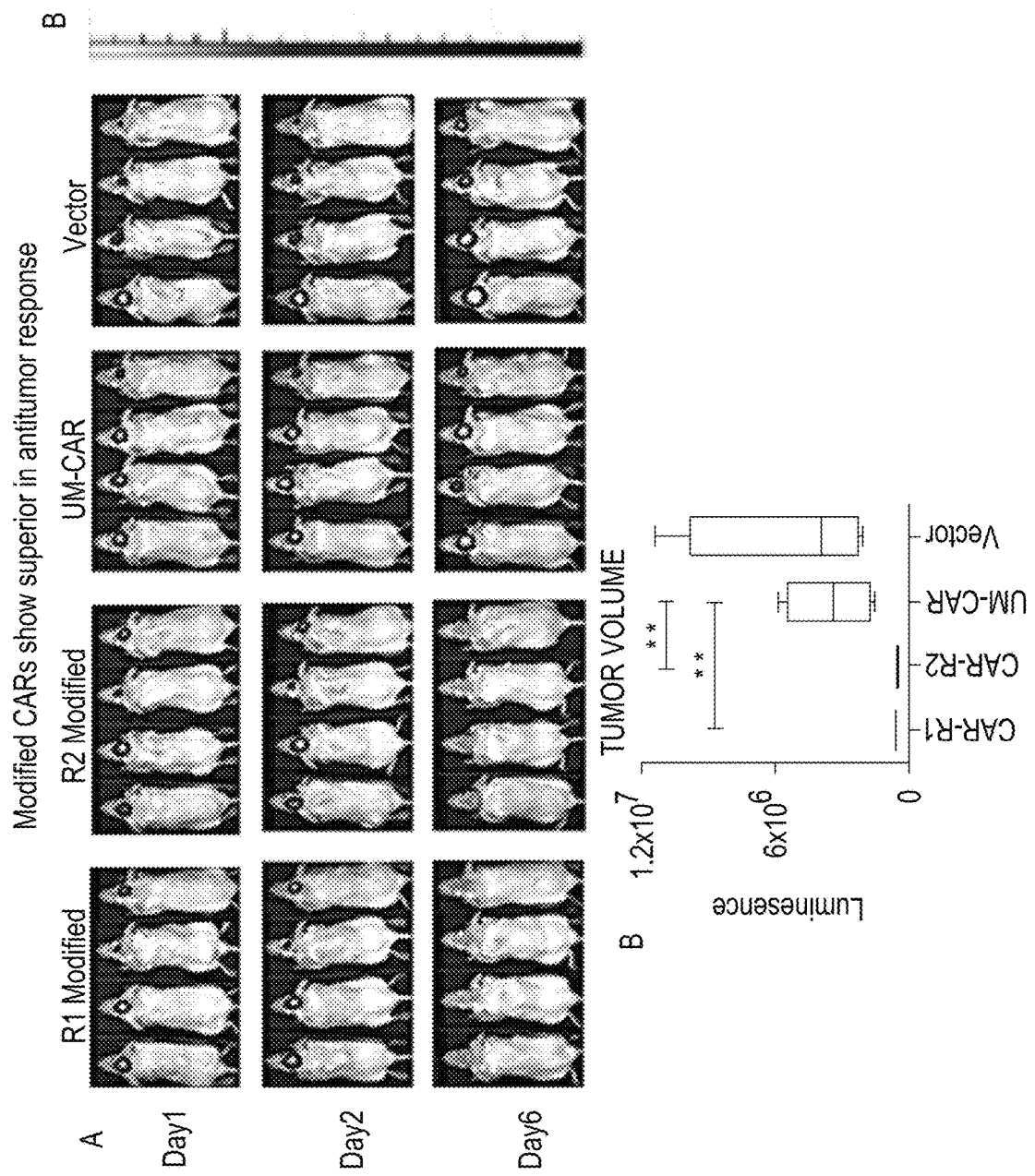
FIGS. 14(A) and 14(B) illustrate anti-tumor response of IL-8 receptor expressing CD70 CART in vivo according to one embodiment of the present disclosure.

FIG. 14 illustrates anti-tumor response of IL-8 receptor expressing CD70 CAR-T in vivo according to one embodiment of the present disclosure. (A) Near-infared protein iRFP720 was transduced to U87 cell line to track tumor growth by IVIS imaging system. (B) Statistical analysis for tumor volume of day 6 after CART transfer. CXCR1 and CXCR2 modified CD70 CART cells eradicated tumor by day 6 post-infusion of T cells, while non-modified CAR-T and Vector-T group still showed high signal of tumor. Unpaired t test was used.

Figure 15:
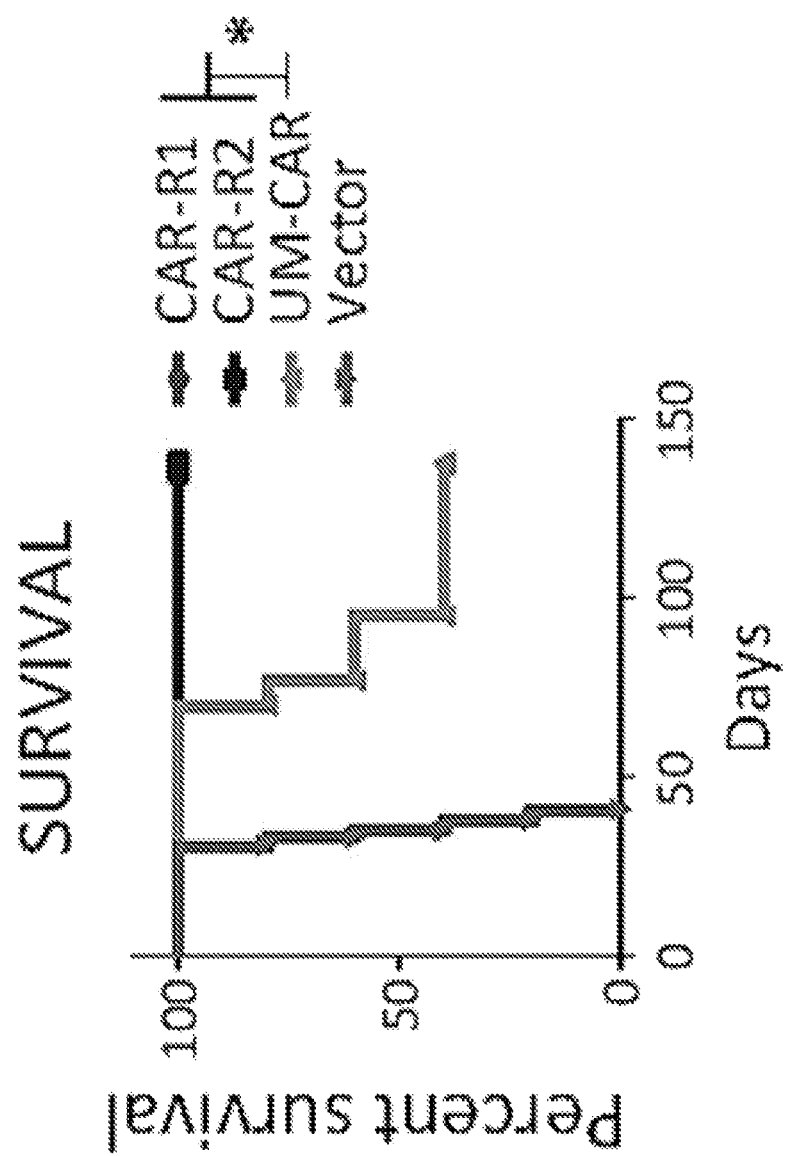
FIG. 15 illustrates that modified CARs show a long-lasting antitumor response according to one embodiment of the present disclosure. Kaplan-Meier survival curve for the U87-i720 model treated with different group of CD70 CART according to one embodiment of the present disclosure.

FIG. 15 illustrates that modified CARs show a long-lasting antitumor response according to one embodiment of the present disclosure. Kaplan-Meier survival curve for the U87-i720 model treated with different group of CD70 CART.

Figure 16:
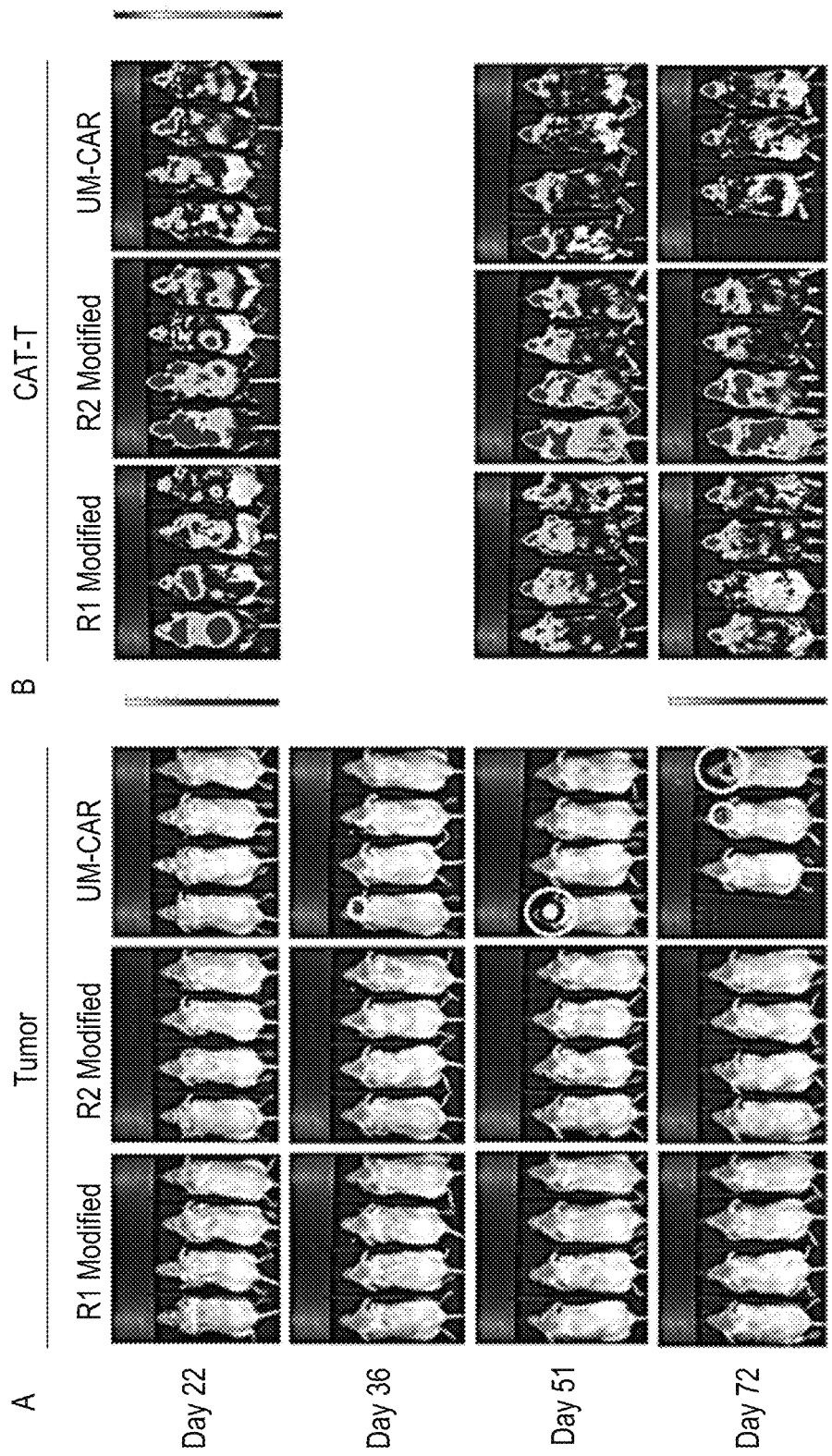
FIGS. 16(A) and 16(B) illustrate relapsed tumor in unmodified CD70 CAR T cell group according to one embodiment of the present disclosure.

FIG. 16 illustrates relapsed tumor in unmodified CD70 CAR-T group according to one embodiment of the present disclosure. Tumor signals from all CAR-T groups disappeared by day 22 post-treatment. T cells also traffic out of brain, and travel around the whole body. However, (A) tumor relapse was observed in unmodified CAR-T group from day 36, and (B) the T cells re-concentrated to the tumor site, but still could not rescue mouse from death.

FIG. 17 illustrates late stage treatment of tumor-bearing mice with IL-8R modified CD70 CAR-T according to one embodiment of the present disclosure. (A) Local radiation was delivered at a late time point of day 21, 22. CAR-T were give 29 days after tumor implantation. Dose of radiation and CAR T cell number were the same as previous treatment plan. (B) IL-8R modified CD70 CAR-T showed significantly better trafficking to tumor site then unmodified control. (C) Tumor growth regressed in the IL-8R modified CD70 CAR-T group, while unmodified control and vector control T cells could not rescue the mice. Treated groups also enjoyed enhanced survival (data not shown).

Figure 27:
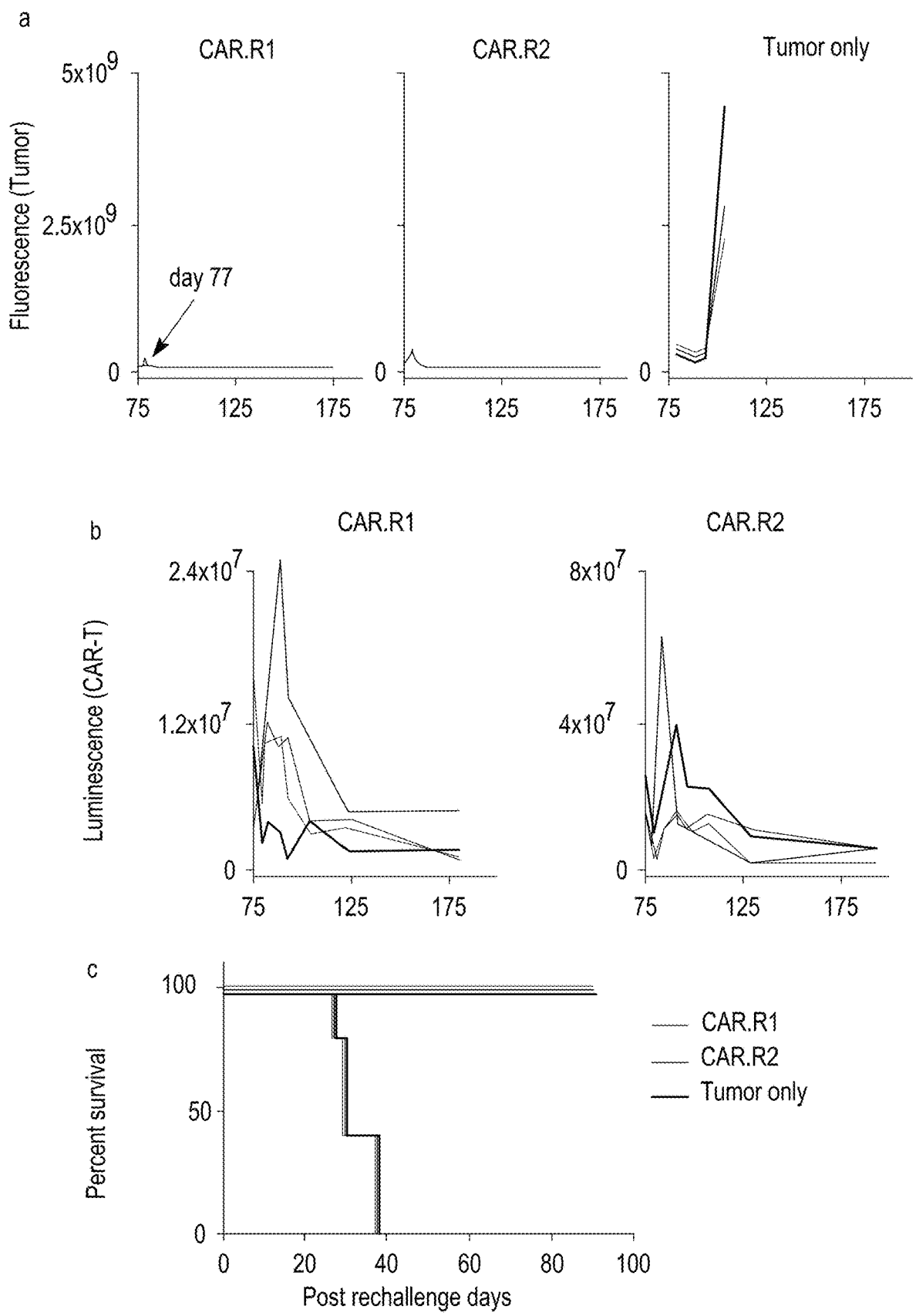
FIGS. 27(A)-27(C) demonstrate that IL-8R-modified CAR T cells cure late-stage tumors and provide long-term tumor protection. Tumor growth and CAR T-cell tumor trafficking following tumor rechallenge. (A-B) Each line represents a single mouse. (C) Kaplan-Meier survival curves of the rechallenged mice. Cured mice of the first treatment (n=4) were rechallenged with intracranial U87 tumors. The Mann-Whitney U test was used for the difference between two groups, and the long-rank test was used for the survival analysis.

To further evaluate the long-term tumor protection of IL-8R-modified CAR T cells, "cured" mice were rechallenged in the opposite hemisphere with tumor (U87.i720 on day 77 after initial implantation). While all of the control mice died from the tumor, the CXCR1 and CXCR2 CAR T cell-treated mice showed complete tumor control. (FIG. 27A) A remarkable surge of the CXCR1- and CXCR2-modified CD70 CAR-T was observed after tumor injection in rechallenged sites, which precipitated long-term survival benefits. (FIG. 27B) Treated mice survived past 100 days post-challenge, while tumor-only mice died by day 40. (FIG. 27C) Taken together, IL-8R-modified CAR design described herein equips T cells with better antitumor reactivity and immunologic memory for long-lasting tumor control.

Under these conditions, modified CAR T cells exhibit enhanced migratory and proliferative capacities leading to complete tumor regression (100% of mice were cured). Five days after tumor rechallenge, there was a surge in CAR T cells in the tumor-rejection site and long-term tumor protection was obtained. These results demonstrate the feasibility and efficacy of utilizing modified CAR T cells for homing to the tumor site.

Example 2

CD70, A Novel Target of Car T-Cell Therapy For Gliomas[37]

This example provides evidence that glioma-associated CD70 expression was not detected in normal tissues from different organs but overexpressed predominantly in subgroups of patients with gliomas (i.e., IDH wild-type LGGs and mesenchymal GBMs). The overexpressed CD70 gene was associated with poor survival in patients with LGGs (69.8 mo short, P=0.0005), IDH wild-type LGGs (13.8 mo short), and mesenchymal GBMs (5.5 mo short). It is found that CD70 is directly involved in immunosuppression by mediating production of protumor chemokines (e.g., interleukin-8, chemokine C-C ligand 2, and C-X-C motif chemokine ligand 1) and selectively inducing CD8+ T-cell death. Importantly, preclinical studies show that adoptively transferring CD70 CAR T cells induces potent antitumor response in xenograft and syngeneic models without adverse effects, suggesting that CD70 may be employed to improve outcomes in patients with refractory brain tumors. This example identifies CD70 as a novel immunosuppressive ligand and glioma target for cancer immunotherapy.

Materials and Methods

In general, normal tissues derived from 52 different organs and primary and recurrent low-grade gliomas (LGGs) and glioblastomas (GBMs) were thoroughly evaluated for CD70 gene and protein expression. The association between CD70 and patients' overall survival and its impact on T-cell death was also evaluated. Human and mouse CD70-specific chimeric antigen receptors (CARs) were tested respectively against human primary GBMs and murine glioma lines. The antitumor efficacies of these CARs were also examined in orthotopic xenograft and syngeneic models.

Patient Samples

A summary of tumor samples and clinicopathological details of the patients is shown in FIG. 28. Healthy donors' and cancer patients' peripheral blood mononuclear cell (PBMC) samples were from HMU or LifeSouth. Institutional review board and Institutional Animal Care and Use Committee rules were followed.

Immunohistochemistry and FACS Analysis

CD70 was assessed using the mouse monoclonal anti-CD70 antibody (Santa Cruz). Other immunohistochemical staining was performed for CD3, CD4, CD8 (Zhongshan), and CD27 (Abcam). Three independent pathologists counted the positive cells in 8-10 randomized high-power fields of each sample. For the fluorescence activated cell sorting (FACS) analysis, anti-human and mouse CD8, CD4, CD3, and CD70 (BD Biosciences) were used.

CD70 GBM Lines

Lentiviral gene constructs encoding human CD70 and controls (pD2109-EF1a-CD70, pD2109-EF1a vector) or CD70 short hairpin (sh)RNA and controls (pLK0.1-puro-CD70-shRNA, pLKO.1-puro-nt-shRNA)[14] were transduced into GBM lines. pLenti-CMV-Puro-Luc (gift from Eric Campeau, Addgene plasmid #17477) was used in the transduction of U87 (U87.Luc). Murine glioma lines GL261 and KR158B were transduced with lentiviral constructs containing mouse CD70 gene or vector control (pUltra-EGFP-CD70-Luc or pUltra-EGFP-Luc), designated as GL70 or KR70. The CD70+ clone was achieved by single cell sorting using a flow cytometer, and the bulk CD70+ cells were from nonselected cells. The backbone Ultra was a gift from Malcolm Moore (Addgene plasmid #24129). All lentiviruses were produced with packaging plasmid psPAX2 and envelope plasmid pMD2.G (gifts from Didier Trono, Addgene plasmid #12260 and #12259).

RNA Sequencing and Data Analysis

Triplicated RNA products of 5 CD70 manipulated conditions of the pGBM #3 line were sent for RNA sequencing (RNA-seq) (Novogene). For the data analysis, clean data were provided by the company; paired-end reads were mapped to the human genome (version GRCh37/hg19) and assembled by TopHat Alignment and Cufflinks Pipeline from Illumina BaseSpace as a default setup. Data from The Cancer Genome Atlas (TCGA) used in this study were downloaded from <https://cancergenome.nih.gov/>. Gene expression by RNA-seq (IlluminaHiSeq version 2) was used.

CAR Transduction of Human and Mouse T Cells

The pMSGV8-hCAR and pMSGV8-mCAR generations and T-cell transductions were described previously.[19] We added a tdTomato as a CAR tracker following the CD3-zeta by employing self-cleaving 2A peptide. Nontransduced (NT) T cells were activated under the same conditions. Mouse T-cell transduction was performed using the same methodology as the human T cell transduction. T cell transduction efficiency was determined by tdTomato-positive cells.

Real-Time PCR

Real-time PCR was performed using the SsoAdvanced Universal Probes Supermix (Bio-Rad Laboratories) and run on a CFX96 Touch Real-Time PCR Detection System (Bio-Rad). The primers and probes were purchased from Thermo-Fisher Scientific. RPL13A was used for normalization.

CAR T-Cell Tumor Recognition

Human or mouse CAR T cells were cocultured with human or mouse glioma cell lines, respectively. Cell culture supernatants were harvested and assayed for interferon (IFN)-γ 18 h later. For the specific lysis assays, luciferase expressing tumor targets were cocultured with varying amounts of mCD70 CAR T cells or NT T cells, respectively.[20] Luminescence was measured in a Cytation 3 Cell Imaging Multi-Mode Reader (BioTek).

Syngeneic and Xenograft Mouse Models and Bioluminescence Imaging

For the syngeneic model, KR70 tumor cells were inoculated into the brains of C57BL/6J mice (Jackson Laboratory), and mCAR or NT T cells were delivered systemically via tail-vein injection. All mice were preconditioned with 5 Gy total body irradiation to induce lymphodepletion. In the human xenograft model, U87.Luc cells were implanted into the brain of NSG-B2m mice (NOD.Cg-B2m$^{tm1Unc}$Prkdc$^{scid}$Il2rg$^{tm1Wjl}$/SzJ) (Jackson Laboratory), and hCAR or NTT cells were delivered systemically via tail-vein injection. To monitor tumor growth, animals were imaged using the IVIS system (Xenogen). The bioluminescence image was analyzed using Living Image software (Caliper Life Sciences).

Statistical Methods

We considered CD70 as a continuous predictor of survival. Because of the observational nature of our study survival data, we also included variables in each model to account for possible confounding, and we included sex and age in all patient models. We used restricted cubic splines to assess possible nonlinearity in the association of continuous predictors with survival. We transformed all continuous predictors to a log base 2 scale before inclusion in our models. We used our fitted Cox models to estimate adjusted hazard ratio (HR) for CD70 and other included predictors along with 95% confidence intervals and Wald tests for the null hypothesis HR=1. We estimated median survival in a similar manner for selected levels over the range of observed CD70 levels. We used these estimates to generate a median survival trend curve for CD70. *P<0.05, P<0.01, *P<0.001.

Results

Figure 18:
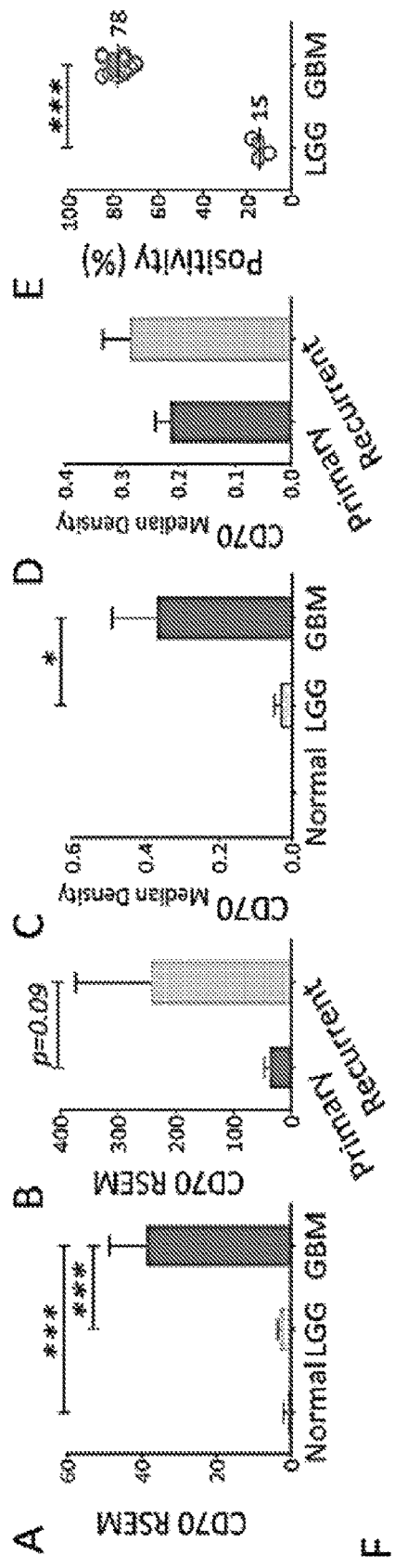
FIGS. 18(A)-18(F) illustrate overexpression of CD70 on primary and recurrent gliomas, but not on tumor infiltrating T cells according to one embodiment of the present disclosure.

Overexpressed CD70 is Presented on Primary and Recurrent Gliomas, but Not on Tumor Infiltrating T Cells We and others have shown that T-cell senescence, characterized by CD27 loss and telomere shortening, is a signature of tumor-associated immune erosion.[21] We sought to determine the expression profile of CD70 in patients with primary low-grade gliomas (LGGs) and GBMs. Using RNA-seq data culled from TCGA, we detected no CD70 in normal brains, but a significant CD70 upregulation was observed in both primary LGGs and GBMs; notably, primary and recurrent GBMs expressed the highest levels of CD70 (FIG. 18A-B and FIG. 24A-C). FIG. 18 is an overexpression of CD70 on primary and recurrent gliomas, but not on tumor infiltrating T cells. (A-B) Differential CD70 gene expression in normal brain, primary and recurrent LGG, and GBM. The gene expression level was defined as RSEM (RNA-seq by expectation-maximization), and patient's informations were culled from TCGA RNA-seq datasets. (C) Protein level of CD70 was evaluated by immunohistochemistry using tumors from primary LGGs (n=41), GBMs (n=44), and normal brains (n=7). (D) CD70 protein expression between primary and recurrent GBMs. Tumors from 7 paired GBMs before and after recurrence were evaluated. (E) The CD70 positivity within each CD70-expressing primary GBM. (F) Determination of CD70 expression on tumor and T cells. Seven CD70+ GBMs were co-stained with fluorescent conjugated CD3 (green) and CD70 (red) antibodies; 4',6'-diamidino-2-phenylindole was used for nuclear staining. Representative pictures (with an enlarged overlaid area) from one tumor are shown. Mann-Whitney Utest was used.

For protein expression, regular or fluorescent immunohistochemistry staining was carried out using surgical resected primary and recurrent LGGs and GBMs. A significantly elevated expression in patients with GBM primary and recurrent tumors was observed (FIG. 18C-D). Heterogeneous expression was observed on the surface and/or within the cytoplasm of the positive tumor cells, and no CD70 expression was observed on endothelial cells of the microvascular proliferation. Many GBMs demonstrated diffuse strong membranous and cytoplasmic staining and an average of 78% positivity in each CD70-expressing primary GBM; expression in LGGs was limited to about 15% (FIG. 18E). Since activated T cells potentially express CD70, we wanted to determine if these T cells also contribute to CD70 positivity. Dual-colored staining of CD3 and CD70 was performed in CD70+ patients' samples. Overlaid images in these samples demonstrated that CD70 expression was limited to tumor cells and was not on infiltrating T cells (FIG. 18F). While 35% of primary GBMs were CD70+, only 10% of the primary LGGs tested expressed CD70. Compared with recurrent LGGs, which displayed 17% CD70 expression, 69% of recurrent GBMs expressed CD70.[37] To confirm that CD70 was a tumor-specific target, we evaluated CD70 gene expression in all 52 normal tissue types (total 8555 samples from different organs, including 1259 brain tissues) and Epstein-Barr virus (EBV)-transformed B cells using an RNA-seq database culled from GTEx Portal. Based on these analyses, only the EBV-transformed B cells showed significant expression of CD70; CD70 levels from normal samples were nondetectable.[37] These results indicate that CD70 is a glioma target for the development of novel therapeutic strategies.

Figure 19:
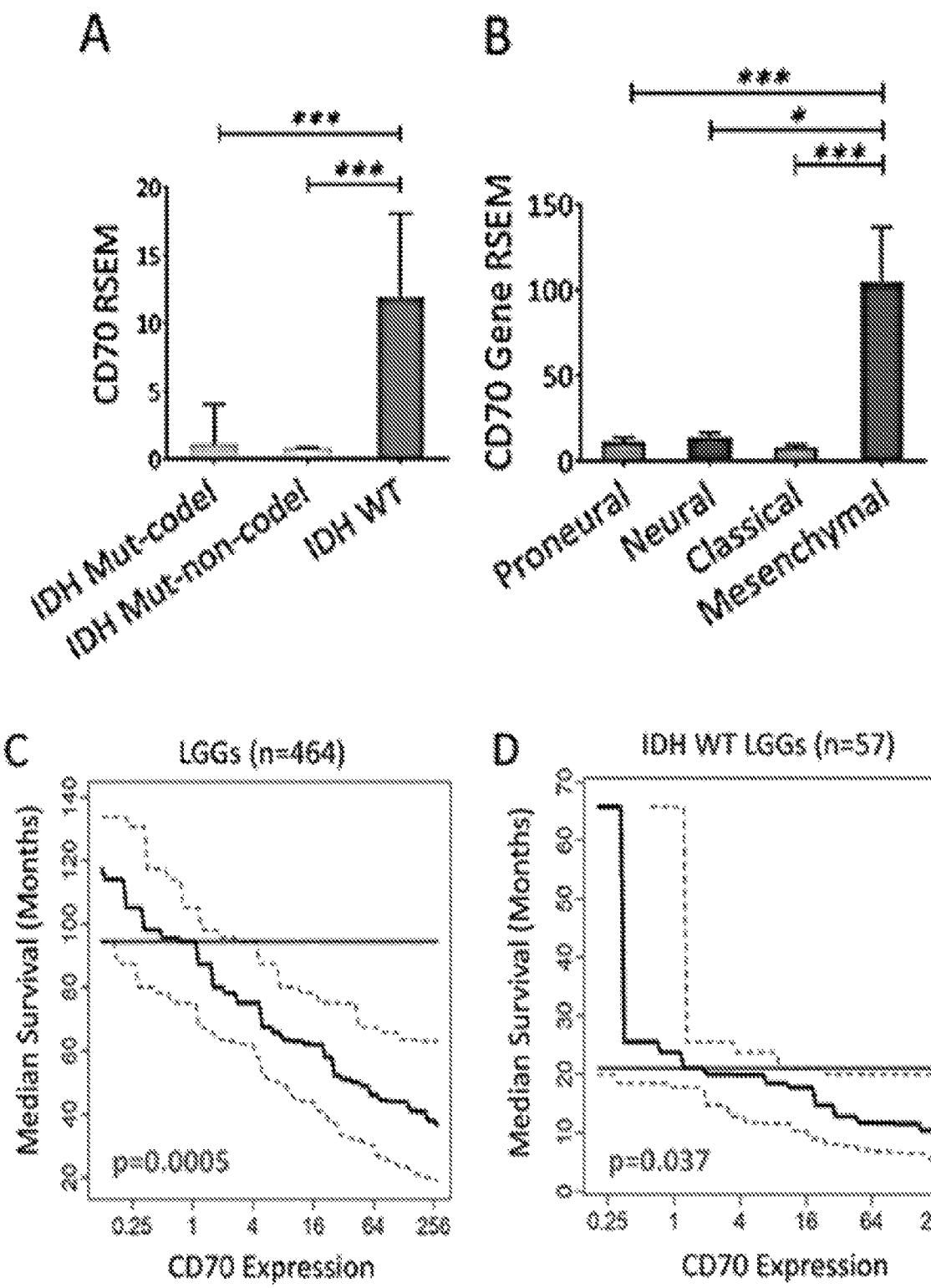
FIGS. 19(A)-19(G) illustrate CD70 gene expression is inversely correlated with overall survival in patients with primary gliomas according to one embodiment of the present disclosure.
Figure 19:
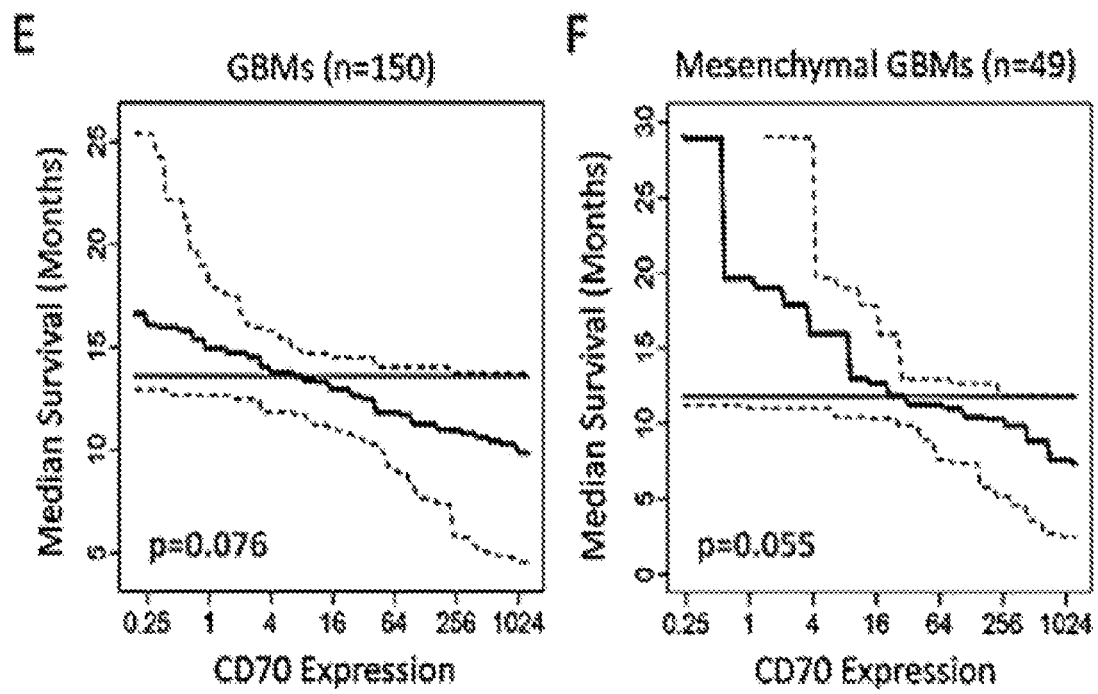

CD70 Expression Correlates with Poor Survival for Patients with LGGs and Mesenchymal GBMs To understand the effects of CD70 expression in gliomas on clinical outcomes, we utilized existing large RNA-seq datasets and determined the association between CD70 gene expression and survival based on molecular classifications.[22,23] FIG. 19 illustrates CD70 gene expression is inversely correlated with overall survival in patients with primary gliomas. (A-B) CD70 expression among different subgroups of LGGs and GBMs. (C-F) Predicted median overall survival decreases with increasing CD70 expression in primary LGGs, IDH wild-type LGGs, GBMs, and GBMs in the mesenchymal subgroup. CD70 RNA-seq expression was considered as a continuous predictor of survival, adjusted for gender and age in all subgroup models using Cox proportional hazards (PH) regression; further adjustment was made for tumor subtype in the GBM subgroup model). (G) Summary of differential median overall survival between CD70 high and low groups defined by mean values of CD70 RSEM in LGGs and GBMs (subgroup median survival estimates adjusted for age, gender and GBM tumor subtype via CoxPH regression).

In primary LGGs, CD70 was predominantly expressed by isocitrate dehydrogenase (IDH) wild-type tumors compared with IDH mutated tumors, including both chromosome 1p/19q codeletion and non-codeletion (FIG. 19A). In GBM, CD70 was overexpressed in tumors with mesenchymal gene signatures (FIG. 19B). Since CD70 has been shown to assist T-cell function,[14] we assessed whether CD70 could be a favorable prognostic factor in gliomas. CD70 expression levels were culled from TCGA and correlated with survival outcomes. In LGGs, elevated CD70 tumor expression was significantly associated with decreased overall survival. The median overall survival for patients with elevated CD70 expression (above the median expression level) was only 26.7 months, compared with 94.5 months for patients in the CD70-low group (below median) (69.8 mo difference, P=0.0005; FIG. 19C). Because wild-type IDH status is associated with poor survival, we evaluated the correlation between CD70 expression levels and survival outcomes in this population. Indeed, CD70 was found to be inversely associated with patient survival (13.8 mo difference, P=0.037; FIG. 19D). The same trends were revealed for patients with GBM (3.5 mo difference, P=0.076), specifically mesenchymal subtypes[23] (5.5 mo difference, P=0.055; FIG. 19E-F). In summary (FIG. 19G), these data suggest that CD70 expression on tumor cells is negatively associated with patients' survival in LGGs and GBMs.

CD70 is Directly Involved in Chemokine/Cytokine Signaling Pathway in Primary GBM FIG. 20A-H illustrate that CD70 is involved in cytokine/chemokine productions in GBM. (A-B) CD70 overexpression influences the cytokine/chemokine pathway in a primary GBM line. Triplicated RNA samples from pGBM #3 (CD70+) were transduced with CD70 (Over-exp) or lentiviral vector control (blank), confirmed by gene (fragments per kilobase of transcript per million mapped reads, FPKM) and protein expression (flow cytometry). Gene enrichment of the upregulated gene list (Over-exp vs blank) was performed by PANTHER-Pathway; a volcano plot and the top-ranked pathways are shown. (C) Primary GBM lines secrete various chemokines. Culture supernatants from the primary lines were collected 8 days after the tumors were seeded, and chemokine array was performed. (D-G) Gene expression changes between overexpression and silence of CD70 in pGBM #3 were evaluated by real-time quantitative PCR. (H) IL-8 secretion was measured by enzyme-linked immunosorbent assay. Unpaired t-test was used.

Figure 20:
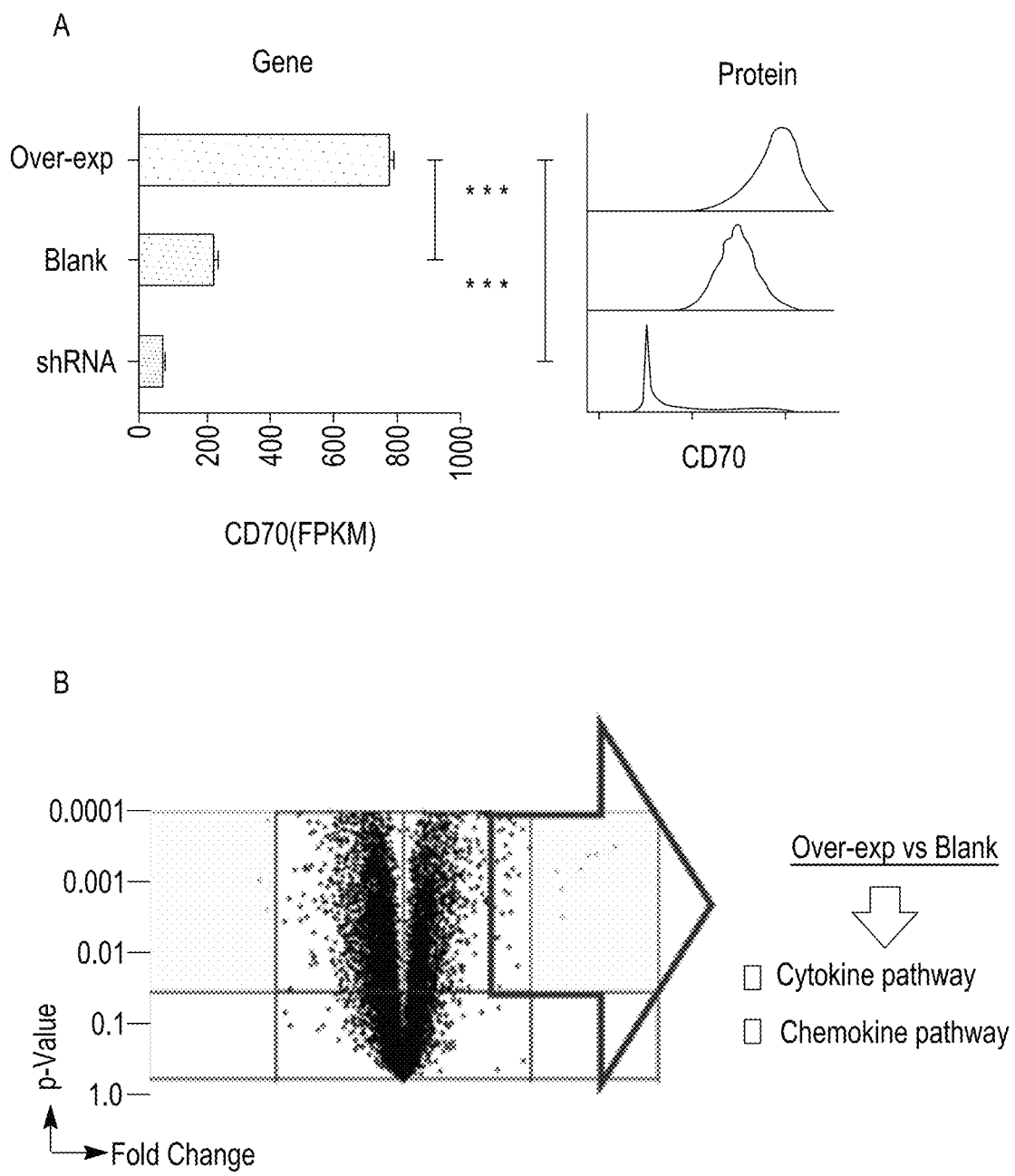
FIGS. 20(A)-20(H) illustrate CD70 being involved in cytokine/chemokine productions in GBM according to one embodiment of the present disclosure.
Figure 20:
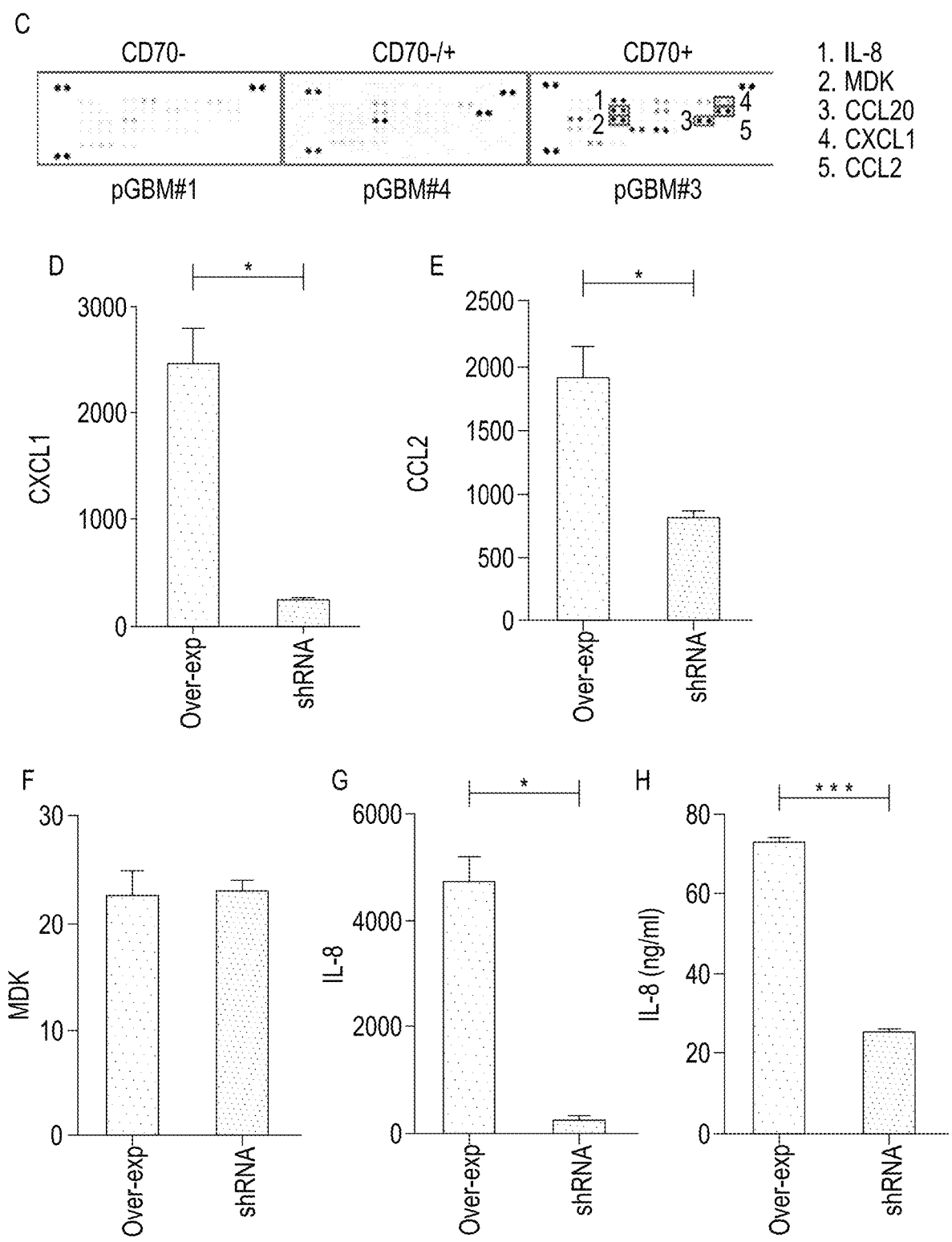

To better understand the mechanism of action for CD70 in gliomas, we did pathway enrichment analysis using a TOGA RNA-seq dataset, which indicated the involvement of CD70 in chemokine/cytokine signaling pathways.[24] Since the analysis from TOGA samples illustrated entire tumor tissues that contained immune infiltrates, we next wanted to determine if CD70 directly affects the chemokine/cytokine pathway in pure tumors. We investigated chemokine/cytokine pathway changes in a primary CD70+ line (pGBM #3) after manipulating the CD70 gene (FIG. 20A). We confirmed that CD70 overexpression enhanced these genes in the chemokine/cytokine pathways (FIG. 20B). Additionally, CD70+ primary GBM lines elicited greater amounts of chemokines in cell culture supernatants, including interleukin (IL)-8, midkine (MDK), chemokine C-C ligand (CCL)20, C-X-C motif chemokine ligand (CXCL)1, and CCL2 (FIG. 20C). The gene levels of the chemokines (IL-8, CXCL1, CCL2, MDK) were abrogated by CD70 silencing (FIG. 20D-G). Additionally, the protein levels of IL-8 were significantly reduced when the CD70 gene was silenced (FIG. 20H). These data suggest that CD70 is directly involved in glioma tumor chemokine productions.

Figure 21:
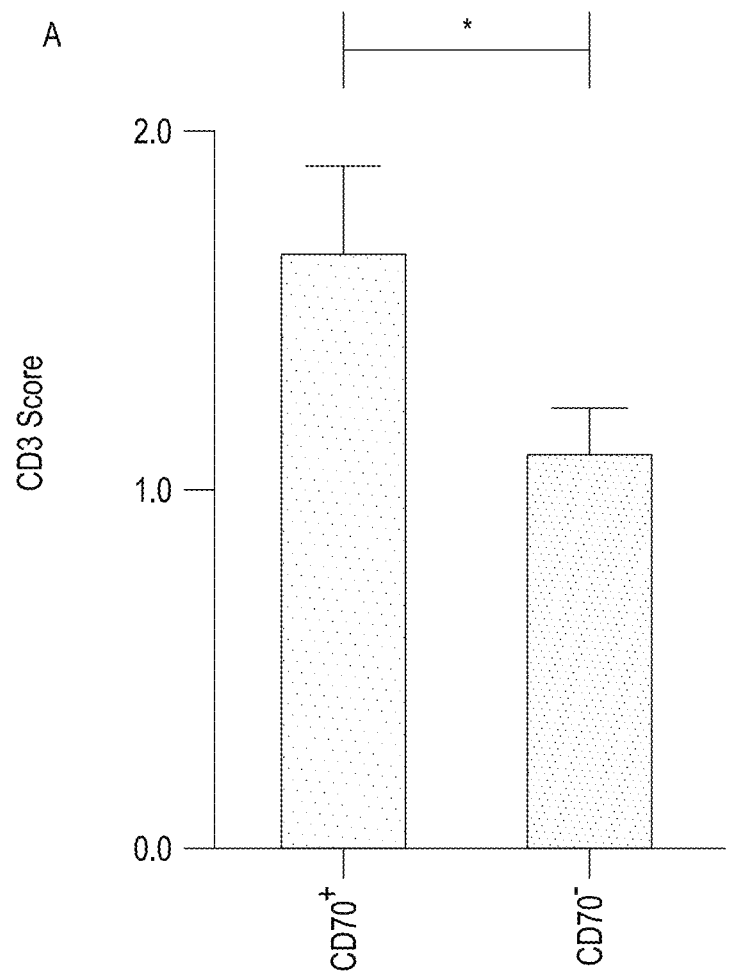
FIGS. 21(A)-21(C) illustrate that CD70 is associated with T-cell infiltration and CD8+ T-cell death in GBM according to one embodiment of the present disclosure. In the bar graphs of FIG. 21(B), the top most bar is PBMC only, the second bar represents shRNA, the third bar represents overexpression, and the bottom bar represents blank, for each of PBMC3, PBMC2, and PBMC1.

CD70 Associates with Enhanced Tumor T-Cell Infiltration and Induction of Selective CD8+ T-Cell Death FIG. 21 illustrates that CD70 is associated with T-cell infiltration and CD8+ T-cell death in GBM. (A) Relative higher numbers of infiltrating CD3+ T cells in CD70+ compared with CD70− tumors. Paraffin-embedded GBM tumor samples described in FIG. 1 were analyzed by immunohistochemistry for CD70 and CD3, respectively, using serial slides. (B) CD70 predominantly induces CD8+ T-cell death after engaging tumor cells. CD70− manipulated pGBM #3 cells were cocultured with 3 allogeneic PBMCs obtained from healthy donors. Fluorescence activated cell sorting (FACS) analysis was performed 14 days after the coculture (left). The cell death of T-cell subsets was quantitated by propidium iodide (PI) staining for both CD4+ and CD8+ T cells (right). These results were representative of 4 individual experiments. Mann-Whitney test was used to assess statistical significance. (C) The ratio of CD4+ to CD8+ T cells among the cocultured T cells. FACS analysis from (B) was also evaluated by CD4+ to CD8+ ratio, and the gating strategy is shown in the upper panel. Paired t-test was used to assess statistical significance.

Tumor-derived chemokines have been shown to recruit macrophages and T cells into the tumors.[25,26] Having demonstrated a direct connection between CD70 and tumor associated chemokine production, we sought to assess the association of CD70 with T-cell infiltration. We found that CD70 was moderately associated with tumor infiltrating CD3+ T cells in primary GBMs (FIG. 21A). To more broadly interrogate T-cell infiltration in primary GBMs, a large dataset culled from TOGA was analyzed, and a predilection for CD4 over CD8 transcripts (~29-fold higher) was revealed in primary gliomas. These data suggest that diminished CD8 transcripts in GBMs may represent tumor immune erosion. To further determine the impact of CD70-expressing tumor cells on T cells, allogeneic PBMCs were cocultured with GBM lines, which expressed various levels of CD70 using forced overexpression or shRNA knockdown (described in FIG. 21A). Interestingly, no major cell death was found in the CD4+ T-cell population, but CD8+ T cells displayed a significant level of cell death as measured by propidium iodide (PI) staining. Silencing CD70 significantly reduced CD8+ T-cell death. Although there were large variations in PI+ CD8+ T cells across PBMC samples, the trend was greater for CD8+ versus CD4+ T-cell death, and an increased CD4+ to CD8+ T cell ratio was consistently observed (FIG. 21B-C). Together, these data suggest that CD70 on gliomas may help recruit T cells into the tumor but also induce CD8+ specific cell death in part through direct cell contact.

Glioma Recognitions of Human and Mouse CD70CAR T Cells In Vitro

To explore whether the restricted expression of an immunosuppressive ligand on GBM tumor cells could serve as a novel target for immunotherapy, CD70-specific CAR constructs of human and mouse were made. The human CD70 CAR (hCD70-CAR, MSGV8 [(MSGV1-(Bam-)]-human CD27-4-1 BB-CD3-zeta) is a retroviral-based vector that encodes CD27 for antigen recognition and transmembrane domains followed by intracellular portions of the 4-1 BB and the CD3-zeta chain.[19]

Figure 22:
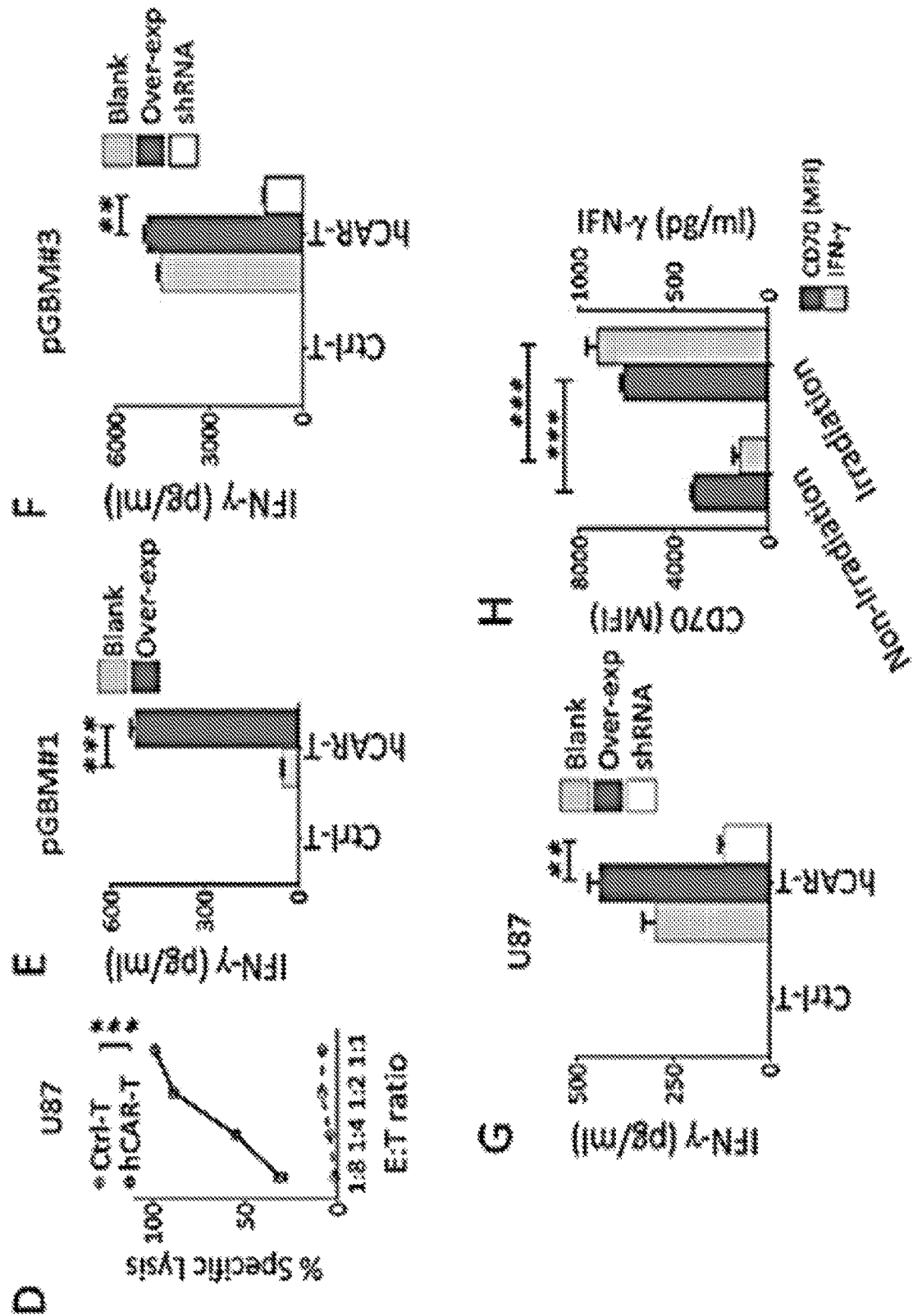
FIGS. 22(A)-22(M) illustrate tumor recognitions of gliomas by human and mouse CD70 CAR T cells according to one embodiment of the present disclosure.
Figure 22:
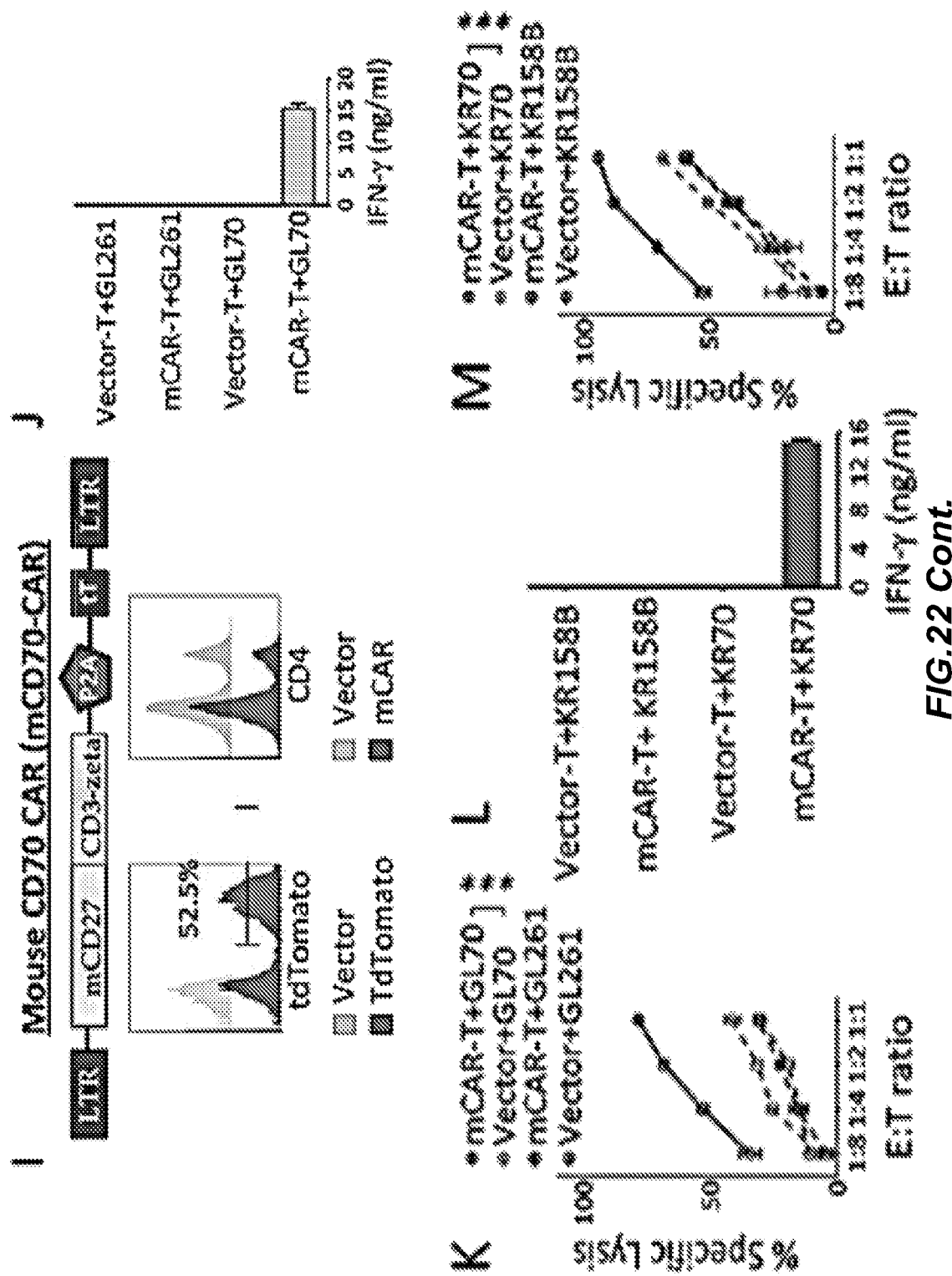

FIG. 22 illustrates tumor recognitions of gliomas by human and mouse CD70 CAR T cells. (A) Human CAR construct and its transduction efficiency in human T cells. The transduction efficiency was measured by tdTomato positive cells and the frequency of CD4+/CD8+ T cells 4 days posttransduction are shown. (B) GBM targets for hCAR T cells. GBM lines naturally expressing various levels of CD70 were tested for the CD70 surface expression by FACS. (C-D) Recognition of these lines by hCAR T cells.

The recognitions were measured by IFN-γ release and cytotoxic killing assay. (E-G) Manipulation of tumor CD70 expression alters the CAR T cells recognition. The tumor lines were cocultured with manipulated GBM lines by either overexpressing or silencing CD70. (H) Irradiation enhances tumor CD70 expression and CAR T-cell recognition. The U87 line was irradiated with 6 Gy, CD70 expression was determined by FACS on day 3 and then cocultured with CAR T cells. (I) Transduction of mCD70 CAR to mouse T cells. Construct of mouse CD70-specific CAR (mCD70-CAR), transduction efficiency determined by tdTomato and frequency of CD4+/CD8+ T cells in the mCAR T cells 4 days posttransduction are shown. (J-M) CD70-overexpressed murine glioma lines were recognized by mCD70-CAR T cells. The tumors (104) were cocultured with (104) mCD70-CAR T cells or vector/NT control T cells, respectively. For the killing assay, various ratios of effector to target (E:T) were respectively cocultured. Unpaired t-test was used.

We added tdTomato sequences following the CD3-zeta linked by P2A (the MSGV8 vector was used as a control). Based on tdTomato expression, we obtained >50% of T-cell transduction efficiency, and the majority of the transduced T cells were CD8+. CAR transduction did not significantly alter the ratio of CD4+/CD8+ T cells when the transduced and NT T cells were compared (a representative case is shown in FIG. 22A). Using both primary and commercial GBM lines that do or do not naturally express CD70 (FIG. 22B) as hCD70-CAR T cell targets, we showed that hCD70-CAR T cells recognize only CD70+ lines, but not CD70-negative lines; no recognition was found by NT or vector-transduced control T cells, as measured by IFN-γ release and cytotoxic killing assay (FIG. 22C-D). Overexpression or knockdown of CD70 enhanced or diminished, respectively, recognition by the CD70 CAR T cells (FIG. 22E-G). Irradiation of CD70+ tumors enhanced their CD70 expression and recognition by CAR T cells (FIG. 22H). A similar approach was also carried out for the murine GBM lines. The murine-derived CD70 CAR (mCD70-CAR), MSGV8 [(MSGV1-(Bam-)]-mouse CD27-CD3-zeta was the same retroviral vector used for the hCAR, but it contains a mouse's full-length CD27 and CD3-zeta chain[19] (tdTomato was added after the CD3-zeta by 2A peptide). The transduction efficiencies were generally >50% in our experiments (a representative analysis is shown in FIG. 22I). We next determined the tumor-specific recognition against CD70 transduced murine glioma lines GL70 and KR70 by INF-γ production and cytotoxic killing assay, respectively. We demonstrated that mCD70-CAR T cells were able to kill CD70+ targets in vitro (FIG. 22J-M). These results demonstrated that both human and mouse CD70 CAR T cells recognize CD70+ glioma targets specifically.

Antitumor Response of CD70 CAR T Cells Against CD70+ Gliomas In Vivo

Figure 23:
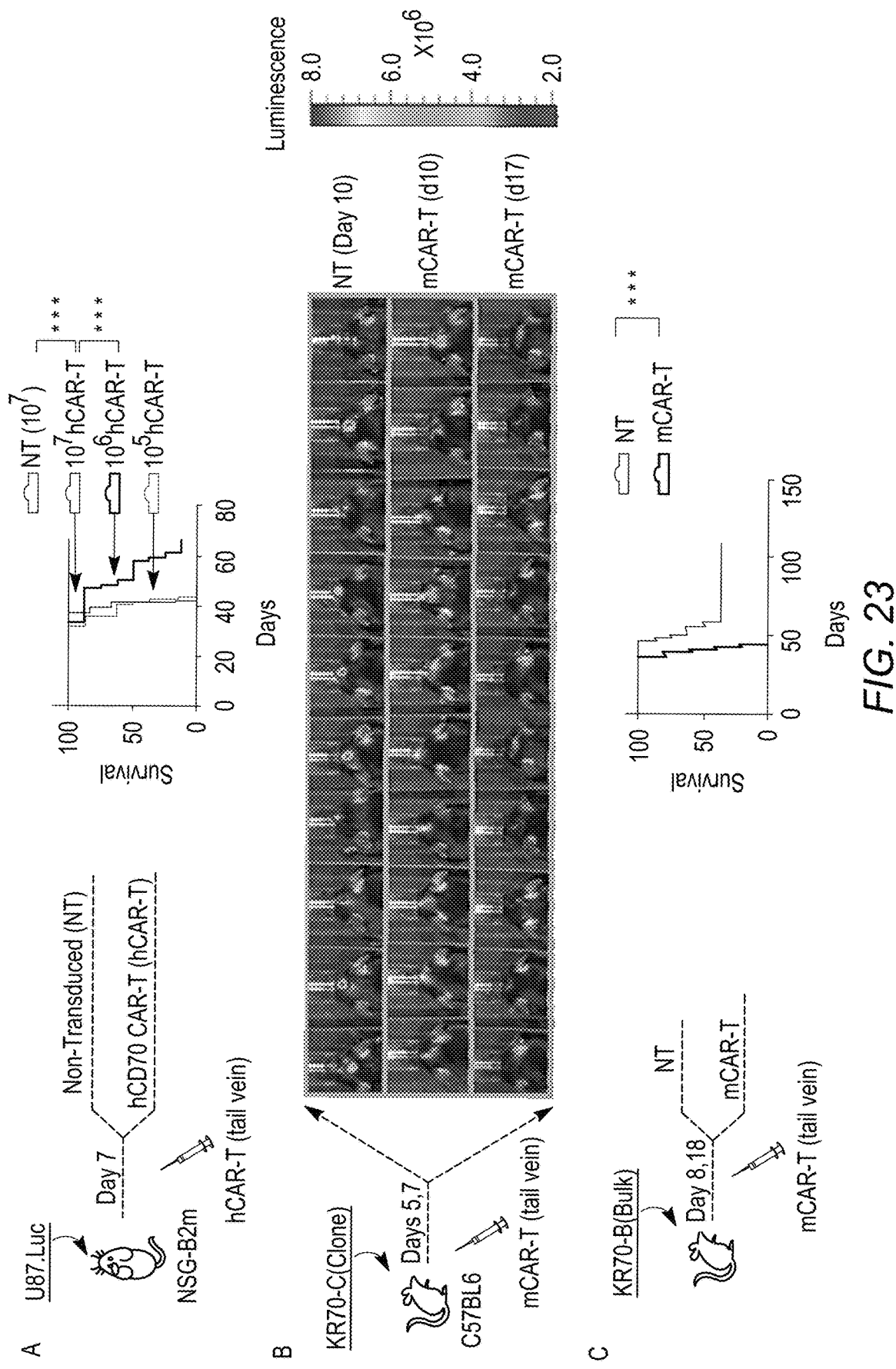
FIGS. 23(A)-23(C) illustrate antitumor response of CD70 CAR T cells against CD70+ gliomas in vivo according to one embodiment of the present disclosure. In the line graph of FIG. 23(C), the line extending to 100 days corresponds to mCAR-T.

FIG. 23 illustrates antitumor response of CD70 CAR T cells against CD70+ gliomas in vivo. (A) Antitumor response of hCAR T cells in human xenograft glioma model. CD70+ (U87.Luc, 5×104/mouse) tumor-bearing (confirmed by imaging 6 days after tumor inoculation) mice were adoptively transferred through tail-vein injection with NT or various doses (105-107/mouse, 8/group) of hCAR T cells 7 days after the tumor implantation. (B-C) A complete response and prolonged survival induced by mCAR T cells in syngeneic glioma models. Two models were used: groups of 6-8 weeks C57BL/6J mice (10/group) were intracranially inoculated with 1×10$^5$ KR70 tumor cells derived from a tumor clone, designated as KR70-C, and then adoptively transferred (1×10$^7$) NT or mCAR T cells on days 5 and 7 post tumor implantation. Luciferase imaging was carried out 10 and 17 days after the tumor implantation. The same experiment described in (B) was performed, except the inoculated tumor cells were derived from bulk tumors, KR70-B. All experiments were repeated at least 2 times. Mann-Whitney test and the log-rank test were used.

Next, human and mouse CARs in human xenograft and syngeneic orthotopic glioma models was tested. For hCAR, various doses (10$^5$-10$^7$/mouse) of the CAR T cells were adoptively transferred into tumor-bearing NSG-B2m mice 7 days after tumor inoculation. The results demonstrated a T cell dose-dependent manner: a complete regression was seen in 10$^7$/mouse, an intermediate effect in 10$^6$/mouse, and no effect in the 10$^5$/mouse group in survival (FIG. 23A). Since the NSG-B2m mice lacked major immune cell components, we also made a mouse version of CD70 CAR and tested it in C57BL/6J syngeneic mice. Due to the heterogeneous nature of gliomas, we employed 2 types of CD70-overexpressing glioma cells: (i) tumors derived from a single clone of a CD70+ glioma cell line, KR70-C; and (ii) inoculated nonselective bulk CD70-expressing tumors, KR70-B, which expressed various levels of CD70 (~70% positivity for CD70). Complete tumor regressions were observed in KR70-C tumor-bearing mice 17 days after tumor implantation (FIG. 23B). Significantly prolonged survival was observed in the CAR T treated group of KR70-B tumor-bearing mice compared with the NT T cell treated group, and 38% of the mice were cured by CAR T cells (P<0.001, HR=3.5, FIG. 23C). No adverse effect was observed in these models, confirming CAR safety in vivo.[19] In summary, CD70-specific CAR T cells generate potent antitumor response against CD70+ gliomas in xenograft and syngeneic animal models.

Discussion

Identifying molecular targets that contribute to tumor pathogenesis with restricted specificity to tumor expression is crucial for effective and sustained therapy. The tumor microenvironment in GBM is notoriously immunosuppressive and appears co-opted in part by CD70 tumor overexpression. We found in a recent study that CD70 is involved in promoting tumor migration and M2 macrophage infiltration in GBM.[24] In this report, we showed that CD70 protein was overexpressed by subgroups of primary LGG (10%) and GBM (35%). No CD70 was detected on tumor infiltrating CD3+ T cells and CD163+macrophages in these tumors.[24] Importantly, little to no expression was detected in all 52 types of normal tissue, including peripheral blood. These results indicate that CD70 expression is mostly restricted to tumors. The gene expression of CD70 was predominantly found in IDH wild-type LGG patients, a subgroup with strikingly similar molecular characteristics and overall survival to GBMs.[27] CD70 was associated with poor survival outcomes in IDH wild-type LGGs. CD70-expressing GBMs were mainly observed in the mesenchymal subgroups and were negatively associated with survival, suggesting that CD70 may have a vital role in glioma progression.

Since CD70 is the only known ligand for CD27 (a T cell co-stimulatory receptor that plays a critical role in activation, effector function, and survival of T cells), we initially thought that glioma-CD70 expression would impact tumor infiltrating T-cell function via CD27 signaling. Unexpectedly, we found no downregulation of CD27 on tumor infiltrating lymphocytes (data not shown), suggesting that a CD27-independent mechanism has taken place. Although CD70 expression on primary GBMs positively correlates with tumor infiltrating lymphocytes, several obstacles may potentially prevent these T cells from mounting a strong antitumor response. These obstacles include: (i) overwhelming presentation of M2 macrophages that may stymie T-cell function; (ii) the possibility that promoting regulatory T cells, which we have shown, act as a predictor of tumor progression (Mu L et al, manuscript submitted), will utilize the CD27/CD70 axis; and (iii) inducing CD8+ specific T-cell death through a novel mechanism involving the epiregulin-epidermal growth factor receptor pathway (unpublished data). The studies described herein provide scientific evidence that targeting CD70-expressing gliomas offset the immunosuppressive effect and promote strong and sustained antitumor responses.

Several immunotherapeutic approaches targeting CD70 in other malignancies have been reported, such as antibody blockade, antibody-dependent cell-mediated cytotoxicity, and CAR T cells for cancers such as lymphoma and renal carcinoma.[28,29] Due to the existence of the blood-brain barrier in gliomas, CAR T therapy is a superior strategy to other methods, as activated T cells are not only able to pass through the barrier, but are also capable of inducing a potential antitumor response.[30-32]

Our results illustrate that CD70 is highly expressed not only by primary tumors, but also by recurrent tumors, which presents a consistent therapeutic target for primary and recurrent gliomas. In addition, irradiation enhances CD70 expression on tumors, providing good opportunity to enhance antitumor efficacy to combine standard care with CD70 CAR therapy in glioma patients. The impact of CD27 on T-cell activation depends (in part) on the extracellular domain of membrane-bound CD27 (soluble [s]CD27), such that addition of sCD27 into T-cell cultures promotes strong T-cell proliferation.[33] Thus, introducing the extracellular motif could potentially enhance the CAR T-cell function. Nevertheless, we demonstrated that CD70-specific human and murine CAR T cells induce complete regression/improved survival in CD70+ gliomas in both xenograft and syngeneic models without toxicity.

Toxicity is one of the great obstacles for CAR T therapy. Since inherited deficiency of CD70 (i.e., homozygous mutations in CD70) may cause impaired function in immune response to viral infections,[34,35] there is concern that targeting CD70 may induce immunosuppression. However, adverse effects from CD70 deficiency may be distinct from adverse effects mediated by CD70 CAR T-cell targeting. While the effects of CD70 CAR T-cell targeting on progenitor cells remain to be determined, based on previously published data, CD70 CAR T-cell targeting does not appear to affect dendritic or T cells. CD70 expression is limited only to the most activated immune cells, which are relatively sparse in cancer patients.[14,36] This study showed that CD70 CAR T cells potently induce antitumor reactivity against CD70+ gliomas, both in vitro and in vivo. Taken together, our data suggest that CD70 may be harnessed as an immunotherapeutic target to improve outcomes in patients with gliomas.

Example 3

Sequences

```
SEQ ID NO: 1-Human CD70CAR-CXCR1 2297 bp
                                                           (SEQ ID NO: 1)
   1 CCATGGCAAG ACCCCACCCC TGGTGGCTGT GTGTGCTGGG CACACTGGTC GGACTGAGCG

61 CCACCCCTGC CCCTAAGAGC TGCCCCGAGA GACACTACTG GGCTCAGGGC AAGCTGTGCT

121 GCCAGATGTG CGAGCCCGGC ACCTTCCTGG TGAAAGACTG CGACCAGCAC CGGAAGGCCG

181 CCCAGTGCGA TCCTTGCATC CCCGGCGTGT CCTTCAGCCC CGACCACCAC ACCAGACCCC

241 ACTGCGAGAG CTGCCGGCAT TGCAACTCTG GCCTGCTGGT CCGCAACTGC ACCATCACCG

301 CCAACGCCGA GTGCGCCTGC AGAAACGGCT GGCAGTGCCG GGACAAAGAA TGCACCGAGT

361 GCGACCCTCT GCCCAACCCC AGCCTGACCG CCAGAAGCAG CCAGGCTCTG AGCCCTCACC

421 CTCAGCCCAC CCATCTGCCC TACGTGTCCG AGATGCTGGA AGCCCGGACA GCCGGCCACA

481 TGCAGACCCT GGCCGACTTC AGACAGCTGC CCGCCAGAAC CCTGAGCACC CACTGGCCTC

541 CCCAGCGGAG CCTGTGCAGC AGCGACTTCA TCCGGATCCT GGTGATCTTC AGCGGCATGT

601 TCCTGGTGTT CACCCTGGCT GGCGCCCTGT TCCTGCACAA GCGGGGCAGA AAGAAGCTGC

661 TGTACATCTT CAAGCAGCCC TTCATGCGGC CCGTGCAGAC CACCCAGGAA GAGGACGGCT

721 GCAGCTGCCG GTTCCCCGAG GAAGAGGAAG GCGGCTGCGA GCTGAGAGTG AAGTTCAGCA

781 GAAGCGCCGA CGCCCCTGCC TACCAGCAGG GCCAGAACCA GCTGTACAAC GAGCTGAACC

841 TGGGCAGACG GGAAGAGTAC GACGTGCTGG ACAAGCGGAG AGGCCGGGAC CCTGAGATGG

901 GCGGCAAGCC CCAGAGGCGG AAGAACCCTC AGGAAGGCCT GTATAACGAA CTGCAGAAAG

961 ACAAGATGGC CGAGGCCTAC AGCGAGATCG GCATGAAGGG CGAGCGGCGG AGAGGCAAGG

1021 GCCACGATGG CCTGTACCAG GGCCTGAGCA CCGCCACCAA GGACACCTAC GACGCCCTGC

1081 ACATGCAGGC TCTGCCTCCA AGATTAATTA ACCGTGCCAA GCGAGGTAAG CCTATCCCTA
```

-continued

```
1141 ACCCTCTCCT CGGTCTCGAT TCTACGGGAT CCGGAGCCAC GAACTTCTCT CTGTTAAAGC

1201 AAGCAGGAGA CGTGGAAGAA AACCCCGGTC CTTTCGAAAT GAGCAACATC ACGGACCCGC

1261 AGATGTGGGA CTTCGACGAC CTGAACTTCA CCGGCATGCC TCCAGCCGAC GAGGATTACA

1321 GCCCTTGCAT GCTGGAAACC GAGACACTGA ACAAATACGT GGTCATCATT GCCTACGCTC

1381 TGGTGTTCCT GCTGAGCCTG CTGGGCAATA GCCTGGTCAT GCTGGTCATC CTGTACAGCA

1441 GAGTGGGCAG ATCCGTGACC GACGTGTACC TGCTGAATCT GGCCCTGGCC GATCTGCTGT

1501 TTGCCCTGAC ACTGCCTATT TGGGCCGCCA GCAAAGTGAA CGGCTGGATC TTCGGCACCT

1561 TCCTGTGCAA GGTGGTGTCT CTGCTGAAAG AAGTGAACTT CTACAGCGGC ATCCTGCTGC

1621 TGGCCTGCAT CAGCGTTGAC AGATACCTGG CCATCGTGCA CGCCACCAGA ACACTGACCC

1681 AGAAGAGACA CCTGGTCAAG TTCGTGTGCC TCGGCTGTTG GGGCCTGAGC ATGAATCTGT

1741 CTCTGCCATT CTTCCTGTTC CGGCAGGCCT ACCATCCTAA CAACAGCAGC CTGTGTGCT

1801 ACGAGGTGCT GGGAAACGAT ACAGCCAAGT GGCGGATGGT GCTGCGGATC CTGCCTCACA

1861 CCTTCGGCTT TATCGTGCCC CTGTTCGTGA TGCTGTTCTG CTACGGCTTC ACCCTGCGGA

1921 CCCTGTTCAA AGCCCACATG GGCCAGAAAC ACCGGGCCAT GAGAGTGATC TTTGCCGTGG

1981 TGCTGATCTT CCTGCTGTGC TGGCTGCCCT ACAACCTGGT GCTGCTTGCC GACACACTGA

2041 TGCGGACCCA AGTGATCCAA GAGAGCTGCG AGCGGCGGAA CAATATCGGC AGAGCCCTGG

2101 ATGCTACCGA GATCCTGGGC TTCCTGCACA GCTGTCTGAA CCCCATCATC TACGCCTTCA

2161 TCGGCCAGAA CTTCCGGCAC GGCTTTCTGA AGATTCTGGC CATGCACGGC CTGGTGTCCA

2221 AAGAGTTCCT GGCCAGACAC AGAGTGACCA GCTACACCAG CAGCTCCGTG AACGTGTCCA

2281 GCAACCTCTG AGTCGAC
```

| Element | Description | Location(bases) |
|---------|-------------|-----------------|
| CD70CAR | Extracellular CD27 + Intracellular 41bb + CD3zeta; codon optimized | 3-1103 |
| fuV5P2A | Furin, V5 peptide, P2A ribosomal skip peptide | 1113-1232 |
| CXCR1 | Human CXCR1; codon optimized | 1239-2291 |

SEQ ID NO: 2-Human CD70CAR-CXCR2 2327 bp
(SEQ ID NO: 2)

```
  1 CCATGGCAAG ACCCCACCCC TGGTGGCTGT GTGTGCTGGG CACACTGGTC TGGACTGAGCG

61 CCACCCCTGC CCCTAAGAGC TGCCCCGAGA GACACTACTG GGCTCAGGGC AAGCTGTGCT

121 GCCAGATGTG CGAGCCCGGC ACCTTCCTGG TGAAAGACTG CGACCAGCAC CGGAAGGCCG

181 CCCAGTGCGA TCCTTGCATC CCCGGCGTGT CCTTCAGCCC CGACCACCAC ACCAGACCCC

241 ACTGCGAGAG CTGCCGGCAT TGCAACTCTG GCCTGCTGGT CCGCAACTGC ACCATCACCG

301 CCAACGCCGA GTGCGCCTGC AGAAACGGCT GGCAGTGCCG GGACAAAGAA TGCACCGAGT

361 GCGACCCTCT GCCCAACCCC AGCCTGACCG CCAGAAGCAG CCAGGCTCTG AGCCCTCACC

421 CTCAGCCCAC CCATCTGCCC TACGTGTCCG AGATGCTGGA AGCCCGGACA GCCGGCCACA

481 TGCAGACCCT GGCCGACTTC AGACAGCTGC CGCCAGAAC CCTGAGCACC CACTGGCCTC

541 CCCAGCGGAG CCTGTGCAGC AGCGACTTCA TCCGGATCCT GGTGATCTTC AGCGGCATGT

601 TCCTGGTGTT CACCCTGGCT GGCGCCCTGT TCCTGCACAA GCGGGGCAGA AAGAAGCTGC

661 TGTACATCTT CAAGCAGCCC TTCATGCGGC CCGTGCAGAC CACCCAGGAA GAGGACGGCT
```

```
 721 GCAGCTGCCG GTTCCCCGAG GAAGAGGAAG GCGGCTGCGA GCTGAGAGTG AAGTTCAGCA
 781 GAAGCGCCGA CGCCCCTGCC TACCAGCAGG GCCAGAACCA GCTGTACAAC GAGCTGAACC
 841 TGGGCAGACG GGAAGAGTAC GACGTGCTGG ACAAGCGGAG AGGCCGGGAC CCTGAGATGG
 901 GCGGCAAGCC CCAGAGGCGG AAGAACCCTC AGGAAGGCCT GTATAACGAA CTGCAGAAAG
 961 ACAAGATGGC CGAGGCCTAC AGCGAGATCG GCATGAAGGG CGAGCGGCGG AGAGGCAAGG
1021 GCCACGATGG CCTGTACCAG GGCCTGAGCA CCGCCACCAA GGACACCTAC GACGCCCTGC
1081 ACATGCAGGC TCTGCCTCCA AGATTAATTA CCGTGCCAA GCGAGGTAAG CCTATCCCTA
1141 ACCCTCTCCT CGGTCTCGAT TCTACGGGAT CCGGAGCCAC GAACTTCTCT CTGTTAAAGC
1201 AAGCAGGAGA CGTGGAAGAA AACCCCGGTC CTTTCGAAAT GGAAGATTTC AACATGGAAA
1261 GCGACAGCTT CGAGGACTTC TGGAAAGGCG AGGACCTGAG CAACTACAGC TACAGCTCTA
1321 CCCTGCCTCC TTTCCTGCTG GATGCCGCTC CTTGTGAACC CGAGAGCCTG GAAATCAACA
1381 AGTACTTCGT GGTCATTATC TACGCCCTGG TGTTCCTGCT GAGCCTGCTG GCAATAGCC
1441 TGGTCATGCT GGTCATCCTG TACAGCAGAG TGGGCAGATC CGTGACCGAC GTGTACCTGC
1501 TGAATCTGGC CCTGGCCGAT CTGCTGTTTG CCCTGACACT GCCTATTTGG GCCGCCAGCA
1561 AAGTGAACGG CTGGATCTTC GGCACCTTCC TGTGCAAGGT GGTGTCTCTG CTGAAAGAAG
1621 TGAACTTCTA CTCCGGCATC CTGCTGCTGG CCTGCATCAG CGTTGACAGA TACCTGGCCA
1681 TCGTGCACGC CACCAGAACA CTGACCCAGA AGCGCTACCT GGTCAAGTTC ATCTGCCTGA
1741 GCATCTGGGG ACTGTCCCTG CTGCTTGCTC TGCCTGTGCT GCTGTTTCGG AGAACCGTGT
1801 ACAGCTCCAA CGTGTCCCCT GCCTGCTACG AGGACATGGG CAACAACACC GCCAACTGGC
1861 GGATGCTGCT GAGAATCCTG CCTCAGAGCT TCGGCTTCAT CGTGCCCCTG CTGATCATGC
1921 TGTTCTGCTA CGGCTTCACC CTGCGGACCC TGTTCAAAGC CCACATGGGC CAGAAACACC
1981 GGGCCATGAG AGTGATCTTT GCCGTGGTGC TGATCTTCCT GCTGTGCTGG CTGCCCTACA
2041 ACCTGGTGCT TCTGGCCGAC ACACTGATGC GGACCCAAGT GATCCAAGAG ACATGCGAGC
2101 GGCGGAACCA CATCGACAGA GCCCTGGATG CCACAGAGAT CCTGGGAATC CTGCACAGCT
2161 GCCTGAATCC TCTGATCTAC GCCTTCATCG ACAGAAGTT CCGGCACGGC CTGCTGAAGA
2221 TTCTGGCCAT CCACGGCCTG ATCAGCAAGG ACAGCCTGCC TAAGGACAGC AGACCTAGCT
2281 TGTGTGGGCAG CAGCAGCGGC CACACAAGCA CCACACTTTG AGTCGAC
```

| Element | Description | Location(bases) |
|---|---|---|
| CD70CAR | Extracellular CD27 + Intracellular 41bb + CD3zeta; codon optimized | 3-1103 |
| fuV5P2A | Furin, V5 peptide, P2A ribosomal skip peptide | 1113-1232 |
| CXCR2 | Human CXCR2; codon optimized | 1239-2321 |

SEQ ID NO: 3-Human CD70CAR-EGFP 1964 bp
(SEQ ID NO: 3)
```
  1 CCATGGCAAG ACCCCACCCC TGGTGGCTGT GTGTGCTGGG CACACTGGTC GGACTGAGCG
 61 CCACCCCTGC CCCTAAGAGC TGCCCCGAGA GACACTACTG GGCTCAGGGC AAGCTGTGCT
121 GCCAGATGTG CGAGCCCGGC ACCTTCCTGG TGAAAGACTG CGACCAGCAC CGGAAGGCCG
181 CCCAGTGCGA TCCTTGCATC CCCGGCGTGT CCTTCAGCCC CGACCACCAC ACCAGACCCC
241 ACTGCGAGAG CTGCCGGCAT TGCAACTCTG GCCTGCTGGT CCGCAACTGC ACCATCACCG
301 CCAACGCCGA GTGCGCCTGC AGAAACGGCT GGCAGTGCCG GGACAAAGAA TGCACCGAGT
```

-continued

```
 361 GCGACCCTCT GCCCAACCCC AGCCTGACCG CCAGAAGCAG CCAGGCTCTG AGCCCTCACC

421 CTCAGCCCAC CCATCTGCCC TACGTGTCCG AGATGCTGGA AGCCCGGACA GCCGGCCACA

481 TGCAGACCCT GGCCGACTTC AGACAGCTGC CCGCCAGAAC CCTGAGCACC CACTGGCCTC

541 CCCAGCGGAG CCTGTGCAGC AGCGACTTCA TCCGGATCCT GGTGATCTTC AGCGGCATGT

601 TCCTGGTGTT CACCCTGGCT GGCGCCCTGT TCCTGCACAA GCGGGGCAGA AGAAGCTGC

661 TGTACATCTT CAAGCAGCCC TTCATGCGGC CCGTGCAGAC CACCCAGGAA GAGGACGGCT

721 GCAGCTGCCG GTTCCCCGAG AAGAGGAAG GCGGCTGCGA GCTGAGAGTG AAGTTCAGCA

781 GAAGCGCCGA CGCCCCTGCC TACCAGCAGG GCCAGAACCA GCTGTACAAC GAGCTGAACC

841 TGGGCAGACG GGAAGAGTAC GACGTGCTGG ACAAGCGGAG AGGCCGGGAC CTGAGATGG

901 GCGGCAAGCC CCAGAGGCGG AAGAACCCTC AGGAAGGCCT GTATAACGAA CTGCAGAAAG

961 ACAAGATGGC CGAGGCCTAC AGCGAGATCG GCATGAAGGG CGAGCGGCGG AGAGGCAAGG

1021 GCCACGATGG CCTGTACCAG GGCCTGAGCA CCGCCACCAA GGACACCTAC GACGCCCTGC

1081 ACATGCAGGC TCTGCCTCCA AGATTAATTA ACCGTGCCAA GCGAGGTAAG CCTATCCCTA

1141 ACCCTCTCCT CGGTCTCGAT TCTACGGGAT CCGGAGCCAC GAACTTCTCT CTGTTAAAGC

1201 AAGCAGGAGA CGTGGAAGAA AACCCCGGTC CTTTCGAAAT GGTGAGCAAG GGAGAGGAGC

1261 TGTTCACCGG GGTGGTGCCC ATCCTGGTCG AGCTGGACGG CGACGTAAAC GGCCACAAGT

1321 TCAGCGTGTC CGGCGAGGGC GAGGGCGATG CCACCTACGG CAAGCTGACC CTGAAGTTCA

1381 TCTGCACCAC CGGCAAGCTG CCCGTGCCCT GGCCCACCCT CGTGACCACC CTGACCTACG

1441 GCGTGCAGTG CTTCAGCCGC TACCCCGACC ACATGAAGCA GCACGACTTC TTCAAGTCCG

1501 CCATGCCCGA AGGCTACGTC CAGGAGCGCA CCATCTTCTT CAAGGACGAC GGCAACTACA

1561 AGACCCGCGC CGAGGTGAAG TTCGAGGGCG ACACCCTGGT GAACCGCATC GAGCTGAAGG

1621 GCATCGACTT CAAGGAGGAC GGCAACATCC TGGGGCACAA GCTGGAGTAC AACTACAACA

1681 GCCACAACGT CTATATCATG GCCGACAAGC AGAAGAACGG CATCAAGGTG AACTTCAAGA

1741 TCCGCCACAA CATCGAGGAC GGCAGCGTGC AGCTCGCCGA CCACTACCAG CAGAACACCC

1801 CCATCGGCGA CGGCCCCGTG CTGCTGCCCG ACAACCACTA CCTGAGCACC CAGTCCGCCC

1861 TGAGCAAAGA CCCCAACGAG AAGCGCGATC ACATGGTCCT GCTGGAGTTC GTGACCGCCG

1921 CCGGGATCAC TCTCGGCATG GATGAGCTGT ACAAGTAGGT CGAC
```

| Element | Description | Location(bases) |
|---|---|---|
| CD70CAR | Extracellular CD27 + Intracellular 41bb + CD3zeta; codon optimized | 3-1103 |
| fuV5P2A | Furin, V5 peptide, P2A ribosomal skip peptide | 1113-1232 |
| EGFP | EGFP; codon optimized | 1239-1958 |

SEQ ID NO: 4-Human CXCR1
(SEQ ID NO: 4)
```
CC GAGACACTGA ACAAATACGT GGTCATCATT GCCTACGCTC TGGTGTTCCT GCTGAGCCTG

CTGGGCAATA GCCTGGTCAT GCTGGTCATC CTGTACAGCA GAGTGGGCAG ATCCGTGACC

GACGTGTACC TGCTGAATCT GGCCCTGGCC GATCTGCTGT TTGCCCTGAC ACTGCCTATT

TGGGCCGCCA GCAAAGTGAA CGGCTGGATC TTCGGCACCT TCCTGTGCAA GGTGGTGTCT

CTGCTGAAAG AAGTGAACTT CTACAGCGGC ATCCTGCTGC TGGCCTGCAT CAGCGTTGAC
```

```
AGATACCTGG CCATCGTGCA CGCCACCAGA ACACTGACCC AGAAGAGACA CCTGGTCAAG

TTCGTGTGCC TCGGCTGTTG GGGCCTGAGC ATGAATCTGT TCTCTGCCATT CTTCCTGTTC

CGGCAGGCCT ACCATCCTAA CAACAGCAGC CCTGTGTGCT ACGAGGTGCT GGGAAACGAT

ACAGCCAAGT GGCGGATGGT GCTGCGGATC CTGCCTCACA CCTTCGGCTT TATCGTGCCC

CTGTTCGTGA TGCTGTTCTG CTACGGCTTC ACCCTGCGGA CCCTGTTCAA AGCCCACATG

GGCCAGAAAC ACCGGGCCAT GAGAGTGATC TTTGCCGTGG TGCTGATCTT CCTGCTGTGC

TGGCTGCCCT ACAACCTGGT GCTGCTTGCC GACACACTGA TGCGGACCCA AGTGATCCAA

GAGAGCTGCG AGCGGCGGAA CAATATCGGC AGAGCCCTGG ATGCTACCGA GATCCTGGGC

TTCCTGCACA GCTGTCTGAA CCCCATCATC TACGCCTTCA TCGGCCAGAA CTTCCGGCAC

GGCTTTCTGA AGATTCTGGC CATGCACGGC CTGGTGTCCA AAGAGTTCCT GGCCAGACAC

AGAGTGACCA GCTACACCAG CAGCTCCGTG AACGTGTCCA GCAACCTCTG A
```

SEQ ID NO: 5-Human CXCR2                                                     (SEQ ID NO: 5)

```
   TG GATGCCGCTC CTTGTGAACC CGAGAGCCTG GAAATCAACA AGTACTTCGT GGTCATTATC

TACGCCCTGG TGTTCCTGCT GAGCCTGCTG GGCAATAGCC TGGTCATGCT GGTCATCCTG

TACAGCAGAG TGGGCAGATC CGTGACCGAC GTGTACCTGC TGAATCTGGC CCTGGCCGAT

CTGCTGTTTG CCCTGACACT GCCTATTTGG GCCGCCAGCA AAGTGAACGG CTGGATCTTC

GGCACCTTCC TGTGCAAGGT GGTGTCTCTG CTGAAAGAAG TGAACTTCTA CTCCGGCATC

CTGCTGCTGG CCTGCATCAG CGTTGACAGA TACCTGGCCA TCGTGCACGC CACCAGAACA

CTGACCCAGA AGCGCTACCT GGTCAAGTTC ATCTGCCTGA GCATCTGGGG ACTGTCCCTG

CTGCTTGCTC TGCCTGTGCT GCTGTTTCGG AGAACCGTGT ACAGCTCCAA CGTGTCCCCT

GCCTGCTACG AGGACATGGG CAACAACACC GCCAACTGGC GGATGCTGCT GAGAATCCTG

CCTCAGAGCT TCGGCTTCAT CGTGCCCCTG CTGATCATGC TGTTCTGCTA CGGCTTCACC

CTGCGGACCC TGTTCAAAGC CCACATGGGC CAGAAACACC GGGCCATGAG AGTGATCTTT

GCCGTGGTGC TGATCTTCCT GCTGTGCTGG CTGCCCTACA ACCTGGTGCT TCTGGCCGAC

ACACTGATGC GGACCCAAGT GATCCAAGAG ACATGCGAGC GGCGGAACCA CATCGACAGA

GCCCTGGATG CCACAGAGAT CCTGGGAATC CTGCACAGCT GCCTGAATCC TCTGATCTAC

GCCTTCATCG GACAGAAGTT CCGGCACGGC CTGCTGAAGA TTCTGGCCAT CCACGGCCTG

ATCAGCAAGG ACAGCCTGCC TAAGGACAGC AGACCTAGCT TTGTGGGCAG CAGCAGCGGC

CACACAAGCA CCACACTTTG A
```

SEQ ID NO: 6-Human CD70 CAR                                              (SEQ ID NO: 6)

```
    1   TGGCAAG ACCCCACCCC TGGTGGCTGT GTGTGCTGGG CACACTGGTC GGACTGAGCG

61   CCACCCCTGC CCCTAAGAGC TGCCCCGAGA CACTACTG GGCTCAGGGC AAGCTGTGCT

121   GCCAGATGTG CGAGCCCGGC ACCTTCCTGG TGAAAGACTG CGACCAGCAC CGGAAGGCCG

181   CCCAGTGCGA TCCTTGCATC CCCGGCGTGT CCTTCAGCCC CGACCACCAC ACCAGACCCC

241   ACTGCGAGAG CTGCCGGCAT TGCAACTCTG GCCTGCTGGT CCGCAACTGC ACCATCACCG

301   CCAACGCCGA GTGCGCCTGC AGAAACGGCT GGCAGTGCCG GGACAAAGAA TGCACCGAGT

361   GCGACCCTCT GCCCAACCCC AGCCTGACCG CCAGAAGCAG CCAGGCTCTG AGCCCTCACC

421   CTCAGCCCAC CCATCTGCCC TACGTGTCCG AGATGCTGGA AGCCCGGACA GCCGGCCACA

481   TGCAGACCCT GGCCGACTTC AGACAGCTGC CGCCAGAAC CTGAGCACC CACTGGCCTC

541   CCCAGCGGAG CCTGTGCAGC AGCGACTTCA TCCGGATCCT GGTGATCTTC AGCGGCATGT

601   TCCTGGTGTT CACCCTGGCT GGCGCCCTGT TCCTGCACAA GCGGGGCAGA AAGAAGCTGC
```

```
 661 TGTACATCTT CAAGCAGCCC TTCATGCGGC CCGTGCAGAC CACCCAGGAA GAGGACGGCT

721 GCAGCTGCCG GTTCCCCGAG GAAGAGGAAG GCGGCTGCGA GCTGAGAGTG AAGTTCAGCA

781 GAAGCGCCGA CGCCCCTGCC TACCAGCAGG GCCAGAACCA GCTGTACAAC GAGCTGAACC

841 TGGGCAGACG GGAAGAGTAC GACGTGCTGG ACAAGCGGAG AGGCCGGGAC CCTGAGATGG

901 GCGGCAAGCC CCAGAGGCGG AAGAACCCTC AGGAAGGCCT GTATAACGAA CTGCAGAAAG

961 ACAAGATGGC CGAGGCCTAC AGCGAGATCG GCATGAAGGG CGAGCGGCGG AGAGGCAAGG

1021 GCCACGATGG CCTGTACCAG GGCCTGAGCA CCGCCACCAA GGACACCTAC GACGCCCTGC

1081 ACATGCAGGC TCTGCCTCCA AGA

SEQ ID NO: 7-fuV5P2A
                                                       (SEQ ID NO: 7)
CGTGCCAA GCGAGGTAAG CCTATCCCTA ACCCTCTCCT CGGTCTCGAT TCTACGGGAT

CCGGAGCCAC GAACTTCTCT CTGTTAAAGC AAGCAGGAGA CGTGGAAGAA AACCCCGGTC CT

SEQ ID NO: 8-EGFP
                                                       (SEQ ID NO: 8)
GC GAGGGCGATG CCACCTACGG CAAGCTGACC CTGAAGTTCA TCTGCACCAC CGGCAAGCTG

CCCGTGCCCT GGCCCACCCT CGTGACCACC CTGACCTACG GCGTGCAGTG CTTCAGCCGC

TACCCCGACC ACATGAAGCA GCACGACTTC TTCAAGTCCG CCATGCCCGA AGGCTACGTC

CAGGAGCGCA CCATCTTCTT CAAGGACGAC GGCAACTACA AGACCCGCGC CGAGGTGAAG

TTCGAGGGCG ACACCCTGGT GAACCGCATC GAGCTGAAGG GCATCGACTT CAAGGAGGAC

GGCAACATCC TGGGGCACAA GCTGGAGTAC AACTACAACA GCCACAACGT CTATATCATG

GCCGACAAGC AGAAGAACGG CATCAAGGTG AACTTCAAGA TCCGCCACAA CATCGAGGAC

GGCAGCGTGC AGCTCGCCGA CCACTACCAG CAGAACACCC CCATCGGCGA CGGCCCCGTG

CTGCTGCCCG ACAACCACTA CCTGAGCACC CAGTCCGCCC TGAGCAAAGA CCCCAACGAG

AAGCGCGATC ACATGGTCCT GCTGGAGTTC GTGACCGCCG CCGGGATCAC TCTCGGCATG

GATGAGCTGT ACAAGTAG
```

Having described many embodiments in detail, it will be apparent that modifications and variations are possible without departing from the scope of the invention defined in the appended claims. Furthermore, it should be appreciated that all examples in the present disclosure, while illustrating many embodiments, are provided as non-limiting examples and are, therefore, not to be taken as limiting the various aspects so illustrated.

It is intended that the invention not be limited to the particular embodiment disclosed herein contemplated for carrying out this invention, but that the invention will include all embodiments falling within the scope of the claims.

REFERENCES

The following references are referred to above and are incorporated herein by reference:
1. Stupp R, et al. *Lancet Oncol.* 2009; 10(5):459-466.
2. Stupp R, et al., *N Engl J Med.* 2005; 352(10):987-996.
3. Mellman I, et al., *Nature.* 2011; 480(7378):480-489.
4. Rosenberg S A, et al., *Nat Rev Cancer.* 2008; 8(4):299-308.
5. Morgan R A, et al., *Hum Gene Ther.* 2012; 23(10):1043-1053.
6. Bowman M R, et al., *J Immunol.* 1994; 152(4):1756-1761.
7. Hintzen R Q, et al., *J Immunol.* 1994; 152(4):1762-1773.
8. Hintzen R Q, et al., *J Immunol.* 1995; 154(6):2612-2623.
9. Nolte M A, et al., *Immunol Rev.* 2009; 229(1):216-231.
10. Held-Feindt J, et al., *Int J Cancer.* 2002; 98(3):352-356.
11. Ryan M C, et al., *Br J Cancer.* 010; 103(5):676-684.
12. Wischhusen J, et al., *Cancer Res.* 2002; 62(9):2592-2599.
13. Adam P J, et al., *Br J Cancer.* 2006; 95(3):298-306.
14. Huang J, et al., *J Immunol.* 2006; 176(12):7726-7735.
15. Keller A M, et al., *Blood.* 2009; 113(21):5167-5175.
16. Chahlavi A, et al., *Cancer Res.* 2005; 65(12):5428-5438.
17. Diegmann J, et al., *Neoplasia.* 2006; 8(11):933-938.
18. Ruf M, et al., *Clin Cancer Res.* 2015; 21(4):889-898.
19. Wang Q J, et al., *Clinical Cancer Research.* 2016.
20. Johnson L A, et al., *Science Translational Medicine.* 2015; 7(275):275ra222-275ra222.
21. Zhou J, et al., *J Immunol.* 2005; 175(10):7046-7052.
22. Che J W, et al., *J Virol.* 2015; 89(4):2112-2120.
23. Verhaak R G, et al., *Cancer Cell.* 2010; 17(1):98-110.
24. Ge H, et al., *Int J Cancer.* 2017. doi:10.1002/ijc.30830
25. Chanmee T, et al., *Cancers (Basel).* 2014; 6(3):1670-1690.
26. Oelkrug C, et al., *Clin Exp Immunol.* 2014; 178(1):1-8.
27. Network TCGAR. Comprehensive, integrative genomic analysis of diffuse lower-grade gliomas. *N Engl J Med.* 2015; 372(26):2481-2498.
28. Silence K, Dreier T, Moshir M, et al. *ARGX-110, a highly potent antibody targeting CD70, eliminates tumors*

*via both enhanced ADCC and immune checkpoint blockade*. Paper presented at: MAbs2014.
29. Shaffer D R, et al., *Blood.* 2011; 117(16):4304-4314.
30. Engelhardt B. *J Neural Transm (Vienna).* 2006; 113(4): 477-485.
31. Miao H, et al., *PLoS One.* 2014; 9(4):e94281.
32. Brown C E, et al., *N Engl J Med.* 2016; 375(26):2561-2569.
33. Huang J, et al., *J Immunol.* 2013; 190(12):6250-6258.
34. Abolhassani H, et al., *J Exp Med.* 2017; 214(1):91-106.
35. Izawa K, et al., *J Exp Med.* 2017; 214(1):73-89.
36. Huang J, et al., *J Immunother.* 2011; 34(4):327-335.
37. Linchun Jin, et al., *Neuro-Oncology.* xx(xx): 1-11, 2017
38. Krenciute G, et al., *Mol Ther* 2016; 24(2):354-63 doi 10.1038/mt.2015.199.
39. Ahmed N, et al., American Association for Cancer Research 2010; 16(2):474-85 doi 10.1158/1078-0432.ccr-09-1322.
40. Chow K K, et al., *Molecular Therapy.* 2013 Mar. 31; 21(3):629-37.
41. Shiina S, et al., *Cancer Immunology Research* 2016; 4(3):259-68 doi 10.1158/2326-6066.cir-15-0060.
42. Liu Q, et al., *Cytokine Growth Factor Rev.* 2016 October; 31:61-71. doi: 10.1016/j.cytogfr.2016.08.002. Epub 2016 Aug. 25.
43. Trebing, J., et al. (2014). *Cell Death & Disease* 5(1).
44. Jacobs, J., et al. (2015). *Pharmacol Ther* 155: 1-10.
45. Yang, S. et al. *Gene therapy* 15.21 (2008): 1411-23.

All documents, patents, patent applications, journal articles and other materials cited in the present application are incorporated herein by reference.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A nucleic acid comprising a nucleic acid sequence at least 90% identical to the sequence of SEQ ID NO: 1 or SEQ ID NO:2.

2. The nucleic acid of claim 1, comprising the nucleic acid sequence set forth in SEQ ID NO: 1.

3. The nucleic acid of claim 1, comprising the nucleic acid sequence set forth in SEQ ID NO: 2.

4. A modified T cell comprising a nucleic acid sequence at least 90% identical to the sequence of SEQ ID NO: 1 or SEQ ID NO:2.

5. The modified T cell of claim 4, wherein the nucleic acid sequence comprises the sequence set forth in SEQ ID NO: 1.

6. The modified T cell of claim 4, wherein the nucleic acid sequence comprises the sequence set forth in SEQ ID NO: 2.

7. A method of treating a brain tumor comprising: administering a modified T cell comprising the nucleic acid set forth in SEQ ID NO: 1 or SEQ ID NO: 2 to a subject in need thereof.

8. The method of claim 7, wherein the nucleic acid sequence comprises the sequence of SEQ ID NO: 1.

9. The method of claim 7, wherein the nucleic acid sequence comprises the sequence of SEQ ID NO: 2.

10. The method of claim 7, wherein the modified T cell is administered to the subject in need thereof by intravenous injection or infusion.

11. The method of claim 7, wherein the subject in need thereof has glioma.

12. The method of claim 7, wherein the T cell is obtained from a donor subject which is different than the subject administered the modified T cell.

* * * * *